United States Patent
Bell et al.

(10) Patent No.: US 9,227,973 B2
(45) Date of Patent: Jan. 5, 2016

(54) PYRIDINE CGRP RECEPTOR ANTAGONISTS

(71) Applicant: Merck Sharp & Dohme Corp., Rahway, NJ (US)

(72) Inventors: Ian M. Bell, Plainsboro, NJ (US); Mark Fraley, North Wales, PA (US); Tesfaye Biftu, Freehold, NJ (US); Cheng Zhu, Edison, NJ (US); Anilkumar Nair, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/399,762

(22) PCT Filed: May 3, 2013

(86) PCT No.: PCT/US2013/039359
§ 371 (c)(1),
(2) Date: Nov. 7, 2014

(87) PCT Pub. No.: WO2013/169563
PCT Pub. Date: Nov. 14, 2013

(65) Prior Publication Data
US 2015/0099771 A1 Apr. 9, 2015

Related U.S. Application Data

(60) Provisional application No. 61/644,638, filed on May 9, 2012.

(51) Int. Cl.
*C07D 471/10* (2006.01)
*C07D 471/20* (2006.01)
*C07D 519/00* (2006.01)

(52) U.S. Cl.
CPC ............ *C07D 471/20* (2013.01); *C07D 471/10* (2013.01); *C07D 519/00* (2013.01)

(58) Field of Classification Search
CPC ........................... C07D 471/10; C07D 471/20
USPC ............................................ 514/278; 546/15
See application file for complete search history.

(56) References Cited

U.S. PATENT DOCUMENTS

| | | |
|---|---|---|
| 2004/0235823 A1 | 11/2004 | Bridger et al. |
| 2007/0293470 A1 | 12/2007 | Williams et al. |
| 2010/0069359 A1 | 3/2010 | Bell et al. |
| 2011/0263564 A1 | 10/2011 | Narayan et al. |

*Primary Examiner* — Rita Desai
(74) *Attorney, Agent, or Firm* — John C. Todaro; H. Eric Fischer

(57) ABSTRACT

The present invention is directed to pyridine derivatives which are antagonists of CGRP receptors and useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

4 Claims, No Drawings

PYRIDINE CGRP RECEPTOR ANTAGONISTS

CROSS-REFERENCE TO RELATED APPLICATIONS

This application is the national stage entry of International Patent Application Serial No. PCT/US2013/039359 filed May 3, 2013, which in turn claims the priority of U.S. provisional application serial no. 61/644,638 filed May 9, 2012, which applications are incorporated herein in their entirety by reference thereto.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to the CGRP receptor which is a heterodimer consisting of the G-protein coupled calcitonin-like receptor (CLR) in association with the single transmembrane protein known as receptor activity modifying protein 1 ($RAMP_1$). CGRP receptors are predominantly coupled to the activation of adenylyl cyclase and have been identified and pharmacologically evaluated in several tissues and cells, including those of brain, cardiovascular, endothelial, and smooth muscle origin.

CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al. (1990) Ann. Neurol. 28, 183-187), salivary levels of CGRP are elevated in migraine subjects between (Bellamy et al. (2006) Headache 46, 24-33) and during attacks (Cady et al. (2009) Headache 49, 1258-1266), and CGRP itself has been shown to trigger migrainous headache (Lassen et al. (2002) Cephalalgia 22, 54-61). In clinical trials, the CGRP receptor antagonist BIBN4096BS has been shown to be effective in treating acute attacks of migraine (Olesen et al. (2004) New Engl. J. Med. 350, 1104-1110) and was able to prevent headache induced by CGRP infusion in a control group (Petersen et al. (2005) Clin. Pharmacol. Ther. 77, 202-213). The orally bioavailable CGRP receptor antagonist telcagepant has also shown antimigraine effectiveness in phase III clinical trials (Ho et al. (2008) Lancet 372, 2115-2123; Connor et al. (2009) Neurology 73, 970-977).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al. (1988) Ann. Neurol. 23, 193-196). Electrical stimulation of the dura mater in rats increased the diameter of the middle meningeal artery, an effect that was blocked by prior administration of CGRP(8-37), a peptide CGRP receptor antagonist (Williamson et al. (1997) Cephalalgia 17, 525-531). Trigeminal ganglion stimulation increased facial blood flow in the rat, which was inhibited by CGRP(8-37) (Escott et al. (1995) Brain Res. 669, 93-99). Electrical stimulation of the trigeminal ganglion in marmoset produced an increase in facial blood flow that could be blocked by the non-peptide CGRP receptor antagonist BIBN4096BS (Doods et al. (2000) Br. J. Pharmacol. 129, 420-423). Thus the vascular effects of CGRP may be attenuated, prevented or reversed by a CGRP receptor antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al. (2000) Ann. Neurol. 47, 614-624). A CGRP antagonist may be beneficial in attenuating, preventing or reversing the effects of neuronal sensitization.

The ability of the compounds of the present invention to act as CGRP receptor antagonists makes them useful pharmacological agents for disorders that involve CGRP in humans and animals, but particularly in humans. Such disorders include migraine and cluster headache (Doods (2001) Curr. Opin. Invest. Drugs 2, 1261-1268; Edvinsson et al. (1994) Cephalalgia 14, 320-327); chronic tension type headache (Ashina et al. (2000) Neurology 14, 1335-1340); pain (Yu et al. (1998) Eur. J. Pharmacol. 347, 275-282); chronic pain (Hulsebosch et al. (2000) Pain 86, 163-175); neurogenic inflammation and inflammatory pain (Holzer (1988) Neuroscience 24, 739-768; Delay-Goyet et al. (1992) Acta Physiol. Scanda. 146, 537-538; Salmon et al. (2001) Nature Neurosci. 4, 357-358); eye pain (May et al. (2002) Cephalalgia 22, 195-196), tooth pain (Awawdeh et al. (2002) Int. Endocrin. J. 35, 30-36), non-insulin dependent diabetes mellitus (Molina et al. (1990) Diabetes 39, 260-265); vascular disorders; inflammation (Zhang et al. (2001) Pain 89, 265); arthritis, bronchial hyperreactivity, asthma, (Foster et al. (1992) Ann. NY Acad. Sci. 657, 397-404; Schini et al. (1994) Am. J. Physiol. 267, H2483-H2490; Zheng et al. (1993) J. Virol. 67, 5786-5791); shock, sepsis (Beer et al. (2002) Crit. Care Med. 30, 1794-1798); opiate withdrawal syndrome (Salmon et al. (2001) Nature Neurosci. 4, 357-358); morphine tolerance (Menard et al. (1996) J. Neurosci. 16, 2342-2351); hot flashes in men and women (Chen et al. (1993) Lancet 342, 49; Spetz et al. (2001) J. Urology 166, 1720-1723); allergic dermatitis (Wallengren (2000) Contact Dermatitis 43, 137-143); psoriasis; encephalitis, brain trauma, ischaemia, stroke, epilepsy, and neurodegenerative diseases (Rohrenbeck et al. (1999) Neurobiol. Dis. 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al. (2002) J. Membr. Biol. 189, 225); obesity (Walker et al. (2010) Endocrinology 151, 4257-4269); inflammatory bowel disease, irritable bowel syndrome, (Hoffman et al. (2002) Scand. J. Gastroenterol. 37, 414-422) and cystitis. Of particular importance is the acute or prophylactic treatment of headache, including migraine and cluster headache.

SUMMARY OF THE INVENTION

The present invention is directed to pyridine derivatives which are potent antagonists of CGRP receptors and may be useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of Formula I:

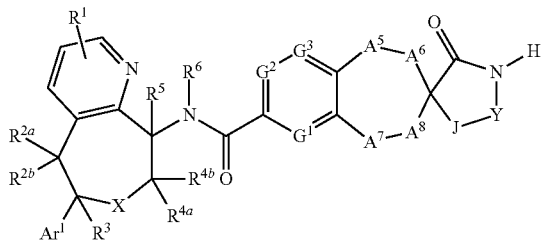

I or a pharmaceutically acceptable salt thereof, wherein:
$Ar^1$ is phenyl or heterocycle, wherein the heterocycle is selected from pyridinyl, pyrimidinyl, pyrazinyl, thienyl, pyridazinyl, indolinyl, indolyl, pyrazolyl, and indazolyl, wherein the phenyl or heterocycle is optionally substituted with 1-5 substituents each independently selected from the group consisting of:
 (a) —$C_{1-6}$ alkyl which is optionally substituted with 1-6 halo,
 (b) halo,
 (c) —$OR^a$,
 (d) —$C_{1-6}$ cycloalkyl,
 (e) phenyl or heterocycle, wherein the heterocycle is selected from pyridinyl, pyrimidinyl, pyrazinyl, thienyl and morpholinyl, and wherein the phenyl or heterocycle is optionally substituted with 1-5 substituents each independently selected from the group consisting of $C_{1-6}$alkyl, —O—$C_{1-6}$alkyl, halo, hydroxy and trifluoromethyl,
 (f) —$CO_2R^a$,
 (g) —$NR^bR^c$,
 (h) —$CONR^bR^c$,
 (i) —$SO_2R^d$, and
 (j) —CN;
$R^1$ is selected from:
 (1) hydrogen,
 (2) —$C_{1-6}$ alkyl, which is optionally substituted with 1-7 substituents each independently selected from the group consisting of halo, hydroxy, —O—$C_{1-6}$ alkyl, and —$NR^bR^c$,
 (3) phenyl or heterocycle, wherein the heterocycle is selected from pyridinyl, pyrimidinyl, pyrazinyl, pyrrolidinyl, azetidinyl, triazolyl, tetrazolyl, piperazinyl, pyrazolidinyl, pyrazolyl, tetrahydrofuryl, 1,3-dioxolanyl, oxadiazolyl, piperidinyl and morpholinyl, and wherein the phenyl or heterocycle is optionally substituted with 1-3 substituents each independently selected from the group consisting of:
  (a) —$C_{1-6}$ alkyl which is optionally substituted with 1-6 fluoro,
  (b) halo,
  (c) hydroxy, and
  (d) —O—$C_{1-6}$ alkyl, which is optionally substituted with 1-6 fluoro,
 (4) halo,
 (5) hydroxy,
 (6) —O—$C_{1-6}$ alkyl, which is optionally substituted with 1-6 halo,
 (7) —CN,
 (8) —$CO_2R^a$,
 (9) —$NR^bR^c$,
 (10) —$SO^2R^d$,
 (11) oxo, or
 (12) —$CONR^bR^c$;
$R^{2a}$ and $R^{2b}$ are independently selected from the group consisting of:
 (1) hydrogen,
 (2) —$C_{1-6}$ alkyl, which is optionally substituted with 1-7 substituents each independently selected from the group consisting of halo, hydroxy and —O—$C_{1-6}$alkyl,
 (3) phenyl or heterocycle, wherein the heterocycle is selected from pyridinyl, pyrimidinyl, pyrazinyl, triazolyl, tetrazolyl, pyrazolyl, oxadiazolyl, and morpholinyl, and wherein the phenyl or heterocycle is optionally substituted with 1-3 substituents each independently selected from the group consisting of:
  (a) —$C_{1-6}$ alkyl which is optionally substituted with 1-6 fluoro,
  (b) halo,
  (c) hydroxy, and
  (d) —O—$C_{1-6}$ alkyl, which is optionally substituted with 1-6 fluoro,
 (4) halo,
 (5) —$OR^a$,
 (6) —CN,
 (7) —$CO_2R^a$,
 (8) —$NR^bR^c$,
 (9) —$SO_2R^d$,
 (10) —$CONR^bR^c$, and
 (11) azido,
 or $R^{2a}$ and $R^{2b}$ taken together are =O or =N—OH;
$R^3$ is selected from:
 (1) hydrogen,
 (2) —$C_{1-6}$ alkyl, which is optionally substituted with 1-7 substituents each independently selected from the group consisting of halo, hydroxy and —O—$C_{1-6}$alkyl,
 (3) phenyl or heterocycle, wherein the heterocycle is selected from pyridinyl, pyrimidinyl, pyrazinyl, triazolyl, tetrazolyl, pyrazolyl, oxadiazolyl, and morpholinyl, and wherein the phenyl or heterocycle is optionally substituted with 1-3 substituents each independently selected from the group consisting of:
  (a) —$C_{1-6}$ alkyl which is optionally substituted with 1-6 fluoro,
  (b) halo,
  (c) hydroxy, and
  (d) —O—$C_{1-6}$ alkyl, which is optionally substituted with 1-6 fluoro,
 (4) halo,
 (5) —$OR^a$,
 (6) —CN,
 (7) —$CO_2R^a$,
 (8) —$NR^bR^c$,
 (9) —$SO_2R^d$, or
 (10) —$CONR^bR^c$, or $R^3$ and $Ar^1$ and the carbon atom to which they are attached are joined to form a ring selected from indanyl, tetralinyl, indolinyl, dihydrobenzofuranyl, chromanyl, or tetrahydroquinolinyl, wherein the ring is optionally substituted with 1-5 substituents each independently selected from the group consisting of —$C_{1-6}$alkyl, —O—$C_{1-6}$alkyl, halo, hydroxy, phenyl and benzyl;

$R^{4a}$ and $R^{4b}$ are independently selected from the group consisting of:
  (1) hydrogen,
  (2) —$C_{1-6}$ alkyl, which is optionally substituted with 1-7 substituents each independently selected from the group consisting of halo, hydroxy and —O—$C_{1-6}$alkyl,
  (3) phenyl or heterocycle, wherein the heterocycle is selected from pyridinyl, pyrimidinyl, pyrazinyl, triazolyl, tetrazolyl, pyrazolyl, oxadiazolyl, and morpholinyl, and wherein the phenyl or heterocycle is optionally substituted with 1-3 substituents each independently selected from the group consisting of:
    (a) —$C_{1-6}$ alkyl which is optionally substituted with 1-6 fluoro,
    (b) halo,
    (c) hydroxy, and
    (d) —O—$C_{1-6}$ alkyl, which is optionally substituted with 1-6 fluoro,
  (4) halo,
  (5) —$OR^a$,
  (6) —CN,
  (7) —$CO_2R^a$,
  (8) —$NR^bR^c$,
  (9) —$SO_2R^d$ and
  (10) —$CONR^bR^c$, $R^5$ is selected from:
  (1) hydrogen,
  (2) —$C_{1-6}$ alkyl, which is optionally substituted with 1-7 substituents each independently selected from the group consisting of halo, hydroxy and —O—$C_{1-6}$alkyl,
  (3) —CN, or
  (4) —$CO_2R^a$;

$R^6$ is selected from hydrogen or $C_{1-6}$ alkyl, which is optionally substituted with 1-6 fluoro;

X is selected from:
  (1) a bond,
  (2) —$CR^8R^9$—,
  (3) —$CH_2CR^8R^9$—,
  (4) —O—,
  (5) —N($R^b$)—, or
  (6) —S(O)$_v$—;

$A^5$ and $A^7$ are each independently selected from the group consisting of:
  (1) —O—,
  (2) —S(O)$_v$—,
  (3) —$CR^8R^9$—,
  (4) —N($R^b$)—,
  (5) —(C=O)—, and
  (6) a bond;

$A^6$ and $A^8$ are independently selected from the group consisting of:
  (1) —O—,
  (2) —S(O)$_v$—,
  (3) —$CR^8R^9$—,
  (4) —N($R^b$)—, and
  (5) —(C=O)—;

$G^1$ is selected from:
  (1) —C($R^{7a}$)=,
  (2) —N=, or
  (3) —($N^+$—$O^-$)=;

$G^2$ is selected from:
  (1) —C($R^{7b}$)=,
  (2) —N=, or
  (3) —($N^+$—$O^-$)=;

$G^3$ is selected from:
  (1) —C($R^{7c}$)=,
  (2) —N=, or
  (3) —($N^+$—$O^-$)=;

$R^{7a}$, $R^{7b}$ and $R^{7c}$ are each independently selected from the group consisting of:
  (1) hydrogen,
  (2) —$C_{1-6}$alkyl, which is optionally substituted with 1-6 halo,
  (3) halo,
  (4) —$OR^a$, and
  (5) —CN;

$R^8$ and $R^9$ are independently selected from the group consisting of:
  (1) hydrogen,
  (2) —$C_{1-6}$ alkyl, which is optionally substituted with 1-7 substituents each independently selected from the group consisting of halo, hydroxy and —O—$C_{1-6}$alkyl,
  (3) phenyl or heterocycle, wherein the heterocycle is selected from pyridinyl, pyrimidinyl, pyrazinyl, triazolyl, tetrazolyl, pyrazolyl, oxadiazolyl, and morpholinyl, and wherein the phenyl or heterocycle is optionally substituted with 1-3 substituents each independently selected from the group consisting of:
    (a) —$C_{1-6}$ alkyl which is optionally substituted with 1-6 fluoro,
    (b) halo,
    (c) hydroxy, and
    (d) —O—$C_{1-6}$ alkyl, which is optionally substituted with 1-6 fluoro,
  (4) halo,
  (5) —$OR^a$,
  (6) —CN,
  (7) —$CO_2R^a$,
  (8) —$NR^bR^c$,
  (9) —$SO_2R^d$,
  (10) —$CONR^bR^c$, and
  (11) azido, J is selected from:
  (1) =C($R^{10a}$)—,
  (2) —$CR^{11}R^{12}$—,
  (3) —C(=O)—, or
  (4) —N($R^b$)—;

Y is selected from:
  (1) =C($R^{10b}$)—,
  (2) —$CR^{11}R^{12}$—,
  (3) —C(=O)—,
  (4) =N—, or
  (5) —N($R^c$)—;

$R^{11}$ and $R^{12}$ are each independently selected from the group consisting of:
  (1) hydrogen,
  (2) halo,
  (3) —$OR^a$,
  (4) —$C_{1-6}$alkyl, which is optionally substituted with 1-4 substituents each independently selected from the group consisting of:
    (a) halo,
    (b) —$OR^a$,
    (c) —CN, and
    (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is optionally substituted with 1-5 substituents each independently selected from the group consisting of:
  (i) —OR$^a$,
  (ii) halo,
  (iii) —CN, and
  (iv) —C$_{1-6}$ alkyl which is optionally substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is optionally substituted with 1-5 substituents each independently selected from the group consisting of:
  (a) halo,
  (b) —CN,
  (c) —OR$^a$,
  (d) nitro, and
  (e) —C$_{1-6}$alkyl which is optionally substituted with 1-6 halo;
or R$^{11}$ and R$^{12}$ and the atom to which they are attached join to form a 4-, 5-, or 6-membered ring optionally containing a heteroatom selected from N, O, and S, wherein the sulfur is optionally oxidized to the sulfone or sulfoxide, which ring is optionally substituted with 1-4 substituents each independently selected from the group consisting of:
  (a) halo,
  (b) —OR$^a$,
  (c) —C$_{1-6}$alkyl, which is optionally substituted with 1-6 halo, and
  (d) phenyl;

R$^{10a}$ and R$^{10b}$ are each independently selected from:
(1) hydrogen,
(2) —C$_{1-4}$alkyl, which is optionally substituted with 1-5 substituents each independently selected from the group consisting of:
  (a) halo,
  (b) —OR$^a$,
  (c) —C$_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is optionally substituted with 1-3 substituents each independently selected from the group consisting of:
    (i) halo,
    (ii) —OR$^a$,
    (iii) —CN and
    (iv) C$_{1-6}$alkyl, which is optionally substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is optionally substituted with 1-3 substituents each independently selected from the group consisting of:
  (a) halo,
  (b) —OR$^a$,
  (c) —C$_{3-6}$cycloalkyl,
  (d) —C$_{1-4}$alkyl which is optionally substituted with 1-6 halo, and
  (e) phenyl, which is optionally substituted with 1-5 substituents each independently selected from:
    (i) halo,
    (ii) —C$_{1-6}$alkyl, which is optionally substituted with 1-6 halo and
    (iii) —OR$^a$,
(4) halo,
(5) —OR$^a$,
(6) —CN,
(7) —CO$_2$R$^a$,
(8) —NR$^b$R$^c$, and
(9) —C(=O)NR$^b$R$^c$;
or R$^{10a}$ and R$^{10b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is optionally substituted with 1-5 substituents each independently selected from the group consisting of:
  (a) —C$_{1-6}$alkyl, which is optionally substituted with 1-3 substituents each independently selected from the group consisting of:
    (i) halo,
    (ii) —OR$^a$,
    (iii) —C$_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is optionally substituted with 1-5 substituents each independently selected from the group consisting of:
      (I) —OR$^a$,
      (II) halo,
      (III) —CN, and
      (IV) —C$_{1-6}$alkyl which is optionally substituted with 1-6 halo,
    (v) —CO$_2$R$^a$,
    (vi) —NR$^b$R$^c$,
    (vii) —S(O)$_v$R$^8$,
    (viii) —C(=O)NR$^b$R$^c$,
    (ix) —N(R$^b$)CO$_2$R$^a$, and
    (x) —N(R$^b$)SO$_2$R$^d$,
  (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is optionally substituted with 1-5 substituents each independently selected from the group consisting of:
    (i) halo,
    (ii) —OR$^a$,
    (iii) —CN, and
    (iv) —C$_{1-6}$alkyl which is optionally substituted with 1-6 halo,
  (c) halo,
  (d) —S(O)$_v$R$^8$,
  (e) —OR$^a$,
  (f) —CN,
  (g) —C(=O)R$^a$,
  (h) —NR$^b$R$^c$,
  (i) —C(=O)NR$^b$R$^c$,
  (j) —CO$_2$R$^a$,
  (k) —(NR$^b$)CO$_2$R$^a$,
  (l) —O—(C=O)—NR$^b$R$^c$, (m) —(NR$^b$)—(C=O)—NR$^b$R$^c$,
(n) oxido,
(o) oxo, and
(p) —(NR$^b$)SO$_2$R$^d$;

R$^a$ is selected from:
(1) hydrogen,
(2) C$_{1-6}$alkyl, which is optionally substituted with 1-7 substituents each independently selected from the group consisting of:
 (a) halo,
 (b) —O—C$_{1-6}$ alkyl, which is optionally substituted with 1-6 halo,
 (c) hydroxy,
 (d) —CN, and
 (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
  (i) halo,
  (ii) —O—C$_{1-6}$alkyl, which is optionally substituted with 1-6 halo,
  (iii) —CN,
  (iv) nitro,
  (v) hydroxy, and
  (vi) —C$_{1-6}$alkyl, which is optionally substituted with 1-6 halo,
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
 (a) halo,
 (b) —CN,
 (c) —O—C$_{1-6}$ alkyl, which is optionally substituted with 1-6 halo,
 (d) nitro,
 (e) hydroxy and
 (f) —C$_{1-6}$alkyl, which is optionally substituted with 1-6 halo, and
(4) —C$_{3-6}$cycloalkyl, which is optionally substituted with 1-6 halo;

R$^b$ and R$^c$ are each independently selected from the group consisting of:
(1) hydrogen,
(1) C$_{1-6}$alkyl, which is optionally substituted with 1-7 substituents each independently selected from the group consisting of:
 (a) halo,
 (b) —OR$^a$,
 (c) —CN,
 (d) —CO$_2$R$^a$, and
 (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
  (i) halo,
  (ii) —OR$^a$,
  (iii) —C$_{1-6}$alkyl, which is optionally substituted with 1-6 halo, and
  (iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
 (a) halo,
 (b) —OR$^a$,
 (c) —C$_{1-6}$alkyl, which is optionally substituted with 1-6 halo,
 (d) —C$_{3-6}$cycloalkyl, which is optionally substituted with 1-6 halo,
 (e) —CN, and
 (f) —CO$_2$R$^a$, and
(3) —C$_{3-6}$cycloalkyl, which is optionally substituted with 1-6 halo; or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is optionally substituted with 1-4 substituents each independently selected from the group consisting of:
 (a) halo,
 (b) —OR$^a$, and
 (c) —C$_{1-6}$alkyl, which is optionally substituted with 1-6 halo, and
 (d) phenyl;

R$^d$ is selected from the group consisting of:
(1) C$_{1-6}$alkyl, which is optionally substituted with 1-4 substituents each independently selected from the group consisting of:
 (a) halo,
 (b) —OR$^a$,
 (c) —CO$_2$R$^a$,
 (d) —CN, and
 (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
  (i) halo,
  (ii) —OR$^a$,
  (iii) —C$_{1-6}$alkyl, which is optionally substituted with 1-6 halo, and
  (iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
 (a) halo,
 (b) —OR$^a$,
 (c) —C$_{1-6}$alkyl, which is optionally substituted with 1-6 halo,
 (d) —C$_{3-6}$cycloalkyl, which is optionally substituted with 1-6 halo
 (e) —CN, and
 (f) —CO$_2$R$^a$, and
(3) —C$_{3-6}$cycloalkyl, which is optionally substituted with 1-6 halo;

v is 0, 1, or 2.

In a class of the invention, $R^1$ is selected from hydrogen, —$C_{1-6}$ alkyl (which is optionally substituted with 1-7 substituents each independently selected from the group consisting of halo, hydroxy, —O—$C_{1-6}$ alkyl, and —$NR^bR^c$), halo, hydroxy, —O—$C_{1-6}$ alkyl (which is optionally substituted with 1-6 halo), —CN or —$NR^bR^c$. In a subclass of the invention, $R^1$ is selected from hydrogen or —$C_{1-6}$ alkyl, which is optionally substituted with 1-7 substituents each independently selected from the group consisting of halo, hydroxy, —O—$C_{1-6}$ alkyl and —$NR^bR^c$. In a further subclass of the invention, $R^1$ is hydrogen.

In a class of the invention, $R^{2a}$ and $R^{2b}$ are independently selected from the group consisting of: hydrogen, —$C_{1-6}$alkyl (which is optionally substituted with 1-7 substituents each independently selected from the group consisting of halo, hydroxy and —O—$C_{1-6}$ alkyl), halo, —$OR^a$, —CN and —$NR^bR^c$. In a subclass of the invention, $R^{2a}$ and $R^{2b}$ are independently selected from the group consisting of hydrogen, —$C_{1-6}$ alkyl (which is optionally substituted with 1-7 substituents each independently selected from the group consisting of: halo, hydroxy and —O—$C_1$-6alkyl), halo, —$OR^a$ and —$NR^bR^c$. In a further subclass of the invention, $R^{2a}$ and $R^{2b}$ are independently selected from the group consisting of hydrogen, halo, and —$NR^bR^c$. In a further subclass of the invention, $R^{2a}$ is hydrogen and $R^{2b}$ is $NH_2$. In another subclass of the invention, $R^{2a}$ and $R^{2b}$ are both hydrogen. In another subclass of the invention, $R^{2a}$ is hydrogen and $R^{2b}$ is F.

In a class of the invention, $R^3$ is selected from hydrogen, —$C_{1-6}$ alkyl (which is optionally substituted with 1-7 substituents each independently selected from the group consisting of halo, hydroxy and —O—$C_{1-6}$ alkyl), halo, —$OR^a$ or —CN. In a subclass of the invention, $R^3$ is selected from: hydrogen or —$C_{1-6}$ alkyl (which is optionally substituted with 1-7 substituents each independently selected from the group consisting of halo, hydroxy and —O—$C_{1-6}$alkyl). In a further subclass of the invention, $R^3$ is hydrogen.

In a class of the invention, $R^{4a}$ and $R^{4b}$ are independently selected from the group consisting of hydrogen, —$C_{1-6}$alkyl (which is optionally substituted with 1-7 substituents each independently selected from the group consisting of halo, hydroxy and —O—$C_{1-6}$ alkyl), halo, —$OR^a$, —CN and —$NR^bR^c$. In a subclass of the invention, and $R^{4b}$ are independently selected from the group consisting of hydrogen, —$C_{1-6}$ alkyl (which is optionally substituted with 1-7 substituents each independently selected from the group consisting of halo, hydroxy and —O—$C_{1-6}$alkyl), halo, —$OR^a$ and —$NR^bR^c$. In a further subclass of the invention, $R^{4a}$ and $R^{4b}$ are each hydrogen.

In a class of the invention $R^5$ is selected from hydrogen or —$C_{1-6}$ alkyl, which is optionally substituted with 1-7 substituents each independently selected from the group consisting of halo, hydroxy and —O—$C_{1-6}$ alkyl. In a subclass of the invention, $R^5$ is hydrogen.

In a class of the invention, $R^6$ is hydrogen.
In a class of the invention, $R^{7a}$ is hydrogen.
In a class of the invention, $R^{7b}$ is hydrogen.
In a class of the invention, $R^{7c}$ is hydrogen.

In a class of the invention, $R^8$ and $R^9$ are independently selected from the group consisting of hydrogen, —$C_{1-6}$alkyl (which is optionally substituted with 1-7 substituents each independently selected from the group consisting of halo, hydroxy and —O—$C_{1-6}$ alkyl), halo, —$OR^a$, —CN and —$NR^bR^c$. In a subclass of the invention, $R^8$ and $R^9$ are independently selected from the group consisting of hydrogen, —$C_{1-6}$ alkyl (which is optionally substituted with 1-7 substituents each independently selected from the group consisting of halo, hydroxy and —O—$C_{1-6}$alkyl), halo, —$OR^a$, and —$NR^bR^c$. In a further subclass of the invention $R^8$ and $R^9$ are independently selected from the group consisting of hydrogen and —$C_{1-6}$ alkyl. In a further subclass of the invention $R^8$ and $R^9$ are each hydrogen.

In a class of the invention $R^{10a}$ and $R^{10b}$ are each independently selected from the group consisting of:
(1) hydrogen,
(2) —$C_{1-4}$alkyl, which is optionally substituted with 1-5 substituents each independently selected from the group consisting of:
  (a) halo,
  (b) —$OR^a$,
  (c) —$C_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is optionally substituted with 1-3 substituents each independently selected from the group consisting of:
    (i) halo,
    (ii) —$OR^a$,
    (iii) —CN, and
    (iv) $C_{1-6}$alkyl, which is optionally substituted with 1-6 halo,
(3) halo,
(4) —$OR^a$ and
(5) —CN,
or $R^{10a}$ and $R^{10b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is optionally substituted with 1-5 substituents each independently selected from the group consisting of:
  (a) —$C_{1-6}$alkyl, which is optionally substituted with 1-3 substituents each independently selected from the group consisting of:
    (i) halo,
    (ii) —$OR^a$,
    (iii) —$CO_2R^a$,
    (iv) —$NR^bR^c$,
    (v) —$S(O)_vR^8$,
    (vi) —$C(=O)NR^bR^c$,
    (vii) —$N(R^b)CO_2R^a$, and
    (viii) —$N(R^b)SO_2R^d$,
  (b) halo,
  (c) —$S(O)_vR^8$,
  (d) —$OR^a$,
  (e) —CN,
  (f) —$C(=O)R^a$,
  (g) —$NR^bR^c$,
  (h) —$C(=O)NR^bR^c$,
  (i) —$CO_2R^a$,
  (j) —$(NR^b)CO_2R^a$,
  (k) —O—(C=O)—$NR^bR^c$,
  (l) —$(NR^b)$—(C=O)—$NR^bR^c$,
  (m) oxido,
  (n) oxo, and
  (o) —$(NR^b)SO_2R^d$.

In a subclass of the invention, $R^{10a}$ and $R^{10b}$ and the atom(s) to which they are attached join to form a ring selected from phenyl, pyridyl, and pyrimidinyl, which ring is optionally substituted with 1-3 substituents each independently selected from the group consisting of —C$_{1-6}$alkyl (which is optionally substituted with 1-3 substituents each independently selected from the group consisting of halo, —OR$^a$ and —NR$^b$R$^c$), halo, —OR$^a$, —CN, —NR$^b$R$^c$ and oxido. In a further subclass of the invention, R$^{10a}$ and R$^{10b}$ and the atom(s) to which they are attached join to form a ring selected from pyridyl, and pyrimidinyl, which ring is optionally substituted with 1-3 substituents each independently selected from the group consisting of —C$_{1-4}$alkyl (which is optionally substituted with 1-3 substituents each independently selected from the group consisting of halo, —OR$^a$ and —NR$^b$R$^c$), halo, and —CN. In a further subclass of the invention, and R$^{10a}$ and R$^{10b}$ and the atom(s) to which they are attached join to form a ring selected from pyridyl.

In a class of the invention, R$^a$ is selected from hydrogen or C$_{1-6}$alkyl, which is optionally substituted with 1-7 substituents each independently selected from the group consisting of halo, —O—C$_{1-6}$alkyl, which is optionally substituted with 1-6 halo, hydroxy and CN. In a subclass of the invention, R$^a$ is hydrogen In a class of the invention, R$^b$ and R$^c$ are independently selected from the group consisting of hydrogen and C$_{1-6}$alkyl, which is optionally substituted with 1-7 substituents each independently selected from the group consisting of halo, —OR$^a$ and CN. In a subclass of the invention, R$^b$ is hydrogen. In a subclass of the invention, R$^c$ is hydrogen.

In a class of the invention, R$^d$ is C$_{1-6}$alkyl, which is optionally substituted with 1-4 halo.

In a class of the invention, X is a bond, —O—, or —CR$^8$R$^9$—. In a subclass of the invention, X is a bond. In another subclass of the invention, X is —CR$^8$R$^9$—. In another subclass of the invention, X is —O—.

In a class of the invention, A$^5$ is a bond.
In a class of the invention, A$^6$ is —CR$^8$R$^9$—.
In a class of the invention, A$^7$ is a bond.
In a class of the invention, A$^8$ is —CR$^8$R$^9$—.

In a class of the invention, G$^1$ is —C(R$^{7a}$)=, G$^2$ is —C(R$^{7b}$)=, and G$^3$ is —N= or —(N$^+$—O$^-$)=. In another class of the invention G$^1$ is —C(R$^{7a}$)=, G$^2$ is —C(R$^{7b}$)=, G$^3$ is —C(R$^{7c}$)=.

In a class of the invention, Ar$^1$ is phenyl, which is optionally substituted with 1-5 substituents each independently selected from the group consisting of —C$_{1-6}$alkyl (which is optionally substituted with 1-6 halo), halo, hydroxy, —O—C$_{1-6}$ alkyl, which is optionally substituted with 1-6 halo and CN. In a subclass of the invention, Ar$^1$ is phenyl, which is optionally substituted with 1-5 halo. In another subclass of the invention, Ar$^1$ is phenyl. In another subclass of the invention, Ar$^1$ is phenyl which is substituted with 1-4 fluoro.

In a class of the invention, J is =C(R$^{10a}$)—.
In a class of the invention, J is —N(R$^b$)—.
In a class of the invention, Y is =C(R$^{16b}$)—.
In a class of the invention, Y is C(=O)—.

Reference to the preferred classes and subclasses set forth above is meant to include all combinations of particular and preferred groups unless stated otherwise.

Specific embodiments of the present invention include, but are not limited to:

(6S)—N-[(5S,6S,9R)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide;

(6S)—N-[(5S,6S,9S)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide;

(6S)—N-[(5R,6S,9R)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide;

(6S)—N-[(5R,6S,9S)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide;

(6S)-2'-Oxo-N-(6-phenyl-5,6,7,8-tetrahydroquinolin-8-yl)-1',2',5,7-tetrahydrospiro[cyclopenta[b]pyridine-6,3'-pyrrolo[2,3-b]pyridine]-3-carboxamide;

(S)—N-((6S,9S)-6-(2,3-Difluorophenyl)-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide;

(S)—N-((6R,9R)-6-(2,3-difluorophenyl)-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide;

(S)—N-((5R,6S,9R)-6-(2,3-Difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide;

(S)—N-((5S,6R,9S)-6-(2,3-difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide;

(3'S)-2'-Oxo-N-(6-phenyl-5,6,8,9-tetrahydrooxepino[4,5-b]pyridin-9-yl)-1',2',5,7-tetrahydrospiro[cyclopenta[b]pyridine-6,3'-pyrrolo[2,3-b]pyridine]-3-carboxamide;

or a pharmaceutically acceptable salt thereof

The invention also encompasses a pharmaceutical composition which comprises an inert carrier and the compound of Formula I, or a pharmaceutically acceptable salt thereof The invention also encompasses a method of treating headache in a mammalian patient in need of such treatment, which comprises administering to the patient a therapeutically effective amount of the compound of Formula I, or a pharmaceutically acceptable salt thereof. In a specific embodiment of the invention, the headache is migraine headache.

The invention also encompasses the use of a compound of Formula I, or a pharmaceutically acceptable salt thereof, and a pharmaceutically acceptable carrier, for the manufacture of a medicament for the treatment of headache. In a specific embodiment of the invention, the headache is migraine headache.

The invention is also directed to medicaments or pharmaceutical compositions for treating diseases or disorders in which CGRP is involved, such as migraine, which comprise a compound of Formula I, or a pharmaceutically acceptable salt thereof, and a pharmaceutically acceptable carrier.

The invention is also directed to the use of a compound of Formula I for treating diseases or disorders in which CGRP is involved, such as migraine.

The invention is further directed to a method for the manufacture of a medicament or a composition for treating diseases or disorders in which CGRP is involved, such as migraine, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH$_2$C(O)— groups (keto forms) may undergo tautomerism to form hydroxy —CH=C(OH)— groups (enol forms). Both keto and enol forms are included within the scope of the present invention.

When any variable (e.g. R$^8$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" should be understood as meaning that the group in question is either unsubstituted or may be substituted with one or more substituents.

As used herein, "alkyl" is intended to mean linear or branched structures having no carbon-to-carbon double or triple bonds. Thus, C$_{1-4}$ alkyl is defined to identify the group as having 1, 2, 3 or 4 carbons in a linear or branched arrangement, such that C$_{1-4}$ alkyl specifically includes, but is not limited to, methyl, ethyl, n-propyl, iso-propyl, n-butyl, iso-butyl and tert-butyl.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

As appreciated by those of skill in the art, "halo" or "halogen" as used herein is intended to include chloro (Cl), fluoro (F), bromo (Br) and iodo (I).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP receptor antagonists makes them useful pharmacological agents for disorders that involve CGRP in humans and animals, but particularly in humans.

The compounds of the present invention may have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; obesity; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPAKA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In an embodiment of the invention the present compounds may be used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or *acacia*; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum *acacia*; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum *acacia* or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 μL) was added and the radioactivity was counted on a Topcount (Packard Instrument). Data analysis was carried out by using Prism and the K$_i$ was determined by using the ChengPrusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 mg/mL streptomycin, and maintained at 37° C. and 95% humidity. Cells were subcultured by treatment with 0.25% trypsin with 0.1% EDTA in HBSS. Stable cell line generation was accomplished by co-transfecting 10 μg of DNA with 30 μg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 μg/mL hygromycin and 1 μg/mL puromycin) was added the following day. A clonal cell line was generated by single cell deposition utilizing a FACS Vantage SE (Becton Dickinson). Growth medium was adjusted to 150 μg/mL hygromycin and 0.5 μg/mL puromycin for cell propagation.

RECOMBINANT RECEPTOR BINDING ASSAY (Assay A): Cells expressing recombinant human CL receptor/RAMP1 were washed with PBS and harvested in harvest buffer containing 50 mM HEPES, 1 mM EDTA and Complete™ protease inhibitors (Roche). The cell suspension was disrupted with a laboratory homogenizer and centrifuged at 48,000 g to isolate membranes. The pellets were resuspended in harvest buffer plus 250 mM sucrose and stored at 70° C. For binding assays, 20 μg of membranes were incubated in 1 mL binding buffer (10 mM HEPES, pH 7.4, 5 mM $MgCl_2$, and 0.2% BSA) for 3 h at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4, and 5 mM $MgCl_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{(Y_{max} - Y_{min})(\% I_{max} - \% I_{min}/100) + Y_{min} + (Y_{max} - Y_{min})(100 - \% I_{max}/100)}{1 + ([Drug]/K_i(1 + [Radiolabel]/K_d)^{nH}}$$

Where Y is observed CPM bound, $Y_{max}$ is total bound counts, Y is non specific bound counts, ($Y_{max}-Y_{min}$) is specific bound counts, % $I_{max}$ is the maximum percent inhibition, % I min is the minimum percent inhibition, radiolabel is the probe, and the $K_d$ is the apparent dissociation constant for the radioligand for the receptor as determined by hot saturation experiments.

RECOMBINANT RECEPTOR FUNCTIONAL ASSAY (Assay B): Cells were resuspended in DMEM/F12 (Hyclone) supplemented with 1 g/L BSA and 300 μM isobutyl-methylxanthine. Cells were then plated in a 384-well plate (Proxiplate Plus 384; 509052761; Perkin-Elmer) at a density of 2,000 cells/well and incubated with antagonist for 30 min at 37° C. Human α-CGRP was then added to the cells at a final concentration of 1.2 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined RECOMBINANT RECEPTOR FUNCTIONAL ASSAY (Assay C): Cells were resuspended in DMEM/F12 (Hyclone) supplemented with 1 g/L BSA and 300 μM isobutyl-methylxanthine. Cells were then plated in a 384-well plate (Proxiplate Plus 384; 509052761; Perkin-Elmer) at a density of 3,500 cells/well and incubated with antagonist for 30 min at 37° C. Human α-CGRP was then added to the cells at a final concentration of 1 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined Representative $IC_{50}$ values in the recombinant receptor functional assays for exemplary compounds of the invention are provided in the table below:

| Example | Assay | $IC_{50}$ (nM) |
|---|---|---|
| 1 | B | 0.93 |
| 2 | B | 290 |
| 3 | B | 6.3 |
| 4 | B | 65 |
| 5 isomer A | B | 22 |
| 5 isomer B | B | 4600 |
| 6 isomer A | B | 78 |
| 6 isomer B | B | 150 |
| 7A | B | 380 |
| 7B | B | 4.5 |
| 8C | C | 22 |
| 8D | C | 570 |
| 9 isomer A | C | 1900 |
| 9 isomer B | C | 1100 |
| 9 isomer C | C | 1100 |
| 9 isomer D | C | 480 |

The following abbreviations are used throughout the text:
Me: methyl
Et: ethyl
t-Bu: tert-butyl
Bu: butyl
i-Pr: isopropyl
Ar: aryl
Ph: phenyl
Bn: benzyl
Py: pyridyl
Ac: acetylate
OAc: acetate
DCE: 1,2-dichloroethane
TFA: trifluoroacetic acid
TEA: triethylamine
Boc: tert-butoxycarbonyl
BOP: (benzotriazol-1-yloxy)tris(dimethylamino)phosphonium hexafluorophosphate
DIEA: N,N-diisopropylethylamine
HOBT: 1-hydroxybenzotriazole
EDC: N-(3-dimethylaminopropyl)-N'-ethylcarbodiimide hydrochloride
PyClU: chlorodipyrrolidinocarbenium
n-BuLi: n-butyllithium
n-HexLi n-hexyllithium
HATU: O-(7-azabenzotriazol-1-yl)-N,N,N'N'-tetramethyluronium hexafluorophosphate
EDTA: ethylenediaminetetraacetic acid
DMF: N,N-dimethylformamide
HMDS: hexamethyldisilazane
THF: tetrahydrofuran
DMSO: dimethylsulfoxide
SEM: 2-trimethylsilylethoxymethyl
SEMCl: 2-trimethylsilylethoxymethyl chloride
PBPB: pyridinium bromide perbromide
DMEM: Dulbecco's Modified Eagle Medium (High Glucose)
FBS: fetal bovine serum
BSA: bovine serum albumin
PBS: phosphate-buffered saline
HEPES: N-(2-hydroxyethyl)piperazine-N'-(2-ethanesulfonic acid)
SM: starting material
min minutes
h: hours
aq: aqueous
HPLC: high performance liquid chromatography
LCMS: liquid chromatography-mass spectrometry
SFC: supercritical fluid chromatography
NMP: 1-methyl-2-pyrrolidinone MTBE: methyl tert-butyl ether
DMA: N,N-dimethylacetamide
NBS: N-bromosuccinimide
CAN: ammonium cerium(IV) nitrate
dppf: 1,1'-bis(diphenylphosphino)ferrocene
dba: dibenzylideneacetone
BINAP: 2,2'-bis(diphenylphosphino)-1,1'-binaphthalene
Ms: methanesulfonyl
p-Ts: 4-toluenesulfonyl
trisyl: 2,4,6-triisopropylbenzenesulfonyl
DMAP: 4-(dimethylamino)pyridine
DMAC: N,N-dimethylacetamide
PMBCl: 4-methoxybenzyl chloride
DMPU: N,N'-dimethylpropyleneurea Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

REACTION SCHEMES

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

A synthetic route to the azaoxindole pyridine acid intermediate 1.4 is shown in Scheme 1. Diazotization of aminopyridine 1.1, whose preparation is described in WO 2008/020902, followed by treatment with potassium iodide provides iodide 1.2. Palladium-catalyzed carbonylation in methanol then affords ester 1.3, which may be saponified with sodium hydroxide to furnish 1.4.

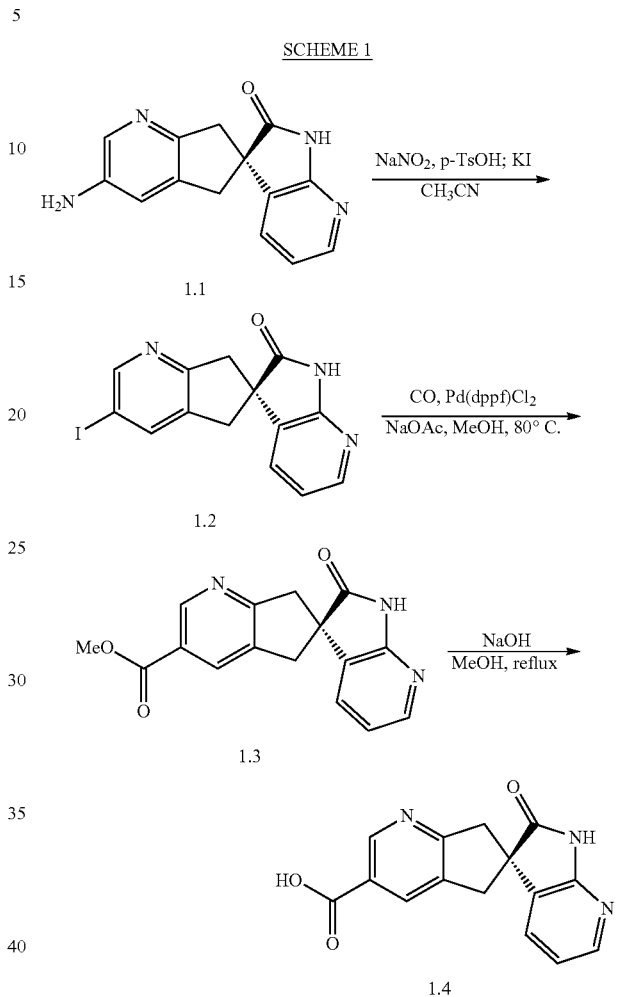

SCHEME 1

An alternative synthesis of the azaoxindole pyridine acid intermediate 1.4 is shown in Scheme 2. Esterification of diacid 2.1 followed by bromination provides 2.2. Reduction with sodium borohydride then furnishes diol 2.3. Alkylation of the protected azaoxindole 2.4 with the dimesylate produced from 2.3 affords the spirocycle 2.5. Palladium-catalyzed carbonylation in methanol followed by chiral resolution gives ester 2.6 as a single enantiomer. Removal of the SEM protecting group under acidic conditions and hydrolysis of the ester using sodium hydroxide then provides 1.4.

SCHEME 2

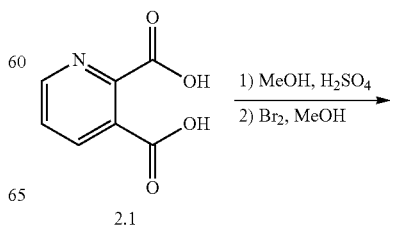

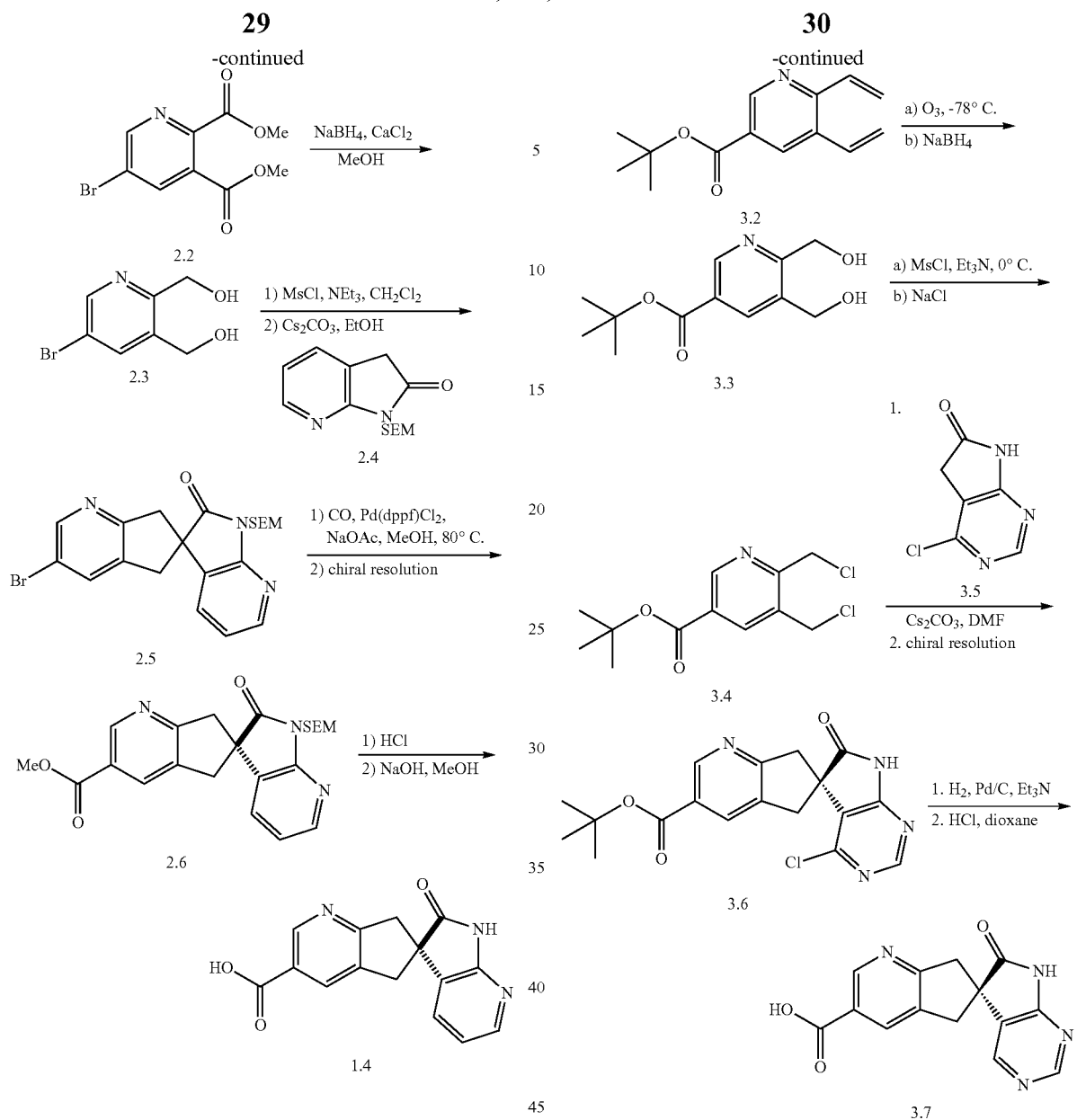

A synthetic route to diazaoxindole carboxylic acid intermediate 3.7 is shown in Scheme 3. Esterification of acid 3.1 is followed by vinylation under palladium catalysis to afford divinyl pyridine 3.2. Ozonolysis with a borohydride reductive workup then yields diol 3.3. After mesylation and treatment with sodium chloride, the resulting dichloro intermediate 3.4 can be alkylated with oxindole 3.5 under basic conditions to give spirocycle 3.6, following chiral resolution of the enantiomers. Dechlorination under buffered hydrogenation conditions and acidic deprotection affords acid 3.7.

SCHEME 3

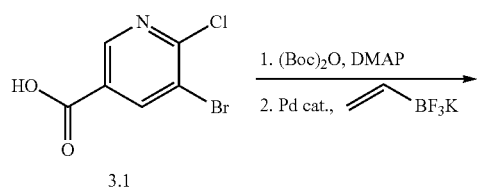

Useful derivatives of the intermediates described herein may be prepared using well-precedented methodology. Two examples are illustrated in Scheme 4, in which the azaoxindole intermediate 1.4 is converted to the corresponding nitrile derivative 4.2 and fluoro derivative 4.6, which may both be used to prepare compounds of the present invention. Bromination of 1.4 with N-bromosuccinimide in boron trifluoride dihydrate provides the bromo derivative 4.1, which may be converted to the desired nitrile 4.2 using zinc cyanide and a palladium catalyst as shown. Alternatively, bromide 4.1 may be diprotected under standard conditions to provide ester 4.3, and this may be converted to the corresponding tributylstannane analogue 4.4 using bis(tributyltin) and a palladium catalyst. The tributylstannane derivative 4.4 may be converted to fluoride 10.5 under silver-catalyzed conditions described by Ritter and colleagues (Tang et al. (2010) *J. Am. Chem. Soc.* 132, 12150-12154) utilizing Selectfluor® [N-chloromethyl-N'-fluorotriethylenediammonium bis(tetrafluoroborate)]. Finally, removal of the SEM protecting group and saponification provides the desired fluoroazaoxindole 4.6.

SCHEME 4

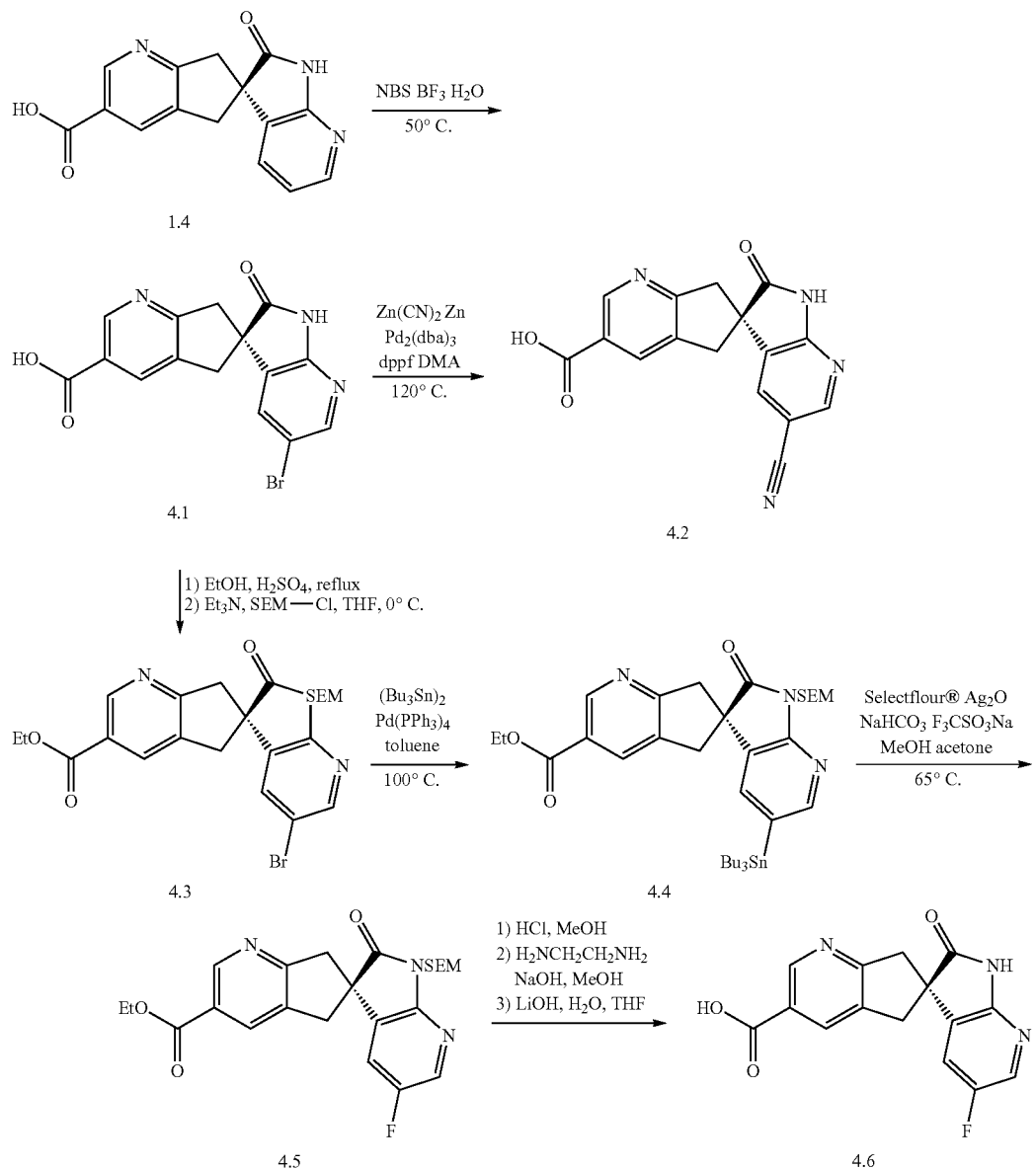

A synthetic route to the azaoxindole indane acid intermediate 5.17 is shown in Scheme 5. Esterification of diacid 5.1 followed by hydrogenation using palladium on carbon as a catalyst provides aniline 5.2. Dibenzylation under basic conditions with heat affords 5.3, and reduction of the diester with LiAlH$_4$ furnishes diol 5.4. Chlorination with thionyl chloride provides benzyl chloride 5.5. Palladium-catalyzed amination of bromide 5.6 with tert-butylamine gives 5.7. Sequential treatment with n-hexyllithium and methyl chloroformate (2×) affords azaoxindole ester 5.8. Alkylation with the benzyl-chloride 5.5 under basic conditions in the presence of the cinchonidine-derived catalyst 5.12 (prepared via the alkylation of cinchonidine 5.10 with benzyl bromide 5.11) affords spirocycle 5.13. Deprotection of the azaoxindole using methanesulfonic acid with heat and debenzylation under standard hydrogenation conditions provides aniline 5.14. Diazotization followed by treatment with potassium iodide provides iodide 5.15. Palladium-catalyzed carbonylation in methanol then affords ester 5.16, which may be saponified with sodium hydroxide to furnish 5.17.

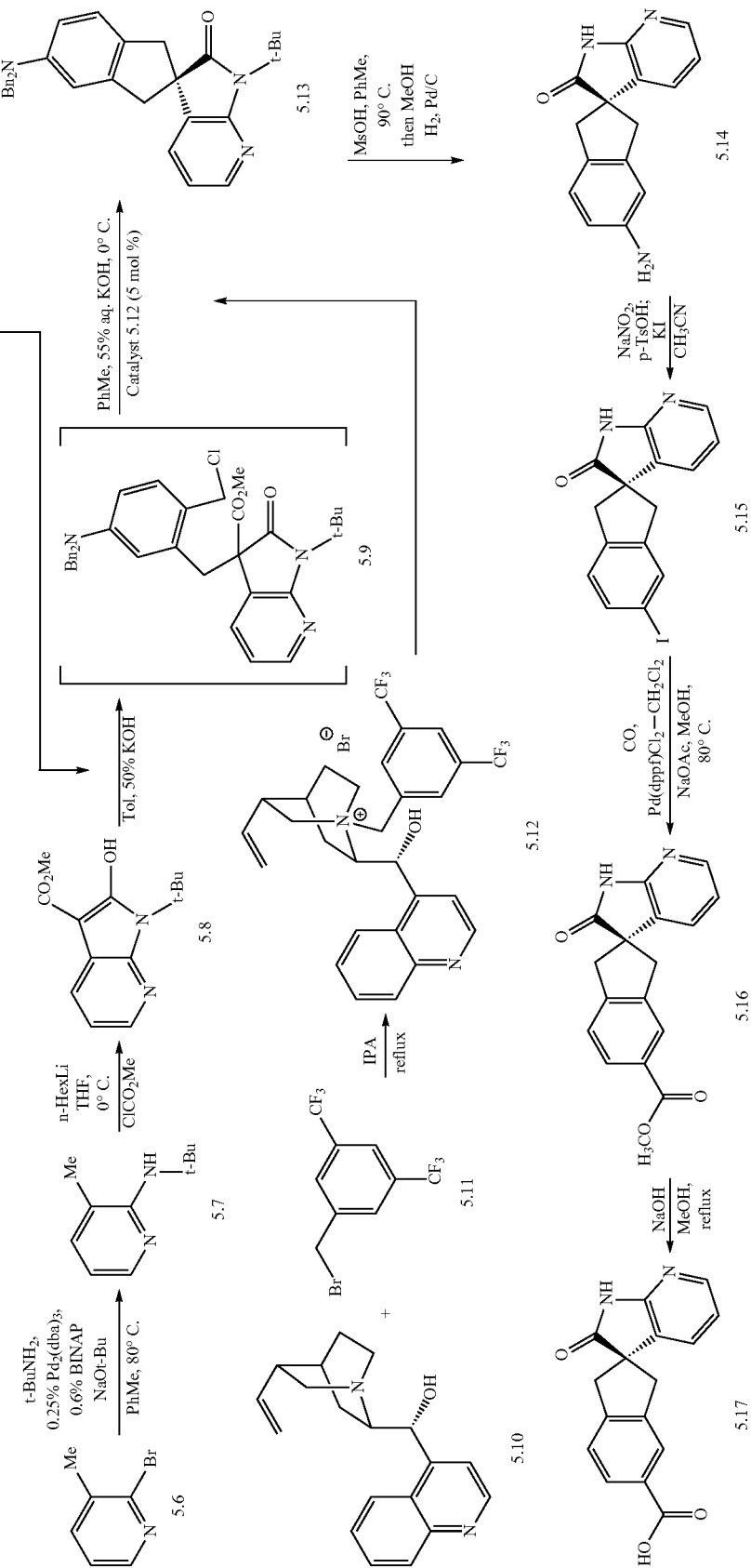
SCHEME 5

An alternative synthesis of the azaoxindole pyridine acid intermediate 5.17 is shown in Scheme 6. Alkylation of the azaoxindole ester 5.8 with dibenzyl bromide 6.1 followed by chiral resolution of the enantiomers provides ester 6.2. Sequential deprotection of the azaoxindole using methanesulfonic acid with heat and hydrolysis of the ester provides 5.17.

SCHEME 6

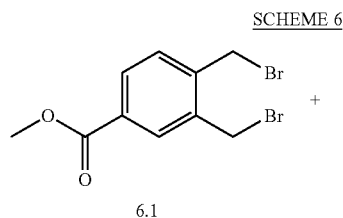

6.1

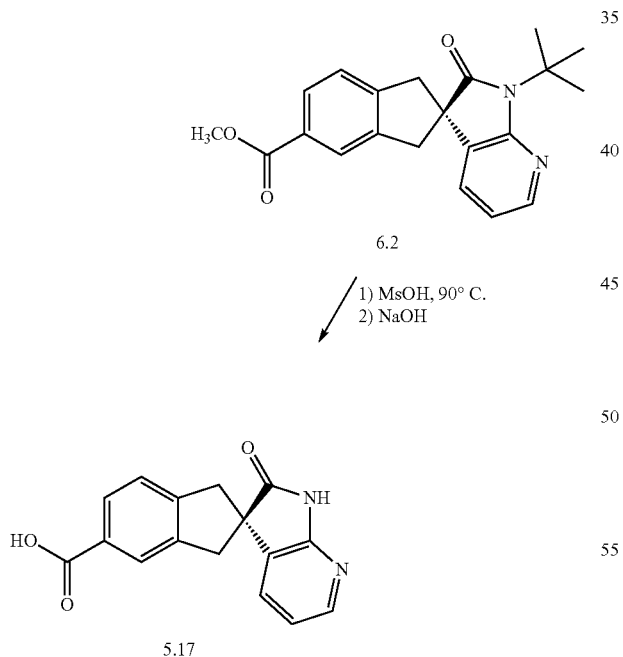

A synthetic route to the diazaoxindole carboxylic acid intermediate 7.4 is shown in Scheme 7. Alkylation of dibromide 6.1 with oxindole 7.1 under basic conditions and subsequent chiral resolution affords spirocycle 7.2. Dechlorination under buffered hydrogenation conditions and ester hydrolysis then affords acid 7.4.

SCHEME 7

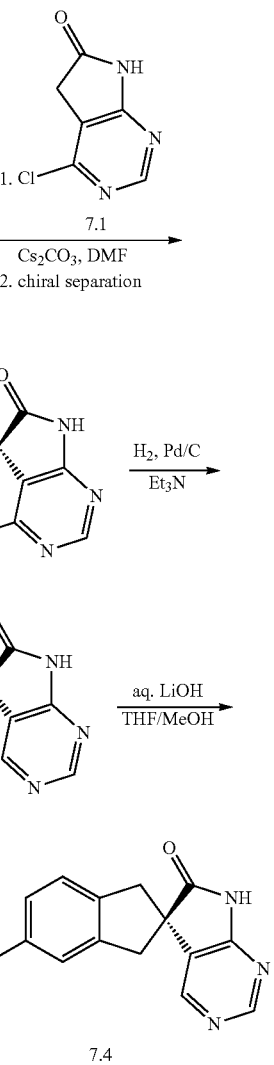

Other useful derivatives of the intermediates described herein may be prepared using known methodology. One such example is illustrated in Scheme 8, in which the azaoxindole intermediate 5.17 is converted to the corresponding nitrile derivative 8.2, which may be used to prepare compounds of the present invention. Treatment of 5.17 with bromine in acetic acid provides the bromo derivative 8.1, which may be converted to the desired nitrile 8.2 using zinc cyanide and a palladium catalyst as shown.

SCHEME 8

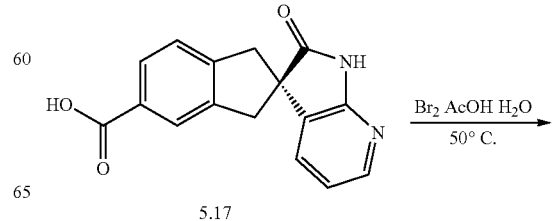

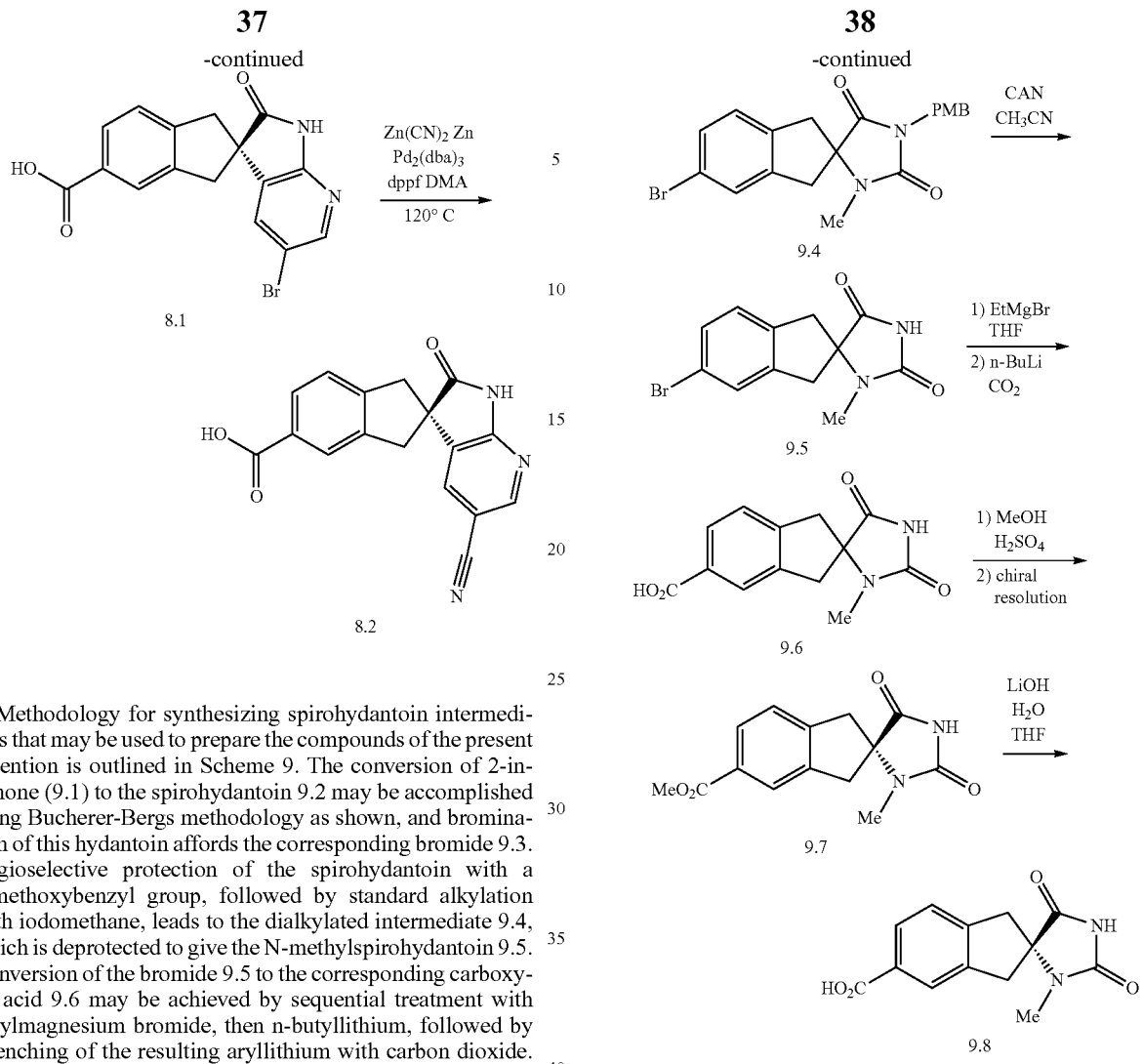

Methodology for synthesizing spirohydantoin intermediates that may be used to prepare the compounds of the present invention is outlined in Scheme 9. The conversion of 2-indanone (9.1) to the spirohydantoin 9.2 may be accomplished using Bucherer-Bergs methodology as shown, and bromination of this hydantoin affords the corresponding bromide 9.3. Regioselective protection of the spirohydantoin with a 4-methoxybenzyl group, followed by standard alkylation with iodomethane, leads to the dialkylated intermediate 9.4, which is deprotected to give the N-methylspirohydantoin 9.5. Conversion of the bromide 9.5 to the corresponding carboxylic acid 9.6 may be achieved by sequential treatment with ethylmagnesium bromide, then n-butyllithium, followed by quenching of the resulting aryllithium with carbon dioxide. The acid 9.6 may be esterified under standard conditions, subjected to chiral resolution using HPLC or SFC, and the (S)-enantiomer 9.7 can be saponified to give the corresponding acid 9.8 as shown.

SCHEME 9

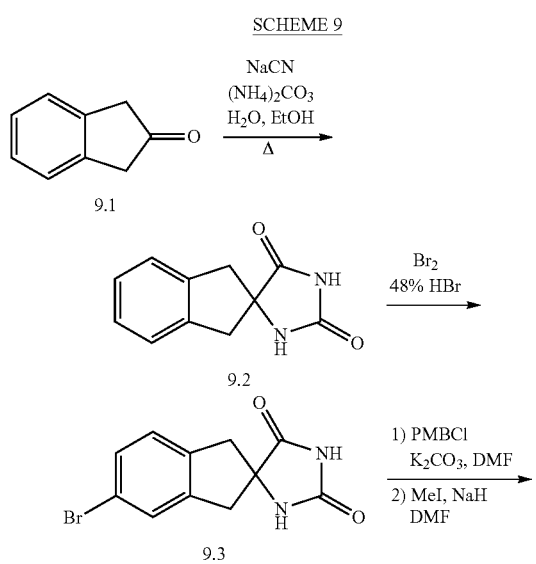

Methodology for synthesizing spirohydantoin intermediates that may be used to prepare the compounds of the present invention is outlined in Scheme 10. Following a one-pot esterification-bromination of pyridine-2,3-dicarboxylic acid (10.1), reduction of the resulting diester 10.2 affords diol 10.3. The imide functionality of 1-methylhydantoin (10.4) may be protected, for example with a 4-methoxybenzyl group, to give a 1,3-dialkylated hydantoin such as 10.5. Other protecting groups may also be employed as alternatives to 4-methoxybenzyl. Diol 10.3 can be converted to the corresponding dichloride 10.6 using thionyl chloride, and 10.6 may be reacted with hydantoin 10.5 using sodium hydride as base to provide the spirohydantoin intermediate 10.7. Bromide 10.7 can be converted to the corresponding methyl ester 10.8 via palladium-catalyzed carbonylation as shown, and deprotection followed by saponification affords the racemic carboxylic acid 10.10. This route may be modified to provide the individual enantiomers of acid 10.10. For example, the racemic ester 10.8 may be separated using chiral SFC to provide (R)-10.8 and (S)-10.8, and these individual enantiomers may be deprotected in analogy with Scheme 10 to provide 10.10 as its individual enantiomers.

SCHEME 10

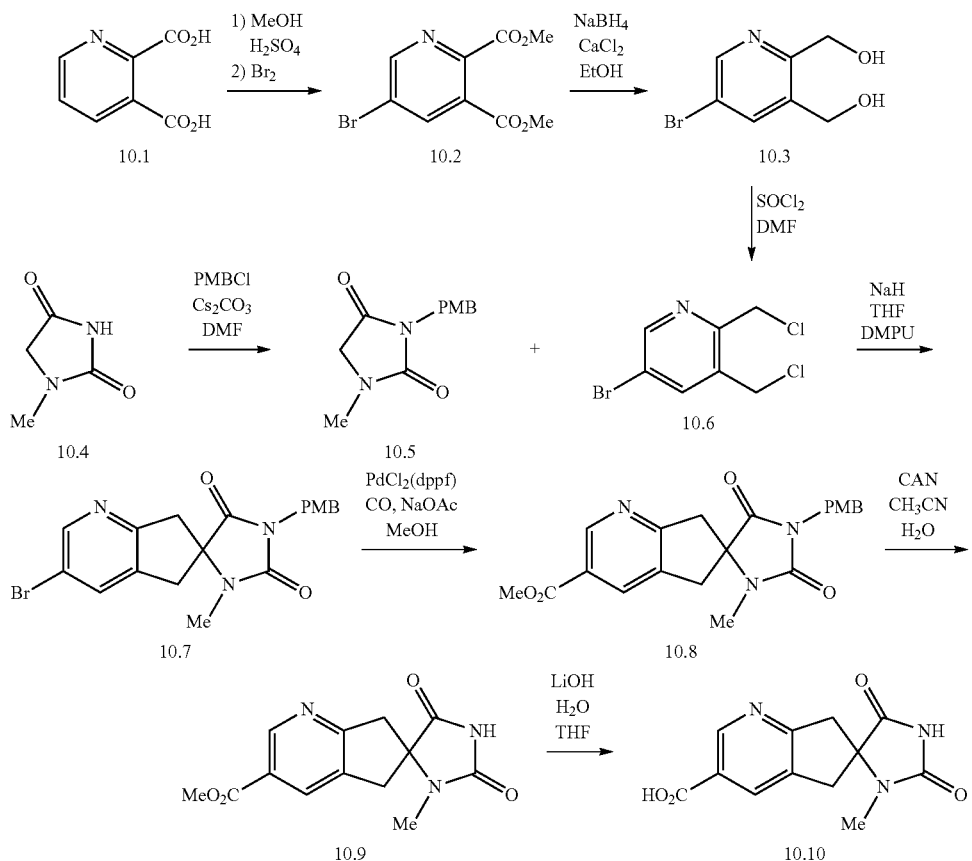

Other useful intermediates for preparing the compounds of the present invention have been described previously or may be synthesized by applying well-precedented methodology to known compounds. For example, in Scheme 11 the known alcohol 11.1 (described in WO 2011/046997) is oxidized under Swern conditions to afford ketone 11.2. Reductive amination of this ketone using excess ammonium acetate may be used to provide the amine 11.3 as the major product along with smaller amounts of other stereoisomers Amines such as 11.3 may be coupled with carboxylic acids such as those described in Schemes 1-10 to provide amide compounds of interest, and the azido group may be subsequently reduced to an amino group to provide other compounds of the present invention.

SCHEME 11

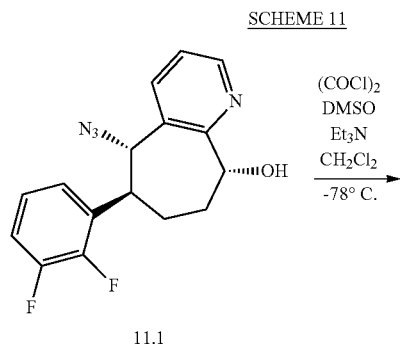

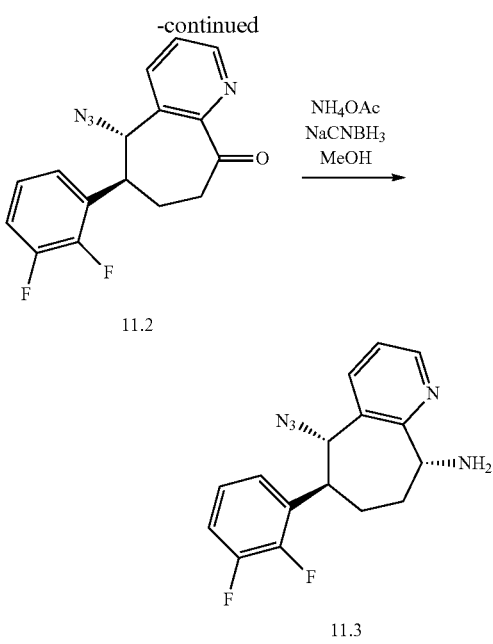

The synthesis of some tetrahydroquinoline intermediates that may also be used to synthesize compounds of the present invention is detailed in Scheme 12. As described in the literature (Koltunov & Repinskaya (2002) *Russ. J. Org. Chem.* 38, 437-442), under strongly acidic conditions benzene can react with 8-hydroxyquinoline (12.1) to provide the tetrahydroquinolin-8-one 12.2 in good yield. Ketone 12.2 may be reductively aminated and the amine product protected to provide the cis and trans carbamate products 12.3 and 12.4, which may be separated by chromatography. Deprotection of these carbamates under acidic conditions can provide the key intermediates cis-amine 12.5 and trans-amine 12.6.

are useful to preparing the compounds of the present invention. Swern oxidation of alcohol 13.1, whose preparation is described in the literature (Leahy, D. K et al *Org. Lett.* 2012, 14, 4938-4941), and reductive amination of the product ketone 13.2 with ammonium acetate provides 13.3 as a mixture of cis and trans isomers.

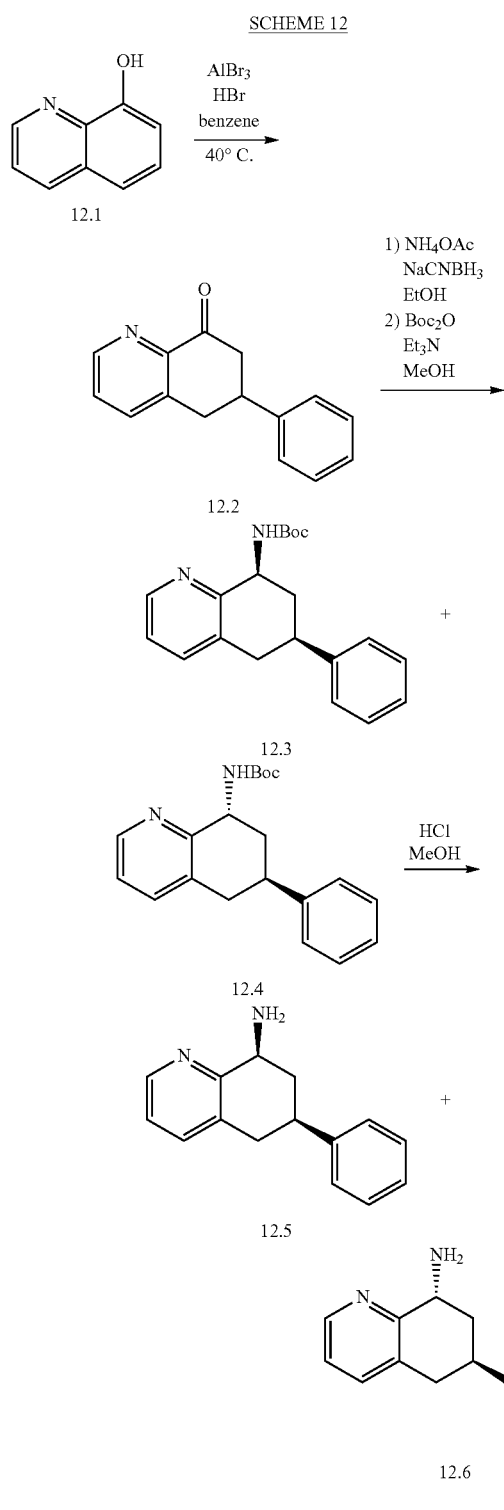

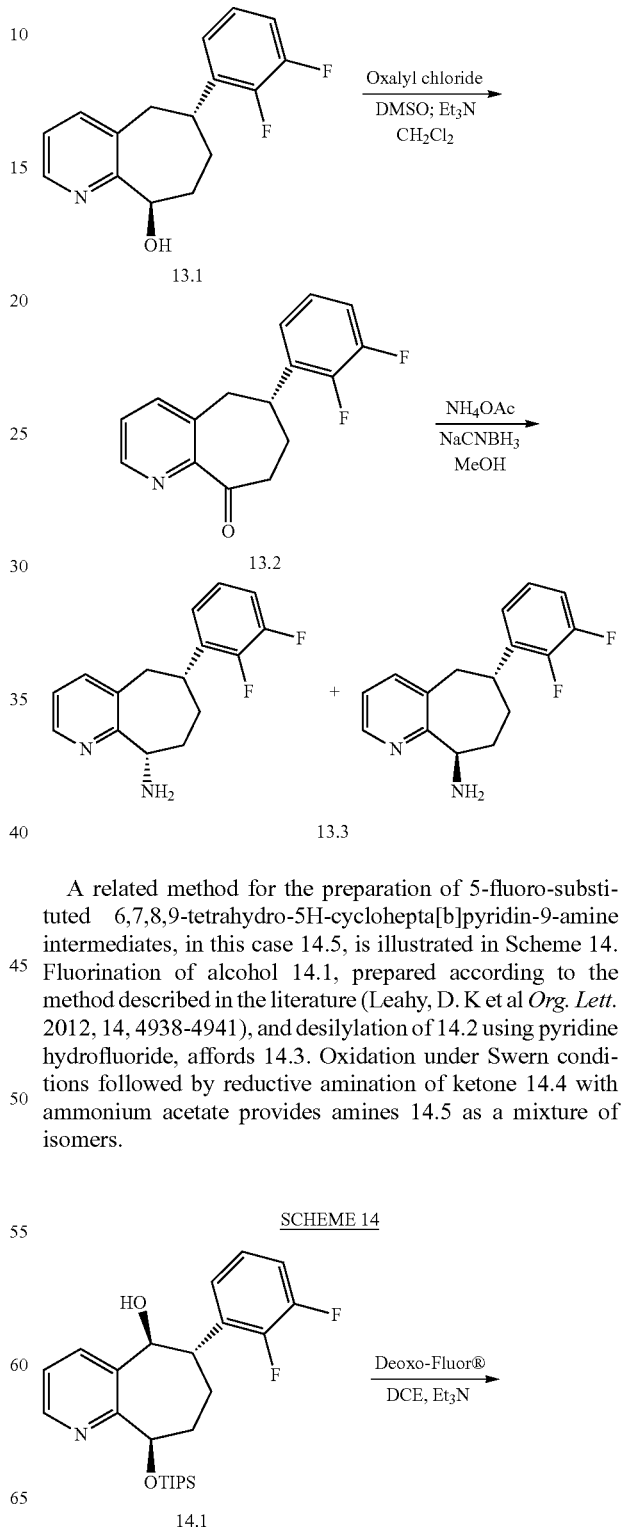

A related method for the preparation of 5-fluoro-substituted 6,7,8,9-tetrahydro-5H-cyclohepta[b]pyridin-9-amine intermediates, in this case 14.5, is illustrated in Scheme 14. Fluorination of alcohol 14.1, prepared according to the method described in the literature (Leahy, D. K et al *Org. Lett.* 2012, 14, 4938-4941), and desilylation of 14.2 using pyridine hydrofluoride, affords 14.3. Oxidation under Swern conditions followed by reductive amination of ketone 14.4 with ammonium acetate provides amines 14.5 as a mixture of isomers.

Scheme 13 depicts a synthetic route to 6,7,8,9-tetrahydro-5H-cyclohepta[b]pyridin-9-amine intermediates 13.3 which

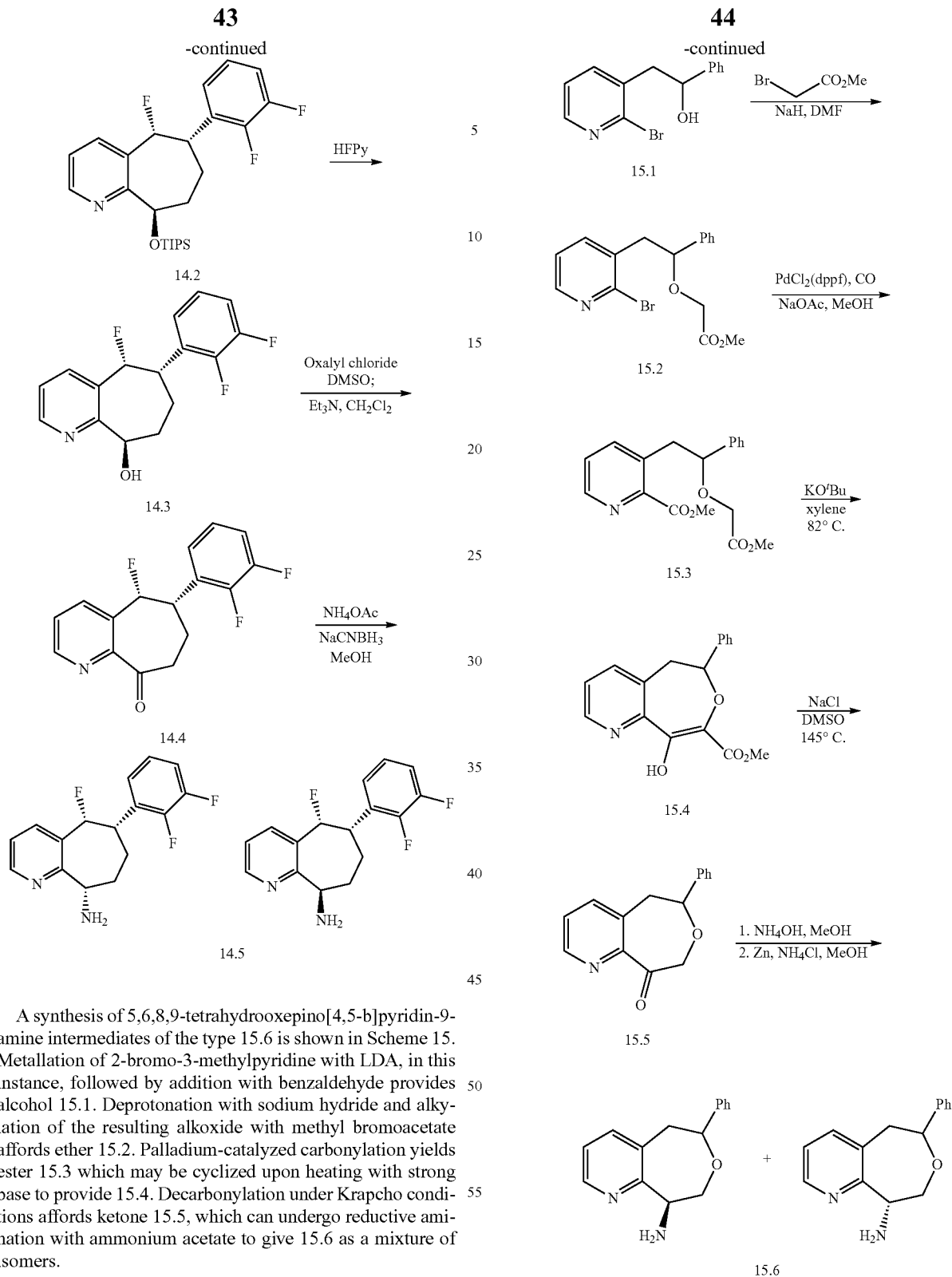

A synthesis of 5,6,8,9-tetrahydrooxepino[4,5-b]pyridin-9-amine intermediates of the type 15.6 is shown in Scheme 15. Metallation of 2-bromo-3-methylpyridine with LDA, in this instance, followed by addition with benzaldehyde provides alcohol 15.1. Deprotonation with sodium hydride and alkylation of the resulting alkoxide with methyl bromoacetate affords ether 15.2. Palladium-catalyzed carbonylation yields ester 15.3 which may be cyclized upon heating with strong base to provide 15.4. Decarbonylation under Krapcho conditions affords ketone 15.5, which can undergo reductive amination with ammonium acetate to give 15.6 as a mixture of isomers.

Scheme 16 illustrates conditions that can be used for the coupling of amine intermediates, for example 16.1, and carboxylic acid intermediates, such as 16.2, to produce, in this instance, amides 16.3. These standard coupling conditions are representative of the methods used to prepare the compounds of the present invention.

SCHEME 16

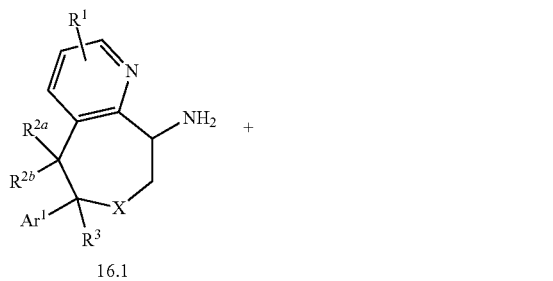

16.1

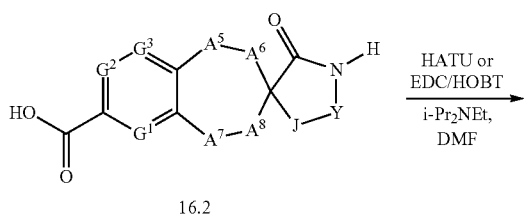

16.2

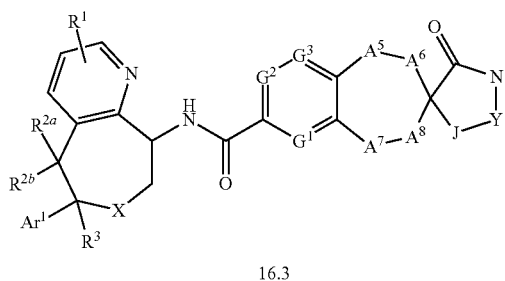

16.3

In some cases, alternative coupling conditions may be used to prepare the compounds of the present invention. In some cases, various protecting group strategies familiar to one skilled in the art of organic synthesis may be employed to allow preparation of a particular compound of the present invention.

It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

INTERMEDIATE 1

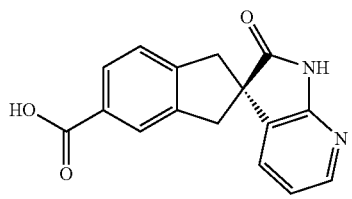 [SMILES: O=C(O)c1ccc2c(c1)C[C@@]1(C2)C(=O)Nc2ncccc21]

(2R)-2'-Oxo-1,1',2',3-tetrahydrospiro[indene-2,3'-pyrrolo[2,3-b]pyridine]-5-carboxylic acid The title compound can be prepared by either Method I or Method II as described below.

Method I:

Step A: Dimethyl 4-aminobenzene-1,2-dicarboxylate

| Materials | FW | Mass | Volume | mol | Equiv. | d (g/mL) |
|---|---|---|---|---|---|---|
| 4-nitro-phthalic acid | 211.13 | 5.3 kg | | 25.1 | 1 | |
| MsOH | 96 | 3.62 kg | 2.45 L | 37.7 | 1.5 | 1.48 |
| MeOH | | | 26 L | | | |
| 10% Pd/C (wet) | | 159 g | | | | |
| K$_3$PO$_4$ | 212 | 8.0 kg | | 37.7 | 1.5 | |
| EtOAc | | | 27 L | | | |

4-Nitrophthalic acid was dissolved in 26 L MeOH (slightly endothermic) and 3.62 kg of methanesulfonic acid (MsOH, exothermic). The solution was heated under nitrogen at 80° C. in the hydrogenation vessel for 16 h (if preferred, the reaction can also be carried out at reflux in a regular vessel). The solution was cooled to 40° C. and sampled to ensure <6% of remaining monomethyl ester.

The solution was further cooled to 20° C. and seeded (seeds can be readily prepared by taking out ca. 500 mL of the solution and stirred at 23° C. with traces of seeds that form on simple evaporation on a spatula) to form a very thick slurry.

10% PdC was charged with ca. 1 L MeOH and the slurry at 23° C. was carefully stirred under 60 psi of H$_2$ gas to maintain temp<40° C.

After complete reduction of the nitro group, the mixture became a solution containing the catalyst. An additional 16 L of MeOH was added to the mixture to ensure product stays in solution (without this, some product crystallized out after 3 days); if the vessel volume permits, this 16 L of MeOH can be added at the beginning of the reaction to dilute the exotherm of the hydrogenation.

The reaction was repeated at the same scale. The two batches were combined and the catalyst was filtered off with MeOH rinse. The filtrate was concentrated to 25 L to give a slurry. EtOAc (44 L) was added followed by a slow addition of aq K$_3$PO$_4$ (made from 16 kg solid+32 L water, solution ca. 36 L, used all but 1 L) to keep temp<25° C. The mixture became very thick after 2-4 L addition, but then lightened.

The pH of the mixture should be about 9 (otherwise adjust with more $K_3PO_4$ or 1 N HCl). The bottom aqueous layer (ca. 50 L, 0.3% loss) was cut away. The organic layer was washed with 32 L water (aq loss ca 2%), concentrated, solvent switched to toluene to a target volume of ca. 36 L with <4 L EtOAc left. Seed if necessary to induce crystallization. Heptane (20 L) was then added. The slurry was aged at 23° C. for >2 h when LC revealed <3% loss in the mother liquor. The crystals were collected by filtration and rinsing with 1/1 toluene/heptane (18 L) and then heptane (6 L), and dried to give the title product.

Step B: Dimethyl 4-(dibenzylamino)benzene-1,2-dicarboxylate

| Materials | FW | Mass | Volume | mol | Equiv. | d (g/mL) |
|---|---|---|---|---|---|---|
| dimethyl 4-aminobenzene-1,2-dicarboxylate | 209.20 | 4.33 kg | | 20.7 | 1 | |
| BnCl | 126.58 | 6.55 kg | 6.01 L | 51.7 | 2.5 | 1.09 |
| $K_2CO_3$ | 138.21 | 7.72 kg | | 55.9 | 2.7 | |
| KI | 166.00 | 687 g | | 4.14 | 0.2 | |
| DMAC | | | 21.6 L | | | |

A 100-L, four-necked, round-bottomed flask was charged with the dimethyl 4-aminobenzene-1,2-dicarboxylate, $K_2CO_3$, KI (anhydrous), and 21.6 L of N,N-dimethylacetamide (DMAC, 200 ppm of water; however, the reaction can tolerate more water). Benzyl chloride (BnCl) was added in one portion, and the reaction mixture (brown slurry) was heated to 60° C. over 20 min using a steam bath. The steam bath was then shutoff, and the reaction temperature continued to increase to 76.8° C. over the next 30 min (exotherm). After cooling to 75° C., the reaction mixture was stirred at this temperature for 2 h and then stirred at 90° C. until <1.5% of the monobenzyl intermediate remained (ca. 8-12 h) (yellow/white slurry). [note, the reaction mixture gets very thick during the reaction]. The steam bath was turned off and the reaction mixture was allowed to cool to room temperature (18° C.), then diluted with 21.6 L (5 volumes) of methyl t-butyl ether (MTBE) and 43.2 L (10 volumes) of water. The resulting organic layer was separated, washed with water (2×28 L), and concentrated to ca. 18 L (ca. 3 volumes). The brown oil was then solvent-switched to THF (60 L) and concentrated to ca. 38 L (<1000 ppm water). The product mixture containing the title compound was used in the next step without further purification.

Step C: [4-(Dibenzylamino)benzene-1,2-diyl]dimethanol

| Materials | FW | Mass | Volume | mol | Equiv. |
|---|---|---|---|---|---|
| dimethyl 4-(dibenzylamino)benzene-1,2-dicarboxylate | 389.44 | 8.06 kg | | 20.7 | 1.0 |
| $LiAlH_4$ | 1.0M | | 27.2 L | 27.2 | 1.3 |
| THF | | | 38 L | | |

A 100-L, four-necked, round-bottomed flask was charged with dimethyl 4-(dibenzylamino)benzene-1,2-dicarboxylate in 38 L of THF from the previous step. While cooling with a dry ice-acetone bath (ca. −50° C.), a solution of lithium aluminum hydride ($LiAlH_4$) in THF (1.0 M, 26 L) was added dropwise via an addition funnel keeping the internal temperature<5° C. (ca. 1.5 h addition). The resulting reaction mixture was aged at −12 to 1° C. for 3 h. Additional $LiAlH_4$ (1.2 L) was added via addition funnel and the reaction mixture was allowed to slowly warm to room temperature over 16 h. A solution of aqueous THF (1.03 L of water diluted with 4 L of THF) was then added slowly keeping the internal temperature<15° C. Next, 1.03 L of a 15% NaOH solution were added in one portion followed by the addition of 3.1 L of water in 5 portions. [note, the reaction mixture gets extremely thick during the second water addition step] The reaction mixture was allowed to warm to room temperature, and then filtered through Solka-Floc® with the aid of 40 L of THF [note, the filtration is slow, ca. 5 h] and concentrated to ca. 21 L (ca. 3 volumes). Toluene (56 L, 8 volumes) was added and the solution was concentrated to ca. 35 L (ca. 5 volumes). Seed crystals were then added to initiate crystallization and the reaction mixture was further concentrated to ca. 28 L (4 volumes). Heptane (70 L) was then added over 90 min and the crystallization was aged at room temperature until <3% of the diol remained in the mother liquor (ca. 3 h). The crystals were collected by filtration, washed with 20 L of a 1:2 toluene: heptane solution and 30 L of heptane, and dried under vacuum with a nitrogen sweep to give the title compound.

Step D: [2-(Chloromethyl)-4-(dibenzylamino)phenyl]methanol

| Materials | FW | Mass | Volume | mol | Equiv. | d (g/mL) |
|---|---|---|---|---|---|---|
| [4-(dibenzylamino)benzene-1,2-diyl]dimethanol | 333.42 | 6.00 kg | | 18.0 | 1.0 | |
| $SOCl_2$ | 118.97 | 6.42 kg | 3.94 L | 54.0 | 3.0 | 1.63 |
| $CH_3CN$ | | | 18.0 L | | | |

A 100-L, four-necked, round-bottomed flask was charged with $SOCl_2$ and 18 L of $CH_3CN$. While cooling with an ice-water bath (ca. 5° C.), [4-(dibenzylamino)benzene-1,2-diyl]dimethanol was added in portions over 1.5 h keeping the internal temperature<18° C. [note, excessive $HCl/SO_2$ gas, recommend using a HCl scrubber].

After the addition, the reaction mixture was warmed to 23° C. and diluted with 36 L (ca. 6 vol.) of methyl t-butyl ether (MTBE). The reaction mixture was seeded to initiate crystallization and then diluted with an additional 18 L of MTBE and aged at 23° C. for ca. 2 h (usually <5% chloride in the mother liquor). The crystals were collected by filtration, washed with 50 L of MTBE (to ensure the complete removal of HCl), and dried under vacuum with a nitrogen sweep to give the title compound as a hydrochloride salt.

Step A 1: N-tert-Butyl-3-methylpyridin-2-amine

| Material | FW | Equivalents | mol | Amount |
|---|---|---|---|---|
| 2-Bromo 3-methyl-pyridine, 98% | 172.02 | 1 | 28.3 | 4.97 kg |
| t-Butylamine, 99% | 73.14 | 1.5 | 42.7 | 4.51 L |
| Sodium t-butoxide | 96.10 | 2.0 | 56.5 | 5.60 kg |
| BINAP | 622.67 | 0.006 | 0.171 | 106 g |

| Material | FW | Equivalents | mol | Amount |
|---|---|---|---|---|
| $Pd_2(dba)_3$ | 915.72 | 0.0025 | 0.071 | 65 g |
| Toluene | | | | 50 L |
| Water | | | | 40 L |
| HCl, 2.0N | | | | ~24 L |
| NaOH, 10N | | | | 4.6 L |
| MTBE | | | | 50 L |

To a 3 or 4-necked flask (100 L) with water cooling condenser, mechanical stirring and $N_2$ was charged toluene (40 L), 2-bromo-3-methyl pyridine (4.966 kg), sodium t-butoxide (5.60 kg). The slurry was then sparged $N_2$ for 10 min; then tris(dibenzylideneacetone)dipalladium (0) ($Pd_2(dba)_3$, 0.065 kg, 0.071 mol), 2,2'-bis(diphenylphosphino)-1,1'-binaphthalene (BINAP, 0.106 kg, 0.171 mol) and t-butylamine (4.51 L) were charged. The resulting dark mixture was stirred 10 min at 23° C. under $N_2$ and then heated to 70° C. (internal temp) with a steam bath. No t-butyl amine reflux was noticed.

At 70° C., the heating was stopped, however the reaction temp rose to 83° C. in a few minutes due to exotherm and an ice-water bath was immediately applied to cool the reaction (very minor refluxing of solvent observed). The reaction temp rose to 90° C. and stayed at that temp for 10 min before dropping.

When the temperature decreased to 86° C., the ice-water bath was removed; the reaction was assayed and found to be complete (30 minutes after heating was stopped). The reaction mixture was then cooled with an ice bath and became extremely thick and difficult to stir upon reaching 46° C.; ~35 L water was added to quench the reaction (ice-bath was sufficient to maintain temp during quench). (The mixture was stable overnight at 23° C.).

The mixture was transferred to a 100 L extractor for separation. The aqueous layer (35 L) was cut, and the organic layer (50 L) was treated with HCl (2.0 N, ~24 L) to pH 0.45.

Layers were separated (50 L organic waste); the aqueous layer was collected and transferred back to the extractor. 50 L of methyl t-butyl ether (MTBE) was charged and the pH was adjusted to 9.3 (suggest range: 8.5 to 10) with NaOH (10 N, ~4.6 L. The aqueous layer was cut (2% loss by LC); the organic layer was washed with water (10 L), and transferred to 100 L flask with in-line filtration. The batch was concentrated and then flushed with THF to remove MTBE and water (water<150 ppm) to give the title compound in THF.

Step A2: Methyl 1-tert-butyl-2-hydroxy-1H-pyrrolo[2,3-b]pyridine-3-carboxylate

| Material | FW | Equiv | mol | Amount |
|---|---|---|---|---|
| Part 1: | | | | |
| N-tert-butyl-3-methylpyridin-2-amine | 164.25 | 1 | 26.36 | 4.33 kg |
| n-Hexyl Lithium | @ 2.09M/hexane | 1.0 | 26.36 | 12.60 L |
| Methyl chloroformate, 98% | 94.50/d1.228 | 1.04 | 26.36 | 2.13 L |
| THF | | | | 28 + 6 L |
| Part 2: | | | | |
| n-Hexyllithium | @ 2.09M | 0.7 | 18.45 | 9.10 L |
| Diisopropylamine, 99% | 101.2/d0.716 | 1.4 | 36.90 | 5.27 L |
| n-Hexyllithium | @ 2.09M | 1.6 | 39.54 | 20.9 L |
| Part 3: | | | | |
| Methyl Chloroformate, 98% | 94.5/d1.228 | 1.3 | 34.27 | 2.66 L |
| Work-up: | | | | |
| HCl, 5.0N | | | | 14.5 L |
| KOH, 4.0N | | | | 4 L |
| $K_2CO_3$, 22% (made from $K_2CO_3$ 99%) | | | | 12.6 L |

Part 1:

To a 4-necked RB flask (100 L) was charged a solution of N-tert-butyl-3-methylpyridin-2-amine (~28 L, 17.5% wt, 24.7 Kg, 23.36 mol) under $N_2$ and extra THF (6 L). This solution was cooled to <−10° C. with dry-ice acetone bath (external temp @ −35° C.). To this solution was added n-hexyllithium (12.6 L, 2.09 M in hexane, 1.0 eq.) via addition funnel while controlling temp<−5° C. over 45 min (exothermic).

After addition, the reaction was aged for 20 min at the temp of −6 to −8° C. Methyl chloroformate (2.05 L, 1.00 equiv.) was slowly added via addition funnel over 43 min (exothermic, internal temp was controlled <14.2° C.); 10 min after addition (when temp became steady), the reaction was aged for about 1.5 h at 15 to 20° C. (@ 92% conversion based on the ratio of LCAP). Another 0.04 eq. (82 mL) of methyl chloroformate was added to increase the conversion to 94% (before addition, temp was about 15° C.).

Part 2:

The above reaction mixture was cooled to −18 to −25° C.; 0.7 eq of n-hexyllithium (9.10 L, 2.09 N) was added (very exothermic—controlled internal temp at −15° C. to −20° C.) and the reaction was aged at −15° C. to −20° C. for 30 min. Diisopropylamine (5.27 L, 1.4 eq) followed by n-hexyllithium (20.9 L, 2.09 N, 1.6 equiv.) was added via an additional funnel (controlling temp −15° C. to −20° C. during addition). The reaction was then aged for 20 min at <−15° C. (temp became steady), then changed to ice-water bath and temp was gradually warmed to 15° C. during overnight aging.

Part 3:

After the above reaction was complete, it was cooled to 0° C. with dry ice-acetone bath and methyl chloroformate (2.66 L, 1.3 equiv.) was added via an addition funnel over 25 min (controlling temp below 13° C. during addition. The reaction went from a dark solution to an orange slurry). The reaction was aged for 40 min around 8 to 10° C. and LC showed complete conversion.

Work-Up:

THF (6.4 L) was charged. The reaction was quenched with 5 N HCl (14.5 L) at <20° C. over 2 h to pH 4.28 (mixed solution), pH 3.88 (aqueous layer). Some precipitate was formed. 5 L of water was added and the precipitate was dissolved. This mixture was transferred into an extractor. The aqueous layer (30 L) was cut; the organic was washed with water (8 L). (The organic solution could be stored at 23° C. under $N_2$ for 2 days, but extended storage could result in decarboxylation.)

The organic layer was then transferred to a 100 L RB flask and concentrated to give 20 L of a slurry.

To the concentrated batch was charged THF (30 L) and heptane (6 L), and this solution was transferred to a 100 L extractor containing 12.6 L 22 wt/wt % aqueous $K_2CO_3$ solution, cooled to 10° C., The pH was adjusted to 13.1 (suggest PH range: 12.5 to 13.5) with KOH (4 L, 4.0 N). After warming up to 16 to 20° C., the aqueous layer was cut (no loss); the organic layer was washed with 15% $K_2CO_3$ (9 L) (15% $K_2CO_3$ was used to wash out residual KOH which could decompose the potassium salt) and transferred to 100 RB flask (this solution was stable at 23° C./$N_2$ for overnight). The batch was concentrated and flushed with 80 L THF to remove water.

To the concentrated batch (~total 10 L with 2.5 L THF content) was charged THF (2 L).

The product had begun to crystallize out and 60 L of n-heptane (6.7% loss in supernatant with only 30 L heptane) was charged via additional funnel over about 60 min. The resulting pale yellow slurry was aged for ca. 2 h (overnight aging is fine too). The product was collected by filtration, rinsed with 13 L of a solution of THF/heptane (1:13) and then 10 L heptane. The pale yellow product was dried under vacuum/$N_2$ to give the title compound as a potassium salt.

Salt Break and Neutral Form Isolation:

To a 100 L R.B. flask was charged the potassium salt (4.565 kg, 15.94 mol) and 16 L methanol, and the resulting mixture was chilled in ice bath to 6° C. Acetic acid (1.369 L, 23.91 mol) was added over 5 min. Near the end of addition, the mixture became very thick. 48 L water was added, and the resultant mixture was aged 1.5 hours at 15-20° C. (pH reading 6.1). The solid was filtered and the cake washed with 15 L water and dried under a nitrogen stream to give the title compound.

Step B1: (9R)-1-[3,5-Bis(trifluoromethyl)benzyl] cinchonan-1-ium-9-ol bromide

| Materials | FW | Mass | Volume | mol | Equiv. | d (g/mL) |
|---|---|---|---|---|---|---|
| Cinchonidine | 294.39 | 6.1 kg | | 20.72 | 1 | |
| 3,5-Bis(trifluoromethyl)benzyl bromide | 307.03 | 7.0 kg | 4.19 L | 22.8 | 1.1 | 1.671 |
| IPA | | | 66 L | | | |

3,5-Bis(trifluoromethyl)benzyl bromide (7.0 kg) was dissolved in isopropyl alcohol (IPA, 60 L) at 23° C. under nitrogen. To the stirred light yellow solution was added cinchonidine (6.1 kg) in portions over 20 minutes (no exotherm), affording a white slurry. Additional IPA (6 L) was added to rinse all the cinchonidine down into the reaction mixture. The slurry was heated to gentle reflux, reaching an internal temperature of 80-82.5° C. The mixture became less viscous while being heated, and once the temperature had reached 60.6° C. the last of the cinchonidine had dissolved to give a dark yellow solution. Once the mixture had reached gentle reflux, the reaction was seeded by the addition of 12 (62.3 g, 0.104 mol, 0.5 mol % relative to cinchonidine starting material), which led to the immediate precipitation of the product. The mixture was maintained at gentle reflux for 3.5 h, then heating was ceased and the orange slurry was allowed to cool to room temperature (21° C.) with stirring overnight.

After cooling, the mixture was filtered, and the pink product cake was washed with fresh IPA (1×10 L then 1×30 L) to remove unreacted starting materials and most of the color, and dried under vacuum with a nitrogen sweep to afford the title product.

Step E: (2R)-1'-tert-Butyl-5-(dibenzylamino)-1,3-dihydrospiro[indene-2,3'-pyrrolo[2,3-b]pyridin]-2'(17)-one

| Materials | FW | Mass | Volume | mol | Equiv. | d (g/mL) |
|---|---|---|---|---|---|---|
| methyl 1-tert-butyl-2-hydroxy-1H-pyrrolo[2,3-b]pyridine-3-carboxylate (0.11438 wt % solution in PhMe) | 248.28 | 1.429 kg | 12.49 L | 5.755 | 1.01 | |
| [2-(chloromethyl)-4-(dibenzyl-amino)phenyl]methanol hydrochloride (93.5 wt %) | 388.83 | 2.367 kg | | 5.698 | 1.0 | |
| (9R)-1-[3,5-bis(trifluoromethyl)benzyl]cinchonan-1-ium-9-ol bromide | 601.42 | 0.171 kg | | 0.285 | 0.05 | |
| toluene | | | 31.14 L | | | |
| $KOH_{(s)}$ | 56.1 | 15.966 kg | | | | |
| $H_2O$ | | 9.725 kg | | | | |

To water (9.725 kg) was added KOH (15.966 kg of 88.5 wt % pellets) in portions with ice-bath cooling under nitrogen, at such a rate as to maintain the internal temperature at ca. 30° C. After addition of ca. 80% of the KOH pellets, the water was drained from the ice-bath and the remaining KOH added rapidly, to achieve a maximum internal temperature of 37° C. and complete dissolution of the KOH.

The mixture was then allowed to cool to 32° C., then placed in an ice bath. Once the temperature reached 28° C., KOH began to crystallize (slightly exothermic). 15 minutes after the onset of crystallization, toluene (28 L) was added, and the stirring rate increased to maximum.

Once the temperature had reached 12.5° C., [2-(chloromethyl)-4-(dibenzylamino)phenyl]methanol hydrochloride (2.367 kg, 93.5 wt %, remainder MTBE and MeCN) was added in two equal portions over 5 minutes (minor exotherm), rinsing with toluene (1 L). After a further 15 minutes, 0.50 eq. methyl 1-tert-butyl-2-hydroxy-1H-pyrrolo[2,3-b]pyridine-3-carboxylate (6.246 kg of a 0.11438 wt % solution in toluene, 0.715 kg oxindole) was added in two portions over 2 minutes (exotherm from 11.9 to 14.0° C.). After a further 15 minutes 0.45 eq. of methyl 1-tert-butyl-2-hydroxy-1H-pyrrolo[2,3-b]pyridine-3-carboxylate (5.622 kg of a 0.11438 wt % solution in toluene, 0.643 kg oxindole) was added in two portions over 2 minutes (exotherm from 13.3 to 14.6° C.).

Fifteen minutes after addition of the second batch of methyl 1-tert-butyl-2-hydroxy-1H-pyrrolo[2,3-b]pyridine-3-carboxylate, an aliquot was removed and analyzed by HPLC.

After a further 15 minutes, a further charge of 0.06 eq. of methyl 1-tert-butyl-2-hydroxy-1H-pyrrolo[2,3-b]pyridine-3-carboxylate (0.750 kg of a 0.11438 wt % solution in toluene, 0.086 kg oxindole) was made, rinsing with toluene (1.1 L). The mixture was analyzed by HPLC again 30 minutes after addition of the third batch of methyl 1-tert-butyl-2-hydroxy-1H-pyrrolo[2,3-b]pyridine-3-carboxylate.

(9R)-1-[3,5-Bis(trifluoromethyl)benzyl]cinchonan-1-ium-9-ol bromide (0.171 kg) was added in one portion, rinsing with toluene (1.1 L). The mixture was stirred at ca. 10° C. for a further 16 h.

HPLC analysis at this point indicated formation of the title compound. Cooling of the vessel was ceased, THF (11.25 L) and H$_2$O (11.25 L) were added sequentially (exotherm to 14° C.), and stirring continued until the mixture had returned to 23° C. The mixture was then transferred into an extractor, and the layers were allowed to settle, leaving an orange organic phase, a colorless translucent aqueous phase, and a small amount of insoluble interfacial material. The aqueous layer was separated, H$_2$O (30 L) was added to the organic layer, and the mixture was stirred briefly and allowed to settle again, leaving virtually no interfacial material. The aqueous layer was separated, and the organic layer collected and stored.

The reaction was repeated three times on different scales to give a total theoretical yield of the title compound of 7.521 kg. The combined organic phases were concentrated at 30-35° C. to a target volume of 27 L, by which point the product had begun to precipitate. The slurry was then allowed to cool while MeOH (70 L) was added, and the mixture stirred at 23° C. for 16 h.

The product was then collected by filtration, washing the cake with 1:4 toluene:MeOH (1×20 L) and then MeOH (2×15 L), then dried under vacuum with a nitrogen sweep to afford the title compound.

Step F: (2R)-5-Amino-1,3-dihydrospiro[indene-2,3'-pyrrolo[2,3-b]pyridin]-2'(1'H)-one

| Materials | FW | Mass | Volume | mol | Equiv. | d (g/mL) |
|---|---|---|---|---|---|---|
| (2R)-1'-tert-butyl-5-(dibenzylamino)-1,3-dihydrospiro[indene-2,3'-pyrrolo[2,3-b]pyridin]-2'(1'H)-one | 487.63 | 5.48 kg | | 11.2 | 1.0 | |
| MsOH | 96.11 | 12.6 kg | 8.5 L | 131 | 11.65 | 1.48 |
| toluene | | | 1 L | | | |
| MeOH | | | 22 L | | | |
| 10% Pd/C (wet) | | 224 g | | | | |

To a 50 L RBF was charged 8.5 L of methanesulfonic acid (MsOH). (2R)-1'-tert-butyl-5-(dibenzylamino)-1,3-dihydrospiro[indene-2,3'-pyrrolo[2,3-b]pyridin]-2'(1'H)-one (6.6 kg crude, 83 wt %, remainder is toluene) was added as a solid over 40 min while temperature increased to 50° C. due to the exotherm. Toluene (1 L) was added to rinse down the solid (small amount of toluene also gives gentle reflux to rinse down any SM stuck on the vessel's walls). The reaction was heated to 90° C. over 30 min and the solution was held at 90° C. with no obvious exotherm observed (very mild refluxing, used a condenser).

The solution was cooled to 38° C. and diluted with MeOH (22 L, exothermic for the first 4 L MeOH addition). The solution was further cooled to 23° C. and subdivided to two equal halves for hydrogenation.

The first half of the above solution was charged to a hydrogenation vessel with 2 L MeOH rinse followed by 112 g of 10% PdC (wet) and a 2 L MeOH rinse. 60 psi of H$_2$ gas was applied with slow agitation in the first 30 min when the temperature rose from 20° C. to 27° C. The agitation was increased and the reaction was continued at 23° C. until LC revealed the reaction to be complete. The second half of the solution was hydrogenated under the same conditions. The two batches were combined and filtered through Solka-Floc® with MeOH rinse.

The filtrate was concentrated to 22 L, transferred to a 100 L extractor with 1 L MeOH and 1 L water rinse. Water (34 L) was added. The mixture was cooled to 20° C. and pH was adjusted to 1.5-2 with 9.6 L 10 N NaOH. Toluene (24 L) was added and the mixture was stirred for 10 min and settled for 30 min. The top toluene layer was analyzed to confirm no product loss and then discarded. The aqueous layer was collected and transferred back to the 100 L RBF and acidified to pH adjusted 4 over 30 min with 2.8 L of 5 N NaOH (crystals started to come out at pH 2.2 after 300 mL of the NaOH solution addition). A water bath was used to cool the very slight exothermic process. Another 480 mL of 5 N NaOH raised the pH to 6.3 (target pH 6-8, can be fined tuned with 5 N HCl if necessary). After aging for 30 min, the slurry was filtered with 6 L of 17 MeOH/water and then 12 L water. LC showed mother liquor loss of ~1% (0.3 g/L). Drying with nitrogen sweep and vacuum on a filter funnel provided the title compound. MS: m/z=252.0 (M+1).

Step G: (2R)-5-Iodo-1,3-dihydrospiro[indene-2,3'-pyrrolo[2,3-b]pyridin]-2'(1'H)-one A solution of sodium nitrite (107 g, 1.55 mol) in water (500 mL) was added dropwise over 15 min to a solution of (2R)-5-amino-1,3-dihydrospiro[indene-2,3'-pyrrolo[2,3-b]pyridin]-2'(1'H)-one (195 g, 0.776 mol) and p-toluenesulfonic acid (443 g, 2.33 mol) in acetonitrile (1.94 L) at 23° C. After stirring for 30 min, a solution of potassium iodide (322 g, 1.94 mol) in water (500 mL) was then added over 15 minutes. The resulting mixture was stirred at 23° C. for 40 minutes, then diluted with water (2 L) and basified by the addition of solid NaOH (98.0 g, 2.44 mol) with stirring. Iodine by-product was reduced by the addition of 10% aqueous sodium thiosulfate solution and stirring for an additional 30 minutes. The solids were collected by filtration, washed with water, and dried under nitrogen atmosphere to give the title compound, which was used without further purification. MS: m/z=363.1 (M+1).

Step H: Methyl (2R)-2'-oxo-1,1',2',3-tetrahydrospiro[indene-2,3'-pyrrolo[2,3-b]pyridine]-5-carboxylate A solution of (2R)-5-iodo-1,3-dihydrospiro[indene-2,3'-pyrrolo[2,3-b]pyridin]-2'(1'H)-one (100.0 g, 276 mmol), sodium acetate (45.3 g, 552 mmol) and dichloro 1,1'-bis(diphenylphosphino)ferrocene palladium(II) dichloromethane adduct (11.3 g, 13.8 mmol) in a mixture of MeOH (1 L) and toluene (30 mL) was pressurized to 120 psi of CO at 23° C. and then heated at 80° C. for 12 h with stirring. The reaction mixture was diluted with water (1 L), and the precipitate collected by filtration, washed with water, and dried under nitrogen atmosphere to give the title compound, which was used without further purification. MS: m/z=295.3 (M+1).

Step I: (2R)-2'-Oxo-1,1',2',3-tetrahydrospiro[indene-2,3'-pyrrolo[2,3-b]pyridine]-5-carboxylic acid A mixture of methyl (2R)-2'-oxo-1,1',2',3-tetrahydrospiro[indene-2,3'-pyrrolo[2,3-b]pyridine]-5-carboxylate (81.0 g, 276 mmol) and aqueous sodium hydroxide solution (5.52 N, 250 mL, 1.38 mol) in MeOH (2.5 L) was heated at reflux for 4 h. The mixture was allowed to cool to 23° C. before it was acidified to pH 2 with aqueous 1 N hydrochloric acid solution. The precipitate was filtered, washed with water, and dried under nitrogen atmosphere to give the title compound. MS: m/z=281.2 (M+1).
Method II:

Step A: (R)-Methyl 1'-tert-butyl-2'-oxo-1,1',2',3-tetrahydrospiro[indene-2,3'-pyrrolo[2,3-b]pyridine]-5-carboxylate A mixture of methyl 1,2-bis(bromomethyl)-4-benzoate (103 g, 320 mmol), methyl 1-tert-butyl-2-hydroxy-1H-pyrrolo[2,3-b]pyridine-3-carboxylate (prepared in Method I, Step A2, 79 g, 320 mmol), and potassium carbonate (265 g, 1919 mmol) was stirred at 23° C. for 7 h. The mixture was then concentrated to ~100 mL before partitioning between water (1.5 L) and CH₂Cl₂ (1 L). The aqueous was extracted with CH₂Cl₂ (3×500 mL), and the combined organics were dried over sodium sulfate and concentrated. The crude product was purified on silica eluting with 100% CH₂Cl₂ to provide the title compound as a racemic mixture. The enantiomers were then separated by supercritical fluid chromatography using a ChiralPak® IC column and eluting with CO₂:i-PrOH 70:30. Concentration of the second eluting peak provided the title compound. MS: m/z=351.0 (M+1).

Step B: (R)-2'-Oxo-1,1',2',3-tetrahydrospiro[indene-2,3'-pyrrolo[2,3-b]pyridine]-5-carboxylic acid A solution of (R)-methyl 1'-tert-butyl-2'-oxo-1,1',2',3-tetrahydrospiro[indene-2,3'-pyrrolo[2,3-b]pyridine]-5-carboxylate (53 g, 151 mmol) in methanesulfonic acid (196 mL) was heated at 90° C. for 1 h. Water (100 mL) was added and the solution was stirred for an additional 3 h at 90° C. The acidic mixture was cooled to 0° C., diluted with water (1 L), and basified to pH 14 with 50% aqueous NaOH solution. The basic mixture was then acidified to pH 3 by careful addition of concentrated aqueous HCl solution. The solids were collected by filtration and dried under nitrogen atmosphere to give the title compound which was used without further purification. MS: m/z=281.1 (M+1).

INTERMEDIATE 2

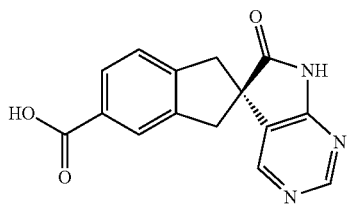 [SMILES: O=C(O)c1ccc2c(c1)C[C@@]1(C2)C(=O)Nc2ncncc21]

(2R)-6'-Oxo-1,3,6',7'-tetrahydrospiro[indene-2,5'-pyrrolo[2,3-d]pyrimidine]-5-carboxylic acid Step A: Methyl (2R)-4'-chloro-6'-oxo-1,3,6',7'-tetrahydrospiro[indene-2,5'-pyrrolo[2,3-d]pyrimidine]-5-carboxylate To a solution of methyl 3,4-bis(bromomethyl)benzoate (5.0 g, 15.5 mmol) and 4-chloro-5,7-dihydro-6H-pyrrolo[2,3-d]pyrimidin-6-one (5.3 g, 31.1 mmol) in N,N-dimethylformamide (150 mL) was added cesium carbonate (10.1 g, 31.1 mmol). After 10 min, water was added and the mixture was extracted with ethyl acetate. The combined organic extracts were washed with water, brine, dried over magnesium sulfate, filtered and concentrated. Purification by silica gel chromatography (1% methanol/dichloromethane→5% methanol/dichloromethane) then a second silica gel purification (100% dichloromethane→75% dichloromethane/EtOAc gave the title compound as a racemic mixture. Chiral separation of the individual enantiomers was accomplished by use of HPLC using a 10 cm ChiralPak® AD column (60% EtOH hexanes with 0.1% diethylamine to give the title compound as the 1$^{st}$ eluting enantiomer. MS: m/z=330.1 (M+1).

Step B: Methyl (2R)-6'-oxo-1,3,6',7'-tetrahydrospiro[indene-2,5'-pyrrolo[2,3-d]pyrimidine]-5-carboxylate To a solution of methyl (2R)-4'-chloro-6'-oxo-1,3,6',7'-tetrahydrospiro[indene-2,5'-pyrrolo[2,3-d]pyrimidine]-5-carboxylate (860 mg, 2.61 mmol) and triethylamine (364 μL, 2.61 mmol) in 10 mL of EtOAc was added 2.6 g of 10% palladium on carbon. The reaction was placed under 50 psi of H₂ and shaken on a Parr hydrogenation apparatus. After 16 h, the reaction was backfilled with nitrogen, filtered through Celite® and concentrated in vacuo to afford the title compound as a mixture with 1 equivalent of triethylamine hydrochloride. MS: m/z=296.1 (M+1).

Step C: (2R)-6'-Oxo-1,3,6',7'-tetrahydrospiro[indene-2,5'-pyrrolo[2,3-d]pyrimidine]-5-carboxylic acid To a solution of a mixture of methyl (2R)-6'-oxo-1,3,6',7'-tetrahydrospiro[indene-2,5'-pyrrolo[2,3-d]pyrimidine]-5-carboxylate (10 mg, 0.034 mmol) and triethylamine hydrochloride (0.034 mmol from previous step) in 1 mL of 1:1 THF/MeOH was added 1N LiOH (102 μL, 102 mmol). After 16 h, the reaction was neutralized to pH=7 with 3 N HCl and then concentrated in vacuo. The crude material was azeotroped from benzene to afford the title compound as a mixture with 3 equivalents of lithium chloride and 1 equivalent of triethylamine hydrochloride. MS: m/z=282.1 (M+1). ¹H NMR (500 MHz, DMSO d₆): δ 11.57 (s, 1H); 8.69 (s, 1H); 8.11 (s, 1H); 7.84 (m, 2H); 7.40 (dd, J=8.3 Hz, 1H); 3.34-3.28 (m, 4H).

INTERMEDIATE 3

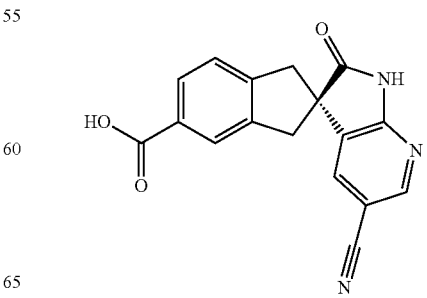

(2R)-5'-Cyano-2'-oxo-1,1',2',3-tetrahydrospiro[indene-2,3'-pyrrolo[2,3-b]pyridine]-5-carboxylic acid

Step A: (2R)-5'-Bromo-2'-oxo-1,1',2',3-tetrahydrospiro[indene-2,3'-pyrrolo[2,3-b]pyridine]-5-carboxylic acid To a stirred solution of (2R)-2'-oxo-1,1',2',3-tetrahydrospiro[indene-2,3'-pyrrolo[2,3-b]pyridine]-5-carboxylic acid (described in Intermediate 1) (1.52 g, 5.42 mmol) in acetic acid (AcOH, 30 mL) and H$_2$O (4 mL) at 50° C. was added a solution of bromine (1.19 g, 7.47 mmol) in AcOH (1 mL) dropwise. The resulting mixture was heated at 50° C. for 2 h, then additional bromine (1.19 g, 7.47 mmol) in AcOH (1 mL) was added dropwise. The resulting mixture was heated at 50° C. for 16 h, then allowed to cool to ambient temperature. The precipitate was isolated by filtration, washing with H$_2$O, and dried to give the crude product, which was purified by reversed-phase HPLC on a C-18 column, eluting with a gradient of H$_2$O:CH$_3$CN:TFA-95:5:0.1 to 65:35:0.1, to give the title compound. MS: m/z=360.9 (M+1).

Step B: (2R)-5'-Cyano-2'-oxo-1,1',2',3-tetrahydrospiro[indene-2,3'-pyrrolo[2,3-b]pyridine]-5-carboxylic acid Argon was bubbled through a stirred mixture of (2R)-5'-bromo-2'-oxo-1,1',2',3-tetrahydrospiro[indene-2,3'-pyrrolo[2,3-b]pyridine]-5-carboxylic acid (433 mg, 1.21 mmol), zinc cyanide (205 mg, 1.75 mmol), and zinc (31 mg, 0.47 mmol) in N,N-dimethylacetamide (10 mL) for 10 min. To the resulting mixture was added tris(dibenzylideneacetone)dipalladium(0) (27 mg, 0.030 mmol) and 1,1'-bis(diphenylphosphino)ferrocene (23 mg, 0.041 mmol) and argon was bubbled through the mixture for an additional 5 min. The reaction mixture was heated at 120° C. for 4 h, cooled to ambient temperature, and partitioned between EtOAc (100 mL) and 1 N aqueous hydrochloric acid (100 mL). The organic layer was washed with brine, then dried over sodium sulfate, filtered, and concentrated to dryness in vacuo. The residue was dissolved in a minimal volume of DMF and H$_2$O was added to produce a precipitate. The precipitate was isolated by filtration, washing with H$_2$O, and dried to give the title compound. MS: m/z=306.0 (M+1); $^1$H NMR (400 MHz, DMSO-d$_6$) δ 12.81 (br s, 1H), 11.68 (s, 1H), 8.59 (d, 1H, J=1.9 Hz), 7.86-7.83 (m, 2H), 7.80 (dd, 1H, J=2.0, 0.5 Hz), 7.39 (d, 1H, J=8.3 Hz), 3.42-3.29 (m, 4H).

INTERMEDIATE 4

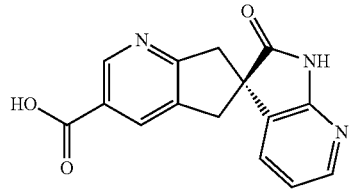 [SMILES: O=C(O)c1cnc2c(c1)C[C@@]1(C2)C(=O)Nc2ncccc21]

(6S)-2'-Oxo-1',2',5,7-tetrahydrospiro[cyclopenta[b]pyridine-6,3'-pyrrolo[2,3-b]pyridine]-3-carboxylic acid The title compound can be prepared by either Method I or Method II as described below.
Method I:

Step A: (6S)-3-Iodo-5,7-dihydrospiro[cyclopenta[b]pyridine-6,3'-pyrrolo[2,3-b]pyridin]-2'(1'H)-one A solution of sodium nitrite (36.1 g, 523 mmol) in water (20 mL) was added dropwise over 5 min to a solution of (6S)-3-amino-5,7-dihydrospiro[cyclopenta[b]pyridine-6,3'-pyrrolo[2,3-b]pyridin]-2'(1'H)-one (prepared according to the procedures described in WO2008/020902, 66.0 g, 262 mmol) and p-toluenesulfonic acid (149 g, 785 mmol) in acetonitrile (650 mL) at 23° C. After stirring for 30 min, a solution of potassium iodide (109 g, 654 mmol) in water (20 mL) was added over 5 min. The resulting mixture was stirred at 23° C. for 40 min, then diluted with water (1 L) and basified by the addition of solid NaOH (33.0 g, 824 mmol) with stirring. Iodine by-product was reduced by the addition of 10% aqueous sodium thiosulfate solution and stirring for an additional 30 min. The solids were collected by filtration, washed with water, and dried under nitrogen atmosphere to give the title compound, which was used without further purification. MS: m/z=363.9 (M+1).

Step B: Methyl (6S)-2'-oxo-1',2',5,7-tetrahydrospiro[cyclopenta[b]pyridine-6,3'-pyrrolo[2,3-b]pyridine]-3-carboxylate A solution of (6S)-3-iodo-5,7-dihydrospiro[cyclopenta[b]pyridine-6,3'-pyrrolo[2,3-b]pyridin]-2'(1'H)-one (51.0 g, 140 mmol), sodium acetate (23.0 g, 281 mmol) and dichloro 1,1'-bis(diphenylphosphino)ferrocene palladium(II) dichloromethane adduct (2.9 g, 3.5 mmol) in MeOH (560 mL) was pressurized to 120 psi of CO at 23° C. and then heated at 80° C. for 12 h with stirring. The reaction mixture was diluted with water (1 L), and the precipitate collected by filtration, washed with water, and dried under nitrogen atmosphere to give the title compound, which was used without further purification. MS: m/z=296.1 (M+1).

Step C: (6S)-2'-Oxo-1',2',5,7-tetrahydrospiro[cyclopenta[b]pyridine-6,3'-pyrrolo[2,3-b]pyridine]-3-carboxylic acid A mixture of methyl (6S)-2'-oxo-1',2',5,7-tetrahydrospiro[cyclopenta[b]pyridine-6,3'-pyrrolo[2,3-b]pyridine]-3-carboxylate (30.0 g, 102 mmol) and aqueous 6 N sodium hydroxide solution (50.8 mL, 305 mmol) in MeOH (920 mL) was heated at reflux for 1 h. The mixture was allowed to cool to 23° C. before it was acidified to pH ~6 with aqueous 1 N hydrochloric acid solution, resulting in a black precipitate which was removed by filtration. The filtrate was concentrated under reduced pressure to a volume of ~100 mL and then partitioned between water (500 mL) and 2-methyltetrahydrofuran (2-MeTHF, 250 mL). The aqueous layer was extracted with 2-MeTHF (5×250 mL), and the combined organic layers were dried over sodium sulfate and concentrated to provide the title compound. MS: m/z=282.0 (M+1).
Method II:

Step A: Dimethyl 5-bromopyridine-2,3-dicarboxylate

Concentrated sulfuric acid (1 L, 18.7 mol) was added slowly over 10 min to a suspension of pyridine-2,3-dicarboxylic acid (5.00 kg, 29.9 mol) in methanol (50 L), dissolving the suspension. The resulting mixture was heated at reflux for 48 h then cooled to 40° C. Bromine (8.0 kg, 50 mol) was added slowly over 2 h in 1-kg portions, keeping the temperature below 55° C. The reaction mixture was then heated at 55° C. for 24 h, cooled to 50° C. and additional Br$_2$ (4.0 kg, 25 mol) was added slowly over 1 h in 1-kg portions, keeping temperature below 55° C. The reaction mixture was heated at 55° C. for 24 h, concentrated to a minimum volume (internal temp ~30° C., solution may occasionally foam), then diluted with isopropyl acetate (50 L) and washed with a saturated aqueous sodium sulfite solution (3×20 L) (final extract is ~pH 8) followed by water (20 L). The organic layer was concentrated to approximately 15 L then diluted with heptane (40 L). The resulting slurry was stirred for 24 h at 23° C. The solids were filtered, washed with heptane (10 L), and dried to give the title compound.

Step B: (5-Bromopyridine-2,3-diyl)dimethanol

Sodium borohydride (15.9 g, 420 mmol) was added portionwise over 30 min to a solution of dimethyl 5-bromopyridine-2,3-dicarboxylate (20 g, 73 mmol) in ethanol (460 mL) precooled to 0° C. A solution of calcium chloride (23.3 g, 209 mmol) in 150 mL was added slowly at 0° C., and the reaction mixture was warmed to 23° C. and stirred overnight. Excess sodium borohydride was quenched by slow addition of aqueous 2 N HCl solution (230 mL, 460 mmol), followed by a stirring at 23° C. for 2 h. The mixture was concentrated to dryness. Saturated aqueous sodium bicarbonate solution was added to the residue until a pH of approximately 7 was reached. The aqueous mixture was extracted with 2-methyltetrahydrofuran (4×200 mL). The combined organic layers were dried over sodium sulfate then treated with a solution of 4 N HCl in dioxane (25 mL, 100 mmol). The resulting solid was filtered, washed with 2-methyltetrahydrofuran, and dried to give the title compound as a hydrochloride salt. MS: m/z=218.1 (M+1).

Step C: (5-Bromopyridine-2,3-diyl)dimethanediyl dimethanesulfonate

A slurry of (5-bromopyridine-2,3-diyl)dimethanol hydrochloride (12.9 g, 59.2 mmol) in tetrahydrofuran (400 mL) at 0° C. was treated with triethylamine (37.1 mL, 266 mmol). To the resulting mixture was added portionwise methanesulfonic anhydride (30.9 g, 177 mmol), keeping temperature below 5° C. The reaction mixture was stirred at 0° C. for 1 h, then partitioned between saturated aqueous sodium bicarbonate solution (500 mL) and ethyl acetate (500 mL). The organic layer was washed saturated aqueous sodium bicarbonate solution, dried over magnesium sulfate, and concentrated to give the title compound. MS: m/z=376.0 (M+1).

Step D: 3-Bromo-1'-{[2-(trimethylsilyl)ethoxy]methyl}-5,7-dihydrospiro[cyclopenta[b]pyridine-6,3'-pyrrolo[2,3-b]pyridin]-2'(1'H)-one (5-Bromopyridine-2,3-diyl)dimethanediyl dimethanesulfonate (17.0 g, 45.4 mmol) was added to a mixture of 1-{[2-(trimethylsilyl)ethoxy]methyl}-1,3-dihydro-2H-pyrrolo[2,3-b]pyridin-2-one (prepared according to the procedures described in WO2008/020902, 14.0 g, 53.0 mmol) and cesium carbonate (49.0 g, 150 mmol) in ethanol (500 mL) 23° C., and the resulting mixture was stirred for 20 h. The reaction mixture was concentrated then partitioned between ethyl acetate (500 mL) and water (500 mL). The organic layer was dried over magnesium sulfate and concentrated. The residue was purified via silica gel chromatography (heptane initially, grading to 100% EtOAc) to give the title compound. MS: m/z=448.1 (M+1).

Step E: Methyl (6S)-2'-oxo-1'-{[2-(trimethylsilyl) ethoxy]methyl}-1',2',5,7-tetrahydrospiro[cyclopenta [b]pyridine-6,3'-pyrrolo[2,3-b]pyridine]-3-carboxylate A mixture of 3-bromo-1'-{[2-(trimethylsilyl)ethoxy]methyl}-5,7-dihydrospiro[cyclopenta[b]pyridine-6,3'-pyrrolo[2,3-b]pyridin]-2'(1'H)-one (22.0 g, 49.3 mmol), PdCl₂(dppf).CH₂Cl₂ (2.012 g, 2.46 mmol), and sodium acetate (8.1 g, 99 mmol) in methanol (150 mL) was pressurized to 300 psi of carbon monoxide and then heated at 85° C. for 72 h. The reaction mixture was allowed to cool then concentrated. The residue was purified via silica gel chromatography (heptane initially, grading to 100% EtOAc) to give the title compound as a racemic mixture. MS: m/z=426.1 (M+1). Resolution of the enantiomers by supercritical fluid chromatography (SFC) using a ChiralPak® AD-H column and eluting with 40% ethanol in CO₂ (0.05% diethylamine as modifier) provided the title compound as the second enantiomer to elute.

Step F: (6S)-2'-Oxo-1',2',5,7-tetrahydrospiro[cyclopenta[b]pyridine-6,3'-pyrrolo[2,3-b]pyridine]-3-carboxylic acid A solution of methyl (6S)-2'-oxo-1'-{[2-(trimethylsilyl) ethoxy]methyl}-1',2',5,7-tetrahydrospiro[cyclopenta[b]pyridine-6,3'-pyrrolo[2,3-b]pyridine]-3-carboxylate (238 g, 559 mmol) in methanol (2 L) was saturated with HCl gas, allowing temperature to increase to 55° C. The reaction mixture was cooled to 23° C., stirred for 20 h, then concentrated. Aqueous 10 N sodium hydroxide (400 mL, 4 mol) was added to a solution of the residue in methanol (2 L), and the resulting mixture was heated at reflux for 2 h. The solution was cooled to 23° C. and the pH was adjusted to 3 with concentrated HCl. The resulting solid was filtered, washed with water then heptane, and dried to give the title compound. MS: m/z=282.2 (M+1).

INTERMEDIATE 5

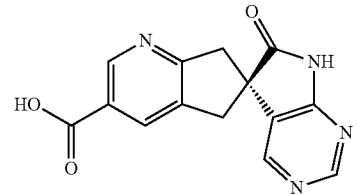 [SMILES: O=C(O)c1cnc2c(c1)C[C@@]1(C2)C(=O)Nc2ncncc21]

(6S)-6'-Oxo-5,6',7,7'-tetrahydrospiro[cyclopenta[b] pyridine-6,5'-pyrrolo[2,3-d]pyrimidine]-3-carboxylic acid Step A: tert-Butyl 5-bromo-6-chloropyridine-3-carboxylate To a solution of 5-bromo-6-chloronicotinic acid (25.0 g, 106 mmol) in tetrahydrofuran (1.06 L) was added di-tert-butyl dicarbonate (69.2 g, 317 mmol) followed by 4-dimethylaminopyridine (12.9 g, 106 mmol). After 16 h, the mixture was diluted with water and aqueous hydrochloric acid was added (106 mL, 1 M, 106 mmol). The mixture was extracted with ethyl acetate (3×). The combined organic extracts were washed with brine (3×), dried over magnesium sulfate, filtered and concentrated. Purification by silica gel chromatography (100% dichloromethane→10% methanol dichloromethane) gave the title compound. MS: m/z=294.1 (M+1).

Step B: tert-Butyl 5,6-diethenylpyridine-3-carboxylate

To a solution of tert-butyl 5-bromo-6-chloropyridine-3-carboxylate (24.0 g, 82.0 mmol) in acetonitrile (615 mL) and water (205 mL) were added potassium vinyltrifluoroborate (33.0 g, 246 mmol) and triphenylphosphine-3,3',3''-trisulfonic acid trisodium salt (4.20 g, 7.38 mmol). Diisopropylamine (88.0 mL, 615 mmol) was added followed by palladium(II) acetate (0.553 g, 2.46 mmol). The mixture was heated to 75° C. After 16 h, the mixture was cooled to ambient temperature and saturated sodium bicarbonate was added. The mixture was washed with dichloromethane (3×) and the combined organics were washed with water, brine, and dried with magnesium sulfate, filtered and concentrated. Purification by silica gel chromatography (100% dichloromethane→5% methanol dichloromethane) gave the title compound. MS: m/z=232.3 (M+1).

Step C: tert-Butyl 5,6-bis(hydroxymethyl)pyridine-3-carboxylate

To a solution of tert-butyl 5,6-diethenylpyridine-3-carboxylate (19.0 g, 82 mmol) in dichloromethane (821 mL) at −78° C. was added ozone gas. The ozone bubbled though the solution until saturated (1 h). Nitrogen gas was then bubbled through the solution. The mixture was diluted with methanol (821 mL) and sodium borohydride (7.77 g, 205 mmol) was added. After 15 min, the mixture was quenched with saturated aqueous sodium bicarbonate and washed with dichloromethane (3×). The combined organics were washed with brine, dried with magnesium sulfate, filtered and concentrated. Purification by silica gel chromatography (100% dichloromethane→15% methanol dichloromethane) gave the title compound. MS: m/z=240.3 (M+1).

Step D: tert-Butyl 5,6-bis(chloromethyl)pyridine-3-carboxylate

To a solution of tert-butyl 5,6-bis(hydroxymethyl)pyridine-3-carboxylate (5.87 g, 24.5 mmol) in N,N-dimethylformamide (146 mL) at 0° C. was added triethylamine (13.7 mL, 98 mmol) followed by methanesulfonic anhydride (12.8 g, 73.6 mmol). After 15 min, water (29.2 mL) and sodium chloride (8.60 g, 147 mmol) were added and the mixture warmed to ambient temperature. After 16 h, saturated aqueous sodium bicarbonate was added and the mixture was extracted with ethyl acetate (3×). The combined organics were washed with water (3×) and then brine (3×), dried with magnesium sulfate, filtered and concentrated. Purification by silica gel chromatography (100% dichloromethane→10% methanol dichloromethane) gave the title compound. MS: m/z=276.2 (M+1).

Step E: tert-Butyl (6S)-4'-chloro-6'-oxo-5,6',7,7'-tetrahydrospiro[cyclopenta[b]pyridine-6,5'-pyrrolo [2,3-d]pyrimidine]-3-carboxylate To a solution of tert-butyl 5,6-bis(chloromethyl)pyridine-3-carboxylate (1.80 g, 6.52 mmol) in N,N-dimethylformamide (93.0 mL) was added 4-chloro-5,7-dihydro-6H-pyrrolo[2,3-d]pyrimidin-6-one (1.80 g, 10.62 mmol), cesium carbonate (3.65 g, 11.21 mmol), and sodium bromide (0.671 g, 6.52 mmol). After 30 min, saturated aqueous sodium bicarbonate was added and the mixture was washed with ethyl acetate (3×). The combined organics were washed with water (3×), brine (3×) and were dried with magnesium sulfate, filtered and concentrated. Purification by silica gel chromatography (100% dichloromethane→10% methanol dichloromethane) then a second purification by silica gel chromatography (100% dichloromethane→30% ethyl acetate dichloromethane) gave the title compound as a racemic mixture. Chiral separation of the individual enantiomers was accomplished by use of HPLC using a 10 cm ChiralPak® AD column (60% EtOH hexanes with 0.1% diethylamine) to give the title compound as the 1$^{st}$ eluting enantiomer. MS: m/z=373.2 (M+1).

Step F: tert-Butyl (6S)-6'-oxo-5,6',7,7'-tetrahydrospiro[cyclopenta[b]pyridine-6,5'-pyrrolo[2,3-d] pyrimidine]-3-carboxylate To a solution of tert-butyl (6S)-4'-chloro-6'-oxo-5,6',7,7'-tetrahydrospiro [cyclopenta[b]pyridine-6,5'-pyrrolo[2,3-d] pyrimidine]-3-carboxylate (200 mg, 0.537 mmol) in dry ethyl acetate (5.37 mL) was added triethylamine (299 μL, 2.15 mmol) and palladium on carbon (571 mg, 10%, 0.537 mmol). The reaction was placed on a Parr apparatus at 50 psi hydrogen gas. After 16 h, the reaction mixture was filtered under a nitrogen atmosphere through Celite®, washing with ethyl acetate. The filtrate was concentrated to give the title compound, along with one equivalent of triethylamine hydrochloride. MS: m/z=339.3 (M+1).

Step G: (6S)-6'-Oxo-5,6',7,7'-tetrahydrospiro[cyclopenta[b]pyridine-6,5'-pyrrolo[2,3-d]pyrimidine]-3-carboxylic acid To solid tert-butyl (6S)-6'-oxo-5,6',7,7'-tetrahydrospiro [cyclopenta[b]pyridine-6,5'-pyrrolo[2,3-d]pyrimidine]-3-carboxylate (255 mg, 0.536 mmol) containing one equivalent of triethylamine hydrochloride (from previous step) was added hydrochloric acid solution (20 mL, 4 M in dioxane). After 16 h, the mixture was concentrated to give the title compound as a bis hydrochloric acid salt with one equivalent of triethylamine hydrochloride. MS: m/z=283.2 (M+1). $^{1}$H NMR (500 MHz, DMSO): δ 11.75 (s, 1H); 9.50 (s, 1H); 8.90 (s, 1H); 8.80 (s, 1H); 8.40 (s, 1H); 8.20 (s, 1H); 3.50-3.40 (m, 4H).

INTERMEDIATE 6

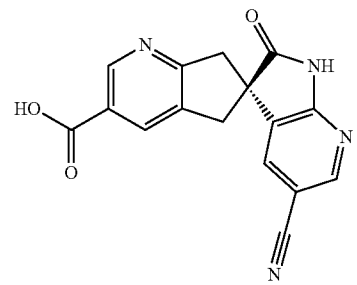 [SMILES: N#Cc1cnc2c(c1)[C@@]1(Cc3cc(C(=O)O)cnc3C1)C(=O)N2]

(6S)-5'-Cyano-2'-oxo-1',2',5,7-tetrahydrospiro[cyclopenta[b]pyridine-6,3'-pyrrolo[2,3-b]pyridine]-3-carboxylic acid Step A: (6S)-5'-Bromo-2'-oxo-1',2',5,7-tetrahydrospiro[cyclopenta[b]pyridine-6,3'-pyrrolo[2,3-b] pyridine]-3-carboxylic acid To a stirred mixture of (6S)-2'-oxo-1',2',5,7-tetrahydrospiro[cyclopenta[b]pyridine-6,3'-pyrrolo[2,3-b]pyridine]-3-carboxylic acid (described in Intermediate 4) (1.03 g, 3.66 mmol) in boron trifluoride dihydrate (12 mL) was added N-bromosuccinimide (1.37 g, 7.70 mmol) and the resulting mixture was heated at 50° C. for 2 h. The reaction mixture was cooled to ambient temperature and N-bromosuccinimide (1.83 g, 10.3 mmol) was added. The resulting mixture was heated at 50° C. for 16 h, allowed to cool to ambient temperature, and the crude mixture was purified by reversed-phase HPLC on a C-18 column, eluting with a gradient of H₂O:CH₃CN:TFA-95:5:0.1 to 65:35:0.1, to give the title compound. MS: m/z=361.9 (M+1).

Step B: (6S)-5'-Cyano-2'-oxo-1',2',5,7-tetrahydrospiro[cyclopenta[b]pyridine-6,3'-pyrrolo[2,3-b]pyridine]-3-carboxylic acid Argon was bubbled through a stirred mixture of (6S)-5'-bromo-2'-oxo-1',2',5,7-tetrahydrospiro[cyclopenta[b]pyridine-6,3'-pyrrolo[2,3-b]pyridine]-3-carboxylic acid (352 mg, 0.98 mmol), zinc cyanide (150 mg, 1.28 mmol), and zinc (20 mg, 0.31 mmol) in N,N-dimethylacetamide (6 mL) for 10 min. To the resulting mixture was added tris(dibenzylideneacetone)dipalladium(0) (20 mg, 0.022 mmol) and 1,1'-bis(diphenylphosphino)ferrocene (16 mg, 0.029 mmol) and argon was bubbled through the mixture for an additional 5 min. The reaction mixture was heated at 120° C. for 18 h, cooled to ambient temperature, and purified directly by reversed-phase HPLC on a C-18 column, eluting with a gradient of H₂O:CH₃CN:TFA-95:5:0.1 to 65:35:0.1, to give the title compound. MS: m/z=306.9 (M+1); 1H NMR (400 MHz, DMSO-d₆) δ 11.71 (s, 1H), 8.91 (d, 1H, J=1.9 Hz), 8.61 (d, 1H, J=2.0 Hz), 8.14 (d, 1H, J=1.8 Hz), 8.03 (d, 1H, J=1.8 Hz), 3.49-3.34 (m, 4H).

INTERMEDIATE 7

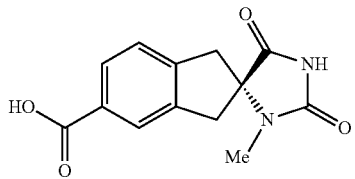 [SMILES: CN1C(=O)NC(=O)[C@@]12Cc1ccc(C(=O)O)cc1C2]

(4S)-3-Methyl-2,5-dioxo-1',3'-dihydrospiro[imidazolidine-4,2'-indene]-5'-carboxylic acid Step A: 1',3'-Dihydro-2H,5H-spiro[imidazolidine-4,2'-indene]-2,5-dione A stirred mixture of 2-indanone (250 g, 1.89 mol), sodium cyanide (278 g, 5.68 mol) and ammonium carbonate (1.81 kg, 18.9 mol) in H₂O (1.5 L) and EtOH (1.5 L) was heated at 70° C. for 3 h, then allowed to cool to ambient temperature. The precipitate was collected by filtration, washed with H₂O, and dried in vacuo to give the title compound. MS: m/z=202.0 (M+1).

Step B: 5'-Bromo-1',3'-dihydro-2H,5H-spiro[imidazolidine-4,2'-indene]-2,5-dione

To a stirred solution of 1',3'-dihydro-2H,5H-spiro[imidazolidine-4,2'-indene]-2,5-dione (118 g, 0.584 mol) in 48% HBr (2 L) was added bromine (92 g, 0.584 mol) dropwise and the reaction mixture was allowed to stir at ambient temperature for 48 h. The reaction mixture was poured onto ice and the precipitate was collected by filtration, washed with H₂O, and dried in vacuo. The crude product was recrystallized from EtOH to afford the title compound. MS: m/z=282.9 (M+1).

Step C: 5'-Bromo-1-(4-methoxybenzyl)-1',3'-dihydro-2H,5H-spiro[imidazolidine-4,2'-indene]-2,5-dione To a stirred suspension of 5'-bromo-1',3'-dihydro-2H,5H-spiro[imidazolidine-4,2'-indene]-2,5-dione (164 g, 0.586 mol) and potassium carbonate (89 g, 0.645 mol) in DMF (2 L) at 0° C. was added 4-methoxybenzyl chloride (96 g, 0.615 mmol) dropwise. The resulting mixture was allowed to warm slowly to ambient temperature and stirred for 18 h. The reaction mixture was poured into H₂O and the precipitate was collected by filtration, washed with H₂O, and dried in vacuo to give the title compound. MS: m/z=403.1 (M+1).

Step D: 5'-Bromo-1-(4-methoxybenzyl)-3-methyl-1',3'-dihydro-2H,5H-spiro[imidazolidine-4,2'-indene]-2,5-dione To a stirred solution of 5'-bromo-1-(4-methoxybenzyl)-1',3'-dihydro-2H,5H-spiro[imidazolidine-4,2'-indene]-2,5-dione (5.0 g, 12.5 mmol) in DMF (50 mL) at 10° C. was added sodium hydride (60% dispersion in oil, 1.50 g, 37.5 mmol) portionwise. The resulting mixture was stirred for 1 h at ambient temperature, then recooled to −10° C. Iodomethane (5.30 g, 37.3 mmol) was added dropwise and stirring was continued for 1 h. The reaction mixture was partitioned between H₂O (100 mL) and EtOAc (100 mL). The organic layer was removed and the aqueous phase was extracted further with EtOAc (2×50 mL). The combined organic extracts were dried over sodium sulfate, filtered, and concentrated to dryness in vacuo. The crude product was purified by silica gel chromatography, eluting with a gradient of hexanes:EtOAc-100:0 to 0:100, to give the title compound. MS: m/z=417.0 (M+1).

Step E: 5'-Bromo-3-methyl-1',3'-dihydro-2H,5H-spiro[imidazolidine-4,2'-indene]-2,5-dione To a stirred solution of 5'-bromo-1-(4-methoxybenzyl)-3-methyl-1',3'-dihydro-2H,5H-spiro[imidazolidine-4,2'-indene]-2,5-dione (90.0 g, 0.217 mol) in CH₃CN (900 mL) was added a solution of ammonium cerium(IV) nitrate (594 g, 1.08 mol) in H₂O (900 mL). The resulting mixture was stirred at ambient temperature for 30 min then extracted with EtOAc (3×1 L). The combined organic extracts were washed with brine, dried over sodium sulfate, filtered, and concentrated to dryness in vacuo. The residue was triturated with EtOH and dried in vacuo to give the title compound. MS: m/z=296.9 (M+1).

Step F: 3-Methyl-2,5-dioxo-1',3'-dihydrospiro[imidazolidine-4,2'-indene]-5'-carboxylic acid To a stirred suspension of 5'-bromo-3-methyl-1',3'-dihydro-2H,5H-spiro[imidazolidine-4,2'-indene]-2,5-dione (30.0 g, 0.102 mol) in THF (1 L) at −70° C. was added dropwise ethyl magnesium bromide (2.75 M in THF, 149 mL, 0.410 mol). The resulting mixture was stirred at −70° C. for 20 min, then n-butyllithium (2.5 M in hexanes, 327 mL, 0.818 mol) was added dropwise over 10 min. Stirring was continued at −70° C. for 20 min, then CO₂ (g) was bubbled into the reaction mixture for 2.5 h. The reaction mixture was allowed to warm slowly to ambient temperature and the THF was removed in vacuo. The residue was suspended in 0.5 N HCl (500 mL) and the mixture was adjusted to pH=1-2 by the addition of conc. HCl. The precipitate was isolated by filtration, washed with H$_2$O, and dried in vacuo to give the title compound. MS: m/z=260.9 (M+1).

Step G: Methyl (4S)-3-methyl-2,5-dioxo-1',3'-dihydrospiro[imidazolidine-4,2'-indene]-5'-carboxylate To a stirred solution of 3-methyl-2,5-dioxo-1',3'-dihydrospiro[imidazolidine-4,2'-indene]-5'-carboxylic acid (4.50 g, 17.3 mmol) in MeOH (500 mL) was added conc. H$_2$SO$_4$ (1 mL, 18 mmol) and the resulting mixture was heated at reflux for 24 h. The reaction mixture was concentrated in vacuo to a volume of about 150 mL and then partitioned between saturated aqueous sodium bicarbonate (200 mL) and CHCl$_3$ (500 mL). The aqueous layer was extracted further with CHCl$_3$ (250 mL). The combined organic extracts were washed with brine, dried over sodium sulfate, filtered, and concentrated to dryness in vacuo to give the racemic product. Separation of the enantiomers was achieved by SFC on a ChiralPak AD-H column, eluting with CO$_2$:i-PrOH-70:30, to give methyl (4S)-3-methyl-2,5-dioxo-1',3'-dihydrospiro[imidazolidine-4,2'-indene]-5'-carboxylate, the title compound, as the first major peak, and methyl (4R)-3-methyl-2,5-dioxo-1',3'-dihydrospiro[imidazolidine-4,2'-indene]-5'-carboxylate as the second major peak. MS: m/z=274.9 (M+1).

Step H: (4S)-3-Methyl-2,5-dioxo-1',3'-dihydrospiro[imidazolidine-4,2'-indene]-5'-carboxylic acid To a stirred solution of methyl (4S)-3-methyl-2,5-dioxo-1',3'-dihydrospiro[imidazolidine-4,2'-indene]-5'-carboxylate (1.40 g, 5.10 mmol) in THF (30 mL) and H$_2$O (15 mL) was added 1.0 N aqueous lithium hydroxide (20.4 mL, 20.4 mmol) and the reaction mixture was stirred at ambient temperature for 18 h. The THF was removed in vacuo and the resulting mixture was adjusted to pH=1 by addition of 1.0 N HCl. The precipitate was isolated by filtration, washed with H$_2$O, and dried in vacuo to give the title compound. MS: m/z=260.9 (M+1); $^1$H NMR (400 MHz, DMSO-d$_6$) δ 12.85 (br s, 1H), 10.98 (br s, 1H), 7.82 (s, 1H), 7.81 (d, 1H, J=8.4 Hz), 7.37 (d, 1H, J=8.4 Hz), 3.38-3.28 (m, 4H), 2.56 (2, 3H).

INTERMEDIATE 8

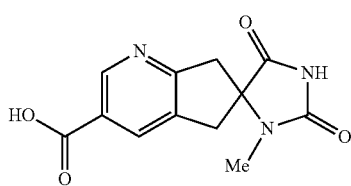 [SMILES: CN1C(=O)NC(=O)C12Cc1cc(C(=O)O)cnc1C2]

3'-Methyl-2',5'-dioxo-5,7-dihydrospiro[cyclopenta[b]pyridine-6,4'-imidazolidine]-3-carboxylic acid Step A: Dimethyl 5-bromopyridine-2,3-dicarboxylate Concentrated sulfuric acid (1 L, 18.7 mol) was added slowly over 10 min to a suspension of pyridine-2,3-dicarboxylic acid (5.00 kg, 29.9 mol) in methanol (50 L), dissolving the suspension. The resulting mixture was heated at reflux for 48 h then cooled to 40° C. Bromine (8.0 kg, 50 mol) was added slowly over 2 h in 1-kg portions, keeping the temperature below 55° C. The reaction mixture was then heated at 55° C. for 24 h, cooled to 50° C. and additional Br$_2$ (4.0 kg, 25 mol) was added slowly over 1 h in 1-kg portions, keeping temperature below 55° C. The reaction mixture was heated at 55° C. for 24 h, concentrated to a minimum volume (internal temp ~30° C., solution may occasionally foam), then diluted with isopropyl acetate (50 L) and washed with a saturated aqueous sodium sulfite solution (3×20 L) (final extract is ~pH 8) followed by water (20 L). The organic layer was concentrated to approximately 15 L then diluted with heptane (40 L). The resulting slurry was stirred for 24 h at 23° C. The solids were filtered, washed with heptane (10 L), and dried to give the title compound.

Step B: (5-Bromopyridine-2,3-diyl)dimethanol

Sodium borohydride (15.9 g, 420 mmol) was added portionwise over 30 minutes to a solution of dimethyl 5-bromopyridine-2,3-dicarboxylate (20 g, 73 mmol) in ethanol (460 mL) precooled to 0° C. A solution of calcium chloride (23.3 g, 209 mmol) in ethanol (150 mL) was added slowly at 0° C., and the reaction mixture was warmed to 23° C. and stirred overnight. Excess sodium borohydride was quenched by slow addition of aqueous 2 N HCl solution (230 mL, 460 mmol), followed by a stirring at 23° C. for 2 h. The mixture was concentrated to dryness. Saturated aqueous sodium bicarbonate solution was added to the residue until a pH of approximately 7 was reached. The aqueous mixture was extracted with 2-methyltetrahydrofuran (4×200 mL). The combined organic layers were dried over sodium sulfate then treated with a solution of 4 N HCl in dioxane (25 mL, 100 mmol). The resulting solid was filtered, washed with 2-methyltetrahydrofuran, and dried to give the title compound as a hydrochloride salt. MS: m/z=218.1 (M+1).

Step C: 5-Bromo-2,3-bis(chloromethyl)pyridine

To a solution of (5-bromopyridine-2,3-diyl)dimethanol (5.0 g, 22.9 mmol) in DMF (230 mL) at ambient temperature was added thionyl chloride (5.59 g, 47.0 mmol). The mixture was warmed to 35° C. and stirred for 18 h before partitioning between aqueous sodium bicarbonate (500 mL) and MTBE (500 mL). The organic was washed with water (2×250 mL), dried over sodium sulfate, filtered, and concentrated to provide the title compound. MS: m/z=253.9 (M+1).

Step D: 3-(4-Methoxybenzyl)-1-methylimidazolidine-2,4-dione

To a stirring solution of 1-methylhydantoin (40.0 g, 351 mmol) in DMF (700 mL) at ambient temperature was added 4-methoxybenzyl chloride (49.4 g, 316 mmol) and cesium carbonate (171 g, 526 mmol). The resulting mixture was stirred for 3 days, then partitioned between H$_2$O (2 L) and EtOAc (800 mL). The aqueous layer was extracted further with EtOAc (500 mL) and the combined organic extracts were washed with H$_2$O (2×300 mL), dried over sodium sulfate, filtered, and concentrated in vacuo. The resulting white precipitate was collected by vacuum filtration and washed with MTBE (200 mL) to provide the title compound. MS: m/z=235.2 (M+1).

Step E: 3-Bromo-1'-(4-methoxybenzyl)-3'-methyl-5,7-dihydro-2'H,5'H-spiro[cyclopenta[b]pyridine-6,4'-imidazolidine]-2',5'-dione To a solution of 3-(4-methoxybenzyl)-1-methylimidazolidine-2,4-dione (4.50 g, 19.2 mmol) in 1:1-THF:DMPU (190 mL) at 0° C. was added NaH (1.60 g, 40.4 mmol). After 10 min, a solution of 5-bromo-2,3-bis(chloromethyl)pyridine (4.90 g, 19.2 mmol) in THF (10 mL) was added dropwise, and the reaction mixture was allowed to warm to 10° C. over 1 h. To the reaction mixture was added H₂O (10 mL) dropwise, and the resulting mixture was partitioned between H₂O (500 mL) and EtOAc (500 mL). The aqueous layer was extracted further with EtOAc (3×200 mL) and the combined organic extracts were dried over sodium sulfate, filtered, and concentrated in vacuo. The crude product was purified by silica gel chromatography, eluting with a gradient of heptane:EtOAc 80:20 to 20:80, to give the title compound. MS: m/z=415.9 (M+1).

Step F: Methyl 1'-(4-methoxybenzyl)-3'-methyl-2',5'-dioxo-5,7-dihydrospiro[cyclopenta[b]pyridine-6,4'-imidazolidine]-3-carboxylate To a solution of 3-bromo-1'-(4-methoxybenzyl)-3'-methyl-5,7-dihydro-2'H,5'H-spiro [cyclopenta[b]pyridine-6,4'-imidazolidine]-2',5'-dione (500 mg, 1.2 mmol) in MeOH (12 mL) was added sodium acetate (296 mg, 3.6 mmol) and PdCl₂(dppf)CH₂Cl₂ (196 mg, 0.24 mmol). The resulting mixture was charged in a high-pressure Parr cell which was evacuated and then purged with nitrogen (3×). After the final evacuation the vessel was pressurized with CO to 300 psi. The stirred mixture was heated at 80° C. for 3 days, then diluted with EtOAc (50 mL) and filtered through a plug of silica gel, washing with EtOAc. The filtrate was concentrated in vacuo and the crude product was purified by silica gel chromatography, eluting with a gradient of heptane:EtOAc-90:10 to 0:100, to give the title compound. MS: m/z=396.0 (M+1).

Step G: Methyl 3'-methyl-2',5'-dioxo-5,7-dihydrospiro[cyclopenta[b]pyridine-6,4'-imidazolidine]-3-carboxylate To a solution of methyl 1'-(4-methoxybenzyl)-3'-methyl-2',5'-dioxo-5,7-dihydrospiro[cyclopenta[b]pyridine-6,4'-imidazolidine]-3-carboxylate (100 mg, 0.25 mmol) in acetonitrile (8.4 mL) at ambient temperature was added ceric ammonium nitrate (4.1 g, 7.6 mmol) as a solution in H₂O (5 mL). After 20 min, the reaction mixture was partitioned between H₂O (50 mL) and 9:1-CH₂Cl₂:i-PrOH (50 mL). The aqueous was extracted further with 9:1 CH₂Cl₂:i-PrOH (5×50 mL) and the combined organic extracts were dried over sodium sulfate, filtered, and concentrated in vacuo. The crude solid was washed with MTBE (3×10 mL) then partitioned between saturated aqueous sodium bicarbonate (5 mL) and EtOAc (10 mL). The aqueous layer was extracted further with EtOAc (10 mL) and the combined organic extracts were dried over sodium sulfate, filtered, and concentrated in vacuo to provide the title compound in sufficient purity for use in the next step. MS: m/z=276.1 (M+1).

Step H: 3'-Methyl-2',5'-dioxo-5,7-dihydrospiro[cyclopenta[b]pyridine-6,4'-imidazolidine]-3-carboxylic acid To a solution of methyl 3'-methyl-2',5'-dioxo-5,7-dihydrospiro[cyclopenta[b]pyridine-6,4'-imidazolidine]-3-carboxylate (25 mg, 0.091 mmol) in THF (0.5 mL) and H₂O (0.3 mL) was added 1 N aqueous lithium hydroxide (0.27 mL, 0.27 mmol). The reaction was stirred at ambient temperature for 1 h, acidified by addition of 1 N hydrochloric acid, and concentrated in vacuo to provide the title compound. MS: m/z=262.1 (M+1). ¹H NMR (500 MHz, CDCl₃) δ 8.99 (s, 1H), 8.31 (s, 1H), 3.55 (m, 2H), 3.44 (d, 1H, J=18.3 Hz), 3.42 (d, 1H, J=17.6 Hz), 2.72 (s, 3H).

INTERMEDIATE 9

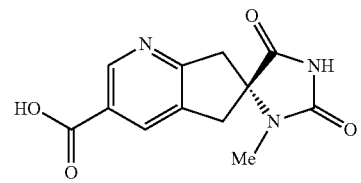 [SMILES: CN1C(=O)NC(=O)[C@]12Cc1cc(C(=O)O)cnc1C2]

(6R)-3'-Methyl-2',5'-dioxo-5,7-dihydrospiro[cyclopenta[b]pyridine-6,4'-imidazolidine]-3-carboxylic acid Step A: Methyl (6R)-1'-(4-methoxybenzyl)-3'-methyl-2',5'-dioxo-5,7-dihydrospiro[cyclopenta[b]pyridine-6,4'-imidazolidine]-3-carboxylate The enantiomers of methyl 1'-(4-methoxybenzyl)-3'-methyl-2',5'-dioxo-5,7-dihydrospiro[cyclopenta[b]pyridine-6,4'-imidazolidine]-3-carboxylate (described in Intermediate 8) were separated by SFC using a ChiralPak IC column, eluting with CO₂:EtOH:CH₃CN-60:20:20, to give methyl (6S)-1'-(4-methoxybenzyl)-3'-methyl-2',5'-dioxo-5,7-dihydrospiro[cyclopenta[b]pyridine-6,4'-imidazolidine]-3-carboxylate, which was the second major peak to elute, and the title compound, which was the first major peak to elute.

Step B: Methyl (6R)-3'-methyl-2',5'-dioxo-5,7-dihydrospiro[cyclopenta[b]pyridine-6,4'-imidazolidine]-3-carboxylate To a stirred solution of methyl (6R)-1'-(4-methoxybenzyl)-3'-methyl-2',5'-dioxo-5,7-dihydrospiro[cyclopenta[b]pyridine-6,4'-imidazolidine]-3-carboxylate (10.0 g, 25.3 mmol) in MeOH (100 mL) at ambient temperature was added ceric ammonium nitrate (27.7 g, 50.6 mmol) and the reaction mixture was stirred at ambient temperature for 18 h. The resulting mixture was partitioned between H₂O (500 mL) and EtOAc (1 L) and the organic layer was discarded. The aqueous layer was adjusted to pH=7-8 by addition of 1 N aqueous NaOH and extracted further with EtOAc (2×500 mL) and the combined organic extracts were dried over sodium sulfate, filtered, and concentrated in vacuo. The crude solid was purified by silica gel chromatography, eluting with a gradient of CH₂Cl₂:MeOH-100:0 to 90:10, to give the title compound. MS: m/z=276.1 (M+1).

Step C: (6R)-3'-Methyl-2',5'-dioxo-5,7-dihydrospiro [cyclopenta[b]pyridine-6,4'-imidazolidine]-3-carboxylic acid To a solution of methyl (6R)-3'-methyl-2',5'-dioxo-5,7-dihydrospiro[cyclopenta[b]pyridine-6,4'-imidazolidine]-3-carboxylate (450 mg, 1.64 mmol) in THF (8 mL) and H₂O (2 mL) was added 1 N aqueous lithium hydroxide (1.96 mL, 1.96 mmol). The reaction was stirred at ambient temperature for 2 h, adjusted to pH 4 by addition of 1 N hydrochloric acid, and concentrated in vacuo to provide the title compound. MS: m/z=262.1 (M+1). ¹H NMR (500 MHz, CD₃OD) δ 8.96 (s, 1H), 8.24 (s, 1H), 3.54 (d, 1H, J=18.1 Hz), 3.52 (d, 1H, J=17.3 Hz), 3.40 (d, 1H, J=17.3 Hz), 3.39 (d, 1H, J=18.1 Hz), 2.71 (s, 3H).

INTERMEDIATE 10

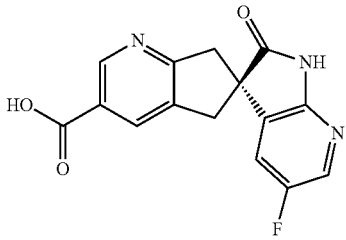 [SMILES: O=C(O)c1cnc2c(c1)C[C@@]1(C2)C(=O)Nc2ncc(F)cc21]

(6S)-5'-Fluoro-2'-oxo-1',2',5,7-tetrahydrospiro[cyclopenta[b]pyridine-6,3'-pyrrolo[2,3-b]pyridine]-3-carboxylic acid Step A: Ethyl (6S)-5'-bromo-2'-oxo-1',2',5,7-tetrahydrospiro[cyclopenta[b]pyridine-6,3'-pyrrolo[2,3-b]pyridine]-3-carboxylate To a solution of (6S)-5'-bromo-2'-oxo-1',2',5,7-tetrahydrospiro [cyclopenta[b]pyridine-6,3'-pyrrolo[2,3-b]pyridine]-3-carboxylic acid (described in Intermediate 6) (6.00 g, 16.7 mmol) in EtOH (250 mL) was added concentrated sulfuric acid (2.22 mL, 41.6 mmol) and the resulting mixture was heated at reflux for 18 h. The reaction mixture was cooled to ambient temperature and the volume was reduced to about 80 mL under reduced pressure. The residual mixture was poured into saturated aqueous sodium bicarbonate (100 mL) and the mixture was extracted with EtOAc (2×150 mL). The combined organic layers were dried over sodium sulfate, filtered, and concentrated to dryness in vacuo. The crude product was purified by silica gel chromatography, eluting with a gradient of CH$_2$Cl$_2$:MeOH 100:0 to 90:10, to give the title compound. MS: m/z=389.9 (M+1).

Step B: Ethyl (6S)-5'-bromo-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate To a solution of ethyl (6S)-5'-bromo-2'-oxo-1',2',5,7-tetrahydrospiro[cyclopenta[b]pyridine-6,3'-pyrrolo[2,3-b]pyridine]-3-carboxylate (3.00 g, 7.73 mmol) in THF (30 mL) at 0° C. was added triethylamine (1.29 mL, 9.28 mmol). The resulting mixture was stirred for 10 min, then 2-(trimethylsilyl)ethoxymethyl chloride (1.64 mL, 9.27 mmol) was added dropwise. The reaction mixture was allowed to warm slowly to ambient temperature and stirring was continued for 4 h. The reaction mixture was poured into saturated aqueous sodium bicarbonate (50 mL) and the mixture was extracted with EtOAc (2×75 mL). The combined organic layers were dried over sodium sulfate, filtered, and concentrated to dryness in vacuo. The crude product was purified by silica gel chromatography, eluting with a gradient of CH$_2$Cl$_2$:EtOAc-100:0 to 50:50, to give the title compound. MS: m/z=520.3 (M+1).

Step C: Ethyl (6S)-2'-oxo-5'-(tributylstannanyl)-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate A stirred mixture of ethyl (6S)-5'-bromo-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate (1.80 g, 3.47 mmol), bis(tributyltin) (10.1 g, 17.4 mmol) and tetrakis(triphenylphosphine)palladium(0) (401 mg, 0.347 mmol) in toluene (25 mL) was heated at 100° C. under an argon atmosphere for 4 h. The reaction mixture was cooled to ambient temperature and partitioned between water (50 mL) and EtOAc (100 mL). The organic layer was washed with brine, dried over sodium sulfate, filtered, and concentrated to dryness in vacuo. The crude product was purified by silica gel chromatography, eluting with a gradient of hexanes:EtOAc 100:0 to 50:50, to give the title compound. MS: m/z=730.7 (M+1).

Step D: Ethyl (6S)-5'-fluoro-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate A stirred mixture of ethyl (6S)-2'-oxo-5'-(tributylstannanyl)-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate (1.00 g, 1.37 mmol), sodium bicarbonate (231 mg, 2.74 mmol), silver(I) oxide (32 mg, 0.137 mmol), N-chloromethyl-N'-fluorotriethylenediammonium bis(tetrafluoroborate) (972 mg, 2.74 mmol), sodium trifluoromethanesulfonate (236 mg, 1.37 mmol) and methanol (0.278 mL, 6.86 mmol) in acetone (50 mL) in a sealed vessel was heated at 65° C. for 4 h. The resulting mixture was cooled to ambient temperature, poured into saturated aqueous sodium bicarbonate (50 mL) and extracted with EtOAc (2×75 mL). The combined organic layers were washed with brine, dried over sodium sulfate, filtered, and concentrated to dryness in vacuo. The crude product was purified by silica gel chromatography, eluting with a gradient of CH$_2$Cl$_2$:EtOAc 100:0 to 50:50, to give the title compound. MS: m/z=458.4 (M+1).

Step E: Ethyl (6S)-5'-fluoro-2'-oxo-1',2',5,7-tetrahydrospiro[cyclopenta[b]pyridine-6,3'-pyrrolo[2,3-b]pyridine]-3-carboxylate A solution of ethyl (6S)-5'-fluoro-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate (300 mg, 0.656 mmol) in MeOH (15 mL) was saturated with HCl (g) and aged for 30 min at ambient temperature. The resulting mixture was concentrated to dryness in vacuo. The residue was dissolved in MeOH (10 mL), ethylenediamine (0.044 mL, 0.656 mmol) was added, and the solution was adjusted to pH 10 by addition of 1 N sodium hydroxide. The resulting mixture was stirred at ambient temperature for 30 min, poured into water (20 mL) and extracted with CHCl$_3$ (2×25 mL). The combined organic layers were washed with brine, dried over sodium sulfate, filtered, and concentrated to dryness in vacuo. The crude product was purified by silica gel chromatography, eluting with a gradient of CH$_2$Cl$_2$:MeOH-100:0 to 90:10, to give the title compound, which contained some of the corresponding methyl ester. MS: m/z=328.2 (M+1).

Step F: (6S)-5'-Fluoro-2'-oxo-1',2',5,7-tetrahydrospiro[cyclopenta[b]pyridine-6,3'-pyrrolo[2,3-b]pyridine]-3-carboxylic acid To a solution of ethyl (6S)-5'-fluoro-2'-oxo-1',2',5,7-tetrahydrospiro[cyclopenta[b]pyridine-6,3'-pyrrolo[2,3-b]pyridine]-3-carboxylate (200 mg, 0.611 mmol) in THF (4 mL) and water (1 mL) was added 1 N lithium hydroxide (0.733 mL, 0.733 mmol) and the resulting mixture was stirred at ambient temperature for 18 h. The reaction mixture was acidified to pH 4 by addition of 1 N hydrochloric acid and concentrated to dryness in vacuo to give the title compound. MS: m/z=300.2 (M+1). $^1$H NMR (500 MHz, CD$_3$OD) δ 9.21 (s, 1H), 8.90 (s, 1H), 8.07 (m, 1H), 7.78 (dd, 1H, J=7.8, 2.7 Hz), 3.87-3.78 (m, 2H), 3.72 (d, 1H, J=17.3 Hz), 3.61 (d, 1H, J=17.6 Hz).

INTERMEDIATE 11

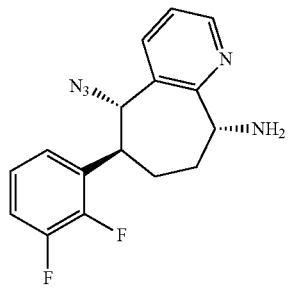 [SMILES: [N-]=[N+]=N[C@@H]1c2cccnc2[C@H](N)CC[C@H]1c1cccc(F)c1F]

(5S,6S,9R)-5-Azido-6-(2,3-difluorophenyl)-6,7,8,9-tetrahydro-5H-cyclohepta[b]pyridin-9-amine Step A: (5S,6S)-5-Azido-6-(2,3-difluorophenyl)-5,6,7,8-tetrahydro-9H-cyclohepta[b]pyridin-9-one To a solution of oxalyl chloride (0.22 mL, 2.6 mmol) in dichloromethane (20 mL) at −15° C. was added DMSO (0.24 mL, 3.4 mmol). The reaction mixture was cooled to −78° C. and a solution of (5S,6S,9R)-5-azido-6-(2,3-difluorophenyl)-6,7,8,9-tetrahydro-5H-cyclohepta[b]pyridin-9-ol (prepared according to the procedures described in WO2011/046997, 270 mg, 0.85 mmol) in dichloromethane (5 mL) was added and the resulting solution was stirred at −78° C. for 2 h. Triethylamine (0.71 mL, 5.1 mmol) was added and the reaction mixture was allowed to warm to ambient temperature and then washed with water (15 mL), dried over sodium sulfate, filtered, and concentrated in vacuo. The residue was purified by silica gel chromatography, eluting with a gradient of hexanes:EtOAc 100:0 to 0:100, to give the title compound. MS: m/z=315.2 (M+1).

Step B: (5S,6S,9R)-5-Azido-6-(2,3-difluorophenyl)-6,7,8,9-tetrahydro-5H-cyclohepta[b]pyridin-9-amine To a solution of (5S,6S)-5-azido-6-(2,3-difluorophenyl)-5,6,7,8-tetrahydro-9H-cyclohepta[b]pyridin-9-one (190 mg, 0.60 mmol), and ammonium acetate (2.3 g, 30 mmol) in MeOH (10 mL) was added sodium cyanoborohydride (27 mg, 0.42 mmol) and the resulting mixture was stirred at ambient temperature for 16 h. The reaction mixture was concentrated under reduced pressure and the residue was partitioned between dichloromethane (20 mL) and aqueous 1 N NaOH solution (5 mL). The organic layer was separated, dried over sodium sulfate, filtered, and concentrated in vacuo. The residue was purified by silica gel chromatography, eluting with a gradient of EtOAc:MeOH:Et$_3$N-100:0:0 to 85:10:5, to give the title compound as a mixture of diastereomers. MS: m/z=316.2 (M+1).

INTERMEDIATE 12

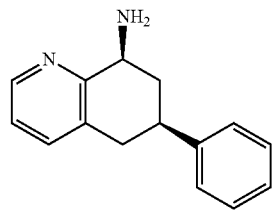 [SMILES: N[C@H]1C[C@@H](c2ccccc2)Cc2cccnc21]

(6S,8S & 6R,8R)-6-Phenyl-5,6,7,8-tetrahydroquinolin-8-amine

Step A: 6-Phenyl-6,7-dihydroquinolin-8(5H)-one

To a stirred suspension of AlBr$_3$ (4.80 g, 18 mmol) in benzene (4.8 mL, 55 mmol) was added 8-hydroxyquinoline (0.50 g, 3.4 mmol). The resulting mixture was saturated with HBr (g) and then stirred at 40° C. for 48 h. The reaction mixture was cooled to ambient temperature and poured onto ice (50 g). The resulting mixture was adjusted to pH=1-2 by addition of concentrated HCl and then was extracted with EtOAc (3×20 mL), discarding the organic extracts. The aqueous layer was adjusted to pH 12 by addition of NaOH (s), keeping the temperature below 10° C., and was then extracted with EtOAc (3×20 mL). These combined organic extracts were washed with brine (30 mL), dried over sodium sulfate, filtered, and concentrated in vacuo to give the title compound in sufficient purity for use in the next step. MS: m/z=223.8 (M+1).

Step B: tert-Butyl (6-phenyl-5,6,7,8-tetrahydroquinolin-8-yl)carbamate

To a solution of 6-phenyl-6,7-dihydroquinolin-8(5H)-one (1.07 g, 4.80 mmol) in EtOH (30 mL) were added NH$_4$OAc (5.67 g, 73.6 mmol) and NaBH$_3$CN (377 mg, 6.0 mmol). The resulting mixture was purged with nitrogen and then heated at 130° C. in a microwave reactor for 10 min. The cooled reaction mixture was concentration in vacuo and the residue was partitioned between EtOAc (30 mL) and H$_2$O (10 mL). The organic layer was washed with brine (10 mL), dried over sodium sulfate, filtered, and concentrated in vacuo. The residue was dissolved in MeOH (10 mL) and to the solution were added di-tert-butyl dicarbonate (324 mg, 1.48 mmol) and triethylamine (0.3 mL, 2.2 mmol). The resulting mixture was stirred at ambient temperature for 1 h, and then purified by reversed-phase HPLC on a C-18 column, eluting with a gradient of H$_2$O:CH$_3$CN:TFA-82:18:0.062 to 52:48:0.039, to afford the title compound as a mixture of cis and trans isomers in approximately a 3:1 ratio. MS: m/z=325.1 (M+1).

Step C: (6S,8S & 6R,8R)-6-Phenyl-5,6,7,8-tetrahydroquinolin-8-amine

A solution of tert-butyl (6-phenyl-5,6,7,8-tetrahydroquinolin-8-yl)carbamate (500 mg, 1.54 mmol) in 4 N HCl in MeOH (5 mL) was aged at ambient temperature for 30 min and then concentrated to dryness in vacuo. The residue was purified by reversed-phase HPLC on a C-18 column, eluting with a gradient of H₂O:CH₃CN:TFA-85:15:0.064 to 75:25: 0.056, to afford the racemic trans isomer of the product amine, (6R,8S & 6S,8R)-6-phenyl-5,6,7,8-tetrahydroquinolin-8-amine, and the racemic cis isomer of the product amine, the title compound. MS: m/z=224.9 (M+1). ¹H NMR (400 MHz, CD₃OD) δ 8.51 (d, 1H, J=4.8 Hz), 7.65 (d, 1H, J=7.6 Hz), 7.38-7.27 (m, 6H), 4.49 (dd, 1H, J=11.6, 6.0 Hz), 3.27 (m, 1H), 3.15-3.01 (m, 2H), 2.51 (m, 1H), 2.11 (m, 1H).

INTERMEDIATE 13

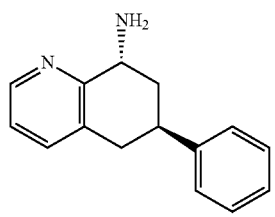 [SMILES: N[C@@H]1C[C@@H](c2ccccc2)Cc2cccnc21]

(6R,8S & 6S,8R)-6-Phenyl-5,6,7,8-tetrahydroquinolin-8-amine

The racemic trans isomer, (6R,8S & 6S,8R)-6-phenyl-5,6,7,8-tetrahydroquinolin-8-amine was isolated in the procedure described in Intermediate 12. MS: m/z=224.9 (M+1). ¹H NMR (400 MHz, CD₃OD) δ 8.54 (d, 1H, J=3.6 Hz), 7.75 (d, 1H, J=8.0 Hz), 7.39-7.22 (m, 6H), 4.37 (t, 1H, J=5.6 Hz), 3.40-3.10 (m, 3H), 2.58 (ddd, 1H, J=16.4, 10.4, 6.0 Hz), 2.33 (m, 1H).

INTERMEDIATE 14

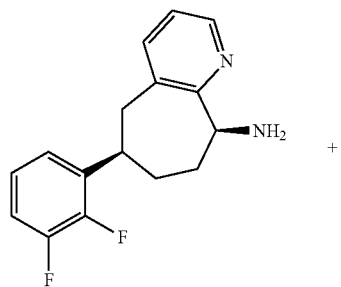

(6R,9S and 6S,9R)-6-(2,3-Difluorophenyl)-6,7,8,9-tetrahydro-5H-cyclohepta[b]pyridin-9-amine and (6S,9S and 6R,9R)-6-(2,3-difluorophenyl)-6,7,8,9-tetrahydro-5H-cyclohepta[b]pyridin-9-amine Step A: 6-(2,3-Difluorophenyl)-7,8-dihydro-5H-cyclohepta[b]pyridin-9(6H)-one To a solution of oxalyl chloride (0.91 mL, 11 mmol) in dichloromethane (15 mL) at −65° C. was added DMSO (0.94 mL, 13 mmol), and the mixture was stirred for 30 min. A solution of racemic trans 6-(2,3-difluorophenyl)-6,7,8,9-tetrahydro-5H-cyclohepta[b]pyridin-9-ol (prepared according to the procedures described by Leahy, D. K et al *Org. Lett.* 2012, 14, 4938-4941, 365 mg, 1.33 mmol) in dichloromethane (3 mL) was added drop wise and the resulting solution was stirred at −65° C. for 30 min. Triethylamine (2.55 mL, 18.6 mmol) was added and the reaction mixture was gradually warmed to 23° C. over a period of 4 h, and then partitioned between water and dichloromethane. The organic layer was washed with water (3×), brine, dried over sodium sulfate, and concentrated in vacuo. The residue was purified by flash chromatography on silica gel, eluting with 35% ethyl acetate in petroleum ether to give the title compound as a racemic mixture. MS: m/z=274.2 (M+1).

Step B: (6R,9S and 6S,9R)-6-(2,3-Difluorophenyl)-6,7,8,9-tetrahydro-5H-cyclohepta[b]pyridin-9-amine and (6S,9S and 6R,9R)-6-(2,3-difluorophenyl)-6,7,8,9-tetrahydro-5H-cyclohepta[b]pyridin-9-amine Sodium cyanoborohydride (0.043 g, 0.69 mmol) was added to a mixture of 6-(2,3-difluorophenyl)-7,8-dihydro-5H-cyclohepta[b]pyridin-9(6H)-one (0.27 g, 0.99 mmol) and ammonium acetate (3.8 g, 49 mmol) in methanol (14 mL). The resulting mixture was stirred at 23° C. for 16 h, then concentrated under reduced pressure. The residue was dried by azeotropic distillation (toluene), then triturated with dichloromethane and filtered. The filter cake was thoroughly washed with dichloromethane. The filtrate was washed with brine, dried over anhydrous sodium sulfate, and concentrated. The residue was purified by preparative chromatography to give the title compounds as a mixture of cis and trans isomers. MS: m/z=275.2 (M+1).

INTERMEDIATE 15

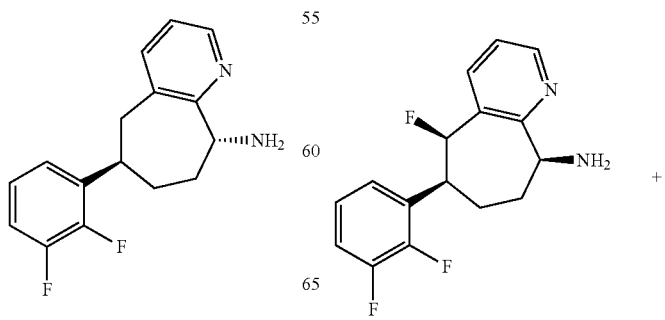

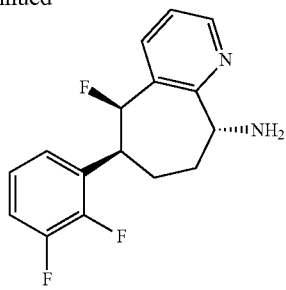

(5R,6S,9S and 5S,6R,9R)-6-(2,3-Difluorophenyl)-5-fluoro-6,7,8,9-tetrahydro-5H-cyclohepta[b]pyridin-9-amine and (5R,6S,9R and 5S,6R,9S)-6-(2,3-difluorophenyl)-5-fluoro-6,7,8,9-tetrahydro-5H-cyclohepta[b]pyridin-9-amine Step A: (5R,6S,9R and 5S,6R,9S)-6-(2,3-Difluorophenyl)-5-fluoro-9-((triisopropylsilyl)oxy)-6,7,8,9-tetrahydro-5H-cyclohepta[b]pyridine Deoxo-Fluor® (0.148 g, 0.670 mmol) was added dropwise to a solution of (5S,6S,9R and 5R,6R,9S)-6-(2,3-difluorophenyl)-9-((triisopropylsilyl)oxy)-6,7,8,9-tetrahydro-5H-cyclohepta[b]pyridin-5-ol (prepared according to the procedures described by Leahy, D. K et al Org. Lett. 2012, 14, 4938-4941, 0.30 g, 0.67 mmol) and triethylamine (0.093 mL, 0.67 mmol) in 1,2-dichloroethane (2 mL) at 0° C. The resulting mixture was gradually warmed to 23° C. and stirred for 2 h, then partitioned between saturated aqueous sodium bicarbonate solution and dichloromethane (3×). The combined organic layers were washed with brine, dried over anhydrous sodium sulfate, and concentrated. The residue was purified by flash chromatography on silica gel, eluting with 35% dichloromethane in petroleum ether to give the title compound as a racemic mixture. MS: m/z=450.2 (M+1).

Step B: (5R,6S,9R and 5S,6R,9S)-6-(2,3-Difluorophenyl)-5-fluoro-6,7,8,9-tetrahydro-5H-cyclohepta[b]pyridin-9-ol Pyridine hydrofluoride (0.037 g, 0.38 mmol) was added dropwise to a solution of (5R,6S,9R and 5S,6R,9S)-6-(2,3-difluorophenyl)-5-fluoro-9-((triisopropylsilyl)oxy)-6,7,8,9-tetrahydro-5H-cyclohepta[b]pyridine (0.155 g, 0.345 mmol) in tetrahydrofuran (3 mL) cooled to 0° C., and the mixture was stirred for 3 h. The reaction mixture was partitioned between saturated aqueous sodium bicarbonate solution and ethyl acetate (3×). The combined organic layers were washed with brine, dried over anhydrous sodium sulfate, and concentrated. The residue was purified by flash chromatography on silica gel, eluting with 55% dichloromethane in petroleum ether to give the title compound as a racemic mixture. MS: m/z=294.2 (M+1).

Step C: (5R,6S and 5S,6R)-6-(2,3-Difluorophenyl)-5-fluoro-7,8-dihydro-5H-cyclohepta[b]pyridin-9(6H)-one To a solution of oxalyl chloride (1.2 g, 9.5 mmol) in dichloromethane (15 mL) at −65° C. was added DMSO (0.85 mL, 12 mmol), and the mixture was stirred for 30 min. A solution of 5R,6S,9R and 5S,6R,9S)-6-(2,3-difluorophenyl)-5-fluoro-6,7,8,9-tetrahydro-5H-cyclohepta[b]pyridin-9-ol (0.35 g, 1.9 mmol) in dichloromethane (3 mL) was added dropwise and the resulting solution was stirred at −65° C. for 30 min. After triethylamine (2.3 mL, 17 mmol) was added, the reaction mixture was gradually warmed to 23° C. over a period of 4 h, and then partitioned between water and dichloromethane. The organic layer was washed with water (3×), brine, dried over sodium sulfate, and concentrated in vacuo. The residue was purified by flash chromatography on silica gel, eluting with 50% ethyl acetate in petroleum ether to give the title compound as a racemic mixture. MS: m/z=292.2 (M+1).

Step D: (5R,6S,9S and 5S,6R,9R)-6-(2,3-Difluorophenyl)-5-fluoro-6,7,8,9-tetrahydro-5H-cyclohepta[b]pyridin-9-amine and (5R,6S,9R and 5S,6R,9S)-6-(2,3-difluorophenyl)-5-fluoro-6,7,8,9-tetrahydro-5H-cyclohepta[b]pyridin-9-amine Sodium cyanoborohydride (0.043 g, 0.69 mmol) was added to a mixture of (5R,6S and 5S,6R)-6-(2,3-difluorophenyl)-5-fluoro-7,8-dihydro-5H-cyclohepta[b]pyridin-9(6H)-one (0.35 g, 1.2 mmol) and ammonium acetate (4.63 g, 60.1 mmol) in methanol (18 mL). The resulting mixture was stirred at 23° C. for 16 h, then concentrated. The residue was dried by azeotropic distillation (toluene), then triturated with dichloromethane and filtered. The filter cake was thoroughly washed with dichloromethane. The filtrate was washed with brine, dried over anhydrous sodium sulfate, and concentrated. The residue was purified by preparative chromatography to give the title compounds as a mixture of four isomers. MS: m/z=293.0 (M+1).

INTERMEDIATE 16

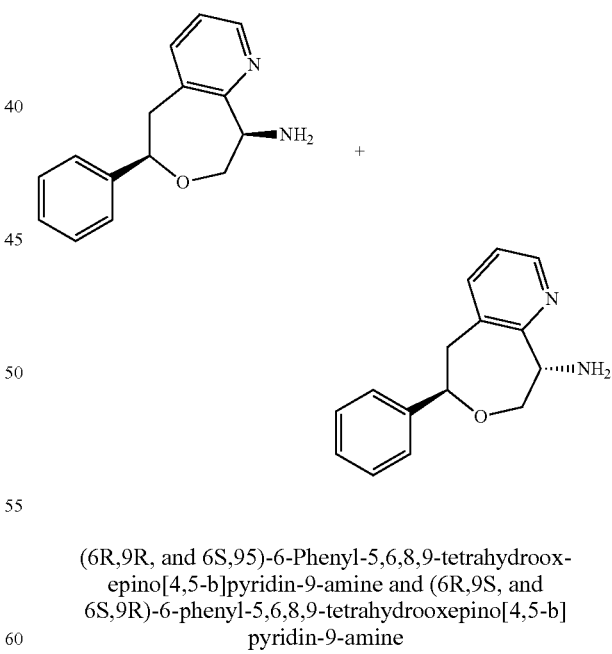

(6R,9R, and 6S,9S)-6-Phenyl-5,6,8,9-tetrahydrooxepino[4,5-b]pyridin-9-amine and (6R,9S, and 6S,9R)-6-phenyl-5,6,8,9-tetrahydrooxepino[4,5-b]pyridin-9-amine Step A: 2-(2-Bromopyridin-3-yl)-1-phenylethanol A solution of n-butyllithium in hexanes (2.5 M, 27.9 mL, 0.0698 mol) was added dropwise over a period of 30 min to a solution of N,N-diisopropylamine (9.9 mL, 0.069 mol, 1.2 equiv) in anhydrous THF (40 mL) at −78° C. The resulting mixture was slowly warmed to 5° C. over 30 min, then cooled to −78° C., and a solution of 2-bromo-3-methylpyridine (6.5 mL, 0.058 mol) in anhydrous THF (20 mL) was added dropwise over 45 min and stirred for 1 h. A solution of benzaldehyde (7.1 mL, 0.069 mol) in THF (20 mL) was then added dropwise over 15 min. The resulting solution was gradually warmed to 23° C. The reaction mixture was quenched with saturated aqueous ammonium chloride solution, and extracted with ethyl acetate (2×). The combined organic layers were washed with brine, dried over anhydrous sodium sulfate, and concentrated. The residue was purified by flash chromatography on silica gel eluting with 25% ethyl acetate in petroleum ether to give the title compound. MS: m/z=280.0 (M+1).

Step B: Methyl 2-(2-(2-bromopyridin-3-yl)-1-phenylethoxy)acetate

A solution of 2-(2-bromopyridin-3-yl)-1-phenylethanol (2.5 g, 9.0 mmol) in anhydrous DMF (10 mL) was added dropwise to a suspension of sodium hydride (60% dispersion in mineral oil, 0.54 g, 13 mmol) in anhydrous DMF (10 mL) at 0° C., and the resulting mixture was stirred for 30 min. Methyl bromoacetate (1.03 mL, 10.7 mmol) was added, and the contents were warmed to 23° C. and stirred for 30 min, then partitioned between ethyl acetate and water (2×). The combined organic layers were washed with brine, dried over anhydrous sodium sulfate, and concentrated. The residue was purified by flash chromatography on silica gel eluting with 20% ethyl acetate in petroleum ether to give the title compound. MS: m/z=352.0 (M+1).

Step C: Methyl 3-(2-(2-methoxy-2-oxoethoxy)-2-phenylethyl)picolinate

A stream of CO gas was bubbled through a mixture of methyl 2-(2-(2-bromopyridin-3-yl)-1-phenylethoxy)acetate (6.5 g, 18 mmol), sodium acetate (4.6 g, 55 mmol) and 1,1'-bis(diphenylphosphino)ferrocene-palladium(II)dichloride dichloromethane complex (3.0 g, 3.7 mmol) in anhydrous methanol (650 mL) at 70° C. for 4 h. The reaction mixture was cooled to 23° C. and concentrated. The residue was dissolved ethyl acetate (200 mL) and filtered through Celite®. The filtrate was concentrated and the residue was purified by flash chromatography on silica gel eluting with 40% ethyl acetate in petroleum ether to give the title compound. MS: m/z=330.2 (M+1).

Step D: Methyl 9-hydroxy-6-phenyl-5,6-dihydrooxepino[4,5-b]pyridine-8-carboxylate A solution of potassium tert-butoxide in THF (1M, 10 mL, 10 mmol), was added dropwise to a solution of methyl 3-(2-(2-methoxy-2-oxoethoxy)-2-phenylethyl)picolinate (3.0 g, 9.1 mmol) in xylene (20 mL) at 28° C. The resulting mixture was heated at 82° C. for 2 h, then cooled and concentrated. The residue was partitioned between ethyl acetate and saturated aqueous ammonium chloride solution. The organic layer was washed with brine, dried over anhydrous sodium sulfate, and concentrated. The residue was purified by flash chromatography on silica gel eluting with 40% ethyl acetate in petroleum ether to give the title compound. MS: m/z=298.2 (M+1).

Step E: 6-Phenyl-5,6-dihydrooxepino[4,5-b]pyridin-9(8H)-one

Sodium chloride (0.10 g, 1.7 mmol) was added to a solution of methyl 9-hydroxy-6-phenyl-5,6-dihydrooxepino[4,5-b]pyridine-8-carboxylate (0.50 g, 1.7 mmol) in dimethylsulfoxide (8 mL) and water (0.4 mL). The resulting mixture was heated at 150° C. for 2 h, then cooled and partitioned between water and ethyl acetate (3×). The combined organic layers were washed with brine, dried over anhydrous sodium sulfate, and concentrated. The residue was purified by flash chromatography on silica gel eluting with 40% ethyl acetate in petroleum ether to give the title compound. MS: m/z=240.0 (M+1).

Step F: (6R,9R, and 6S,9S)-6-Phenyl-5,6,8,9-tetrahydrooxepino[4,5-b]pyridin-9-amine and (6R,9S, and 6S,9R)-6-phenyl-5,6,8,9-tetrahydrooxepino[4,5-b]pyridin-9-amine A mixture of 6-phenyl-5,6-dihydrooxepino[4,5-b]pyridin-9(8H)-one (0.69 g, 2.9 mmol), potassium carbonate (1.19 g, 8.65 mmol), and hydroxylamine hydrochloride (0.24 g, 3.46 mmol) in anhydrous methanol (35 mL) was stirred at 23° C. for 8 h, and then filtered. The filter cake was washed with methanol (10 mL). The filtrate was treated with zinc dust (1.5 g, 23 mmol) and ammonium chloride (1.2 g, 23 mmol). The resulting suspension was stirred at 23° C. for 20 h, then filtered. The filter cake was washed with methanol. The filtrate was concentrated and the residue was purified by reverse phase preparative HPLC (C18 column), eluting with 30% in methanol in water (0.1% TFA used as a modifier) initially, grading to 100% methanol, to give the title compound as separated mixture of cis and trans isomers.

Isomer set A (1$^{st}$ to elute): MS: m/z=241.2 (M+1); $^1$H NMR (400 MHz, CD$_3$OD) δ 8.53 (dd, 1H, J=1.5, 4.9 Hz), 7.55-7.60 (m, 1H), 7.36 (dd, 1H, J=4.8, 7.7 Hz), 7.25-7.34 (m, 5H), 4.93-4.98 (m, 1H), 4.83 (t, 1H, J=4.0 Hz), 4.32 (dd, 1H, J=3.6, 13.7 Hz), 4.24 (dd, 1H, J=4.6, 13.7 Hz), 3.39-3.47 (m, 2H).

Isomer set B (2$^{nd}$ to elute): MS: m/z=241.2 (M+1); $^1$H NMR (400 MHz, CD$_3$OD) δ 8.51 (d, 1H, J=4.3 Hz), 7.74 (d, 1H, J=7.9 Hz), 7.44-7.48 (m, 2H), 7.29-7.40 (m, 4H), 4.96-5.01 (m, 1H), 4.55 (d, 1H, J=10.0 Hz), 4.37 (dd, 1H, J=1.8, 12.0 Hz), 3.83 (dd, 1H, J=9.5, 12.0 Hz), 3.53 (dd, 1H, J=11.0, 15.6 Hz), 3.04 (d, 1H, J=15.6 Hz).

EXAMPLE 1

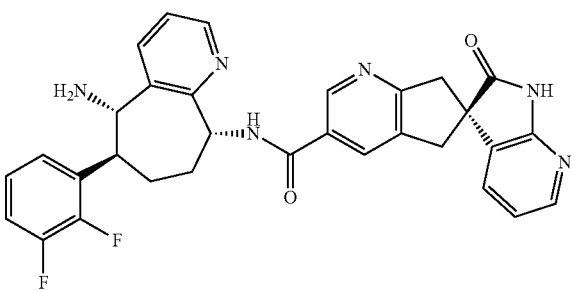 [SMILES: N[C@@H]1c2cccnc2[C@H](NC(=O)c2cnc3c(c2)C[C@@]2(C3)C(=O)Nc3ncccc32)CC[C@H]1c1cccc(F)c1F]

(6S)—N-[(5S,6S,9R)-5-Amino-6-(2,3-difluorophe-
nyl)-6,7,8,9-tetrahydro-5H-cyclohepta[b]pyridin-9-
yl]-2'-oxo-1',2',5,7-tetrahydrospiro[cyclopenta[b]
pyridine-6,3'-pyrrolo[2,3-b]pyridine]-3-carboxamide Step A: (6S)—N-[(5S,6S,9R)-5-Azido-6-(2,3-difluo-
rophenyl)-6,7,8,9-tetrahydro-5H-cyclohepta[b]pyri-
din-9-yl]-2'-oxo-1',2',5,7-tetrahydrospiro[cyclopenta
[b]pyridine-6,3'-pyrrolo[2,3-b]pyridine]-3-
carboxamide To a solution of (5S,6S,9R)-5-azido-6-(2,3-difluorophe-
nyl)-6,7,8,9-tetrahydro-5H-cyclohepta[b]pyridin-9-amine
(the mixture of diastereomers described in Intermediate 11)
(90 mg, 0.28 mmol), (6S)-2'-oxo-1',2',5,7-tetrahydrospiro
[cyclopenta[b]pyridine-6,3'-pyrrolo[2,3-b]pyridine]-3-car-
boxylic acid (described in Intermediate 4) (85 mg, 0.30
mmol) and HATU (2-(7-aza-1H-benzotriazol-1-yl)-1,1,3,3-
tetramethyluronium hexafluorophosphate) (160 mg, 0.43
mmol) in DMF (3.0 mL) was added N,N-diisopropylethy-
lamine (0.15 mL, 0.86 mmol), and the resulting mixture was
stirred at ambient temperature for 16 h. The reaction mixture
was partially purified by reversed-phase HPLC on a C-18
column, eluting with a gradient of $H_2O:CH_3CN:TFA$-100:0:
0.1 to 0:100:0.1. Product-containing fractions were com-
bined and neutralized with saturated aqueous sodium carbon-
ate and the acetonitrile was removed by evaporation under
reduced pressure. The resulting mixture was extracted with
ethyl acetate (50 mL) and dichloromethane (2×50 mL) and
the combined organic layers were dried over sodium sulfate,
filtered, and concentrated under reduced pressure to give the
title compound as a mixture of four diastereomers. Separation
of the diastereomers was achieved by SFC on a ChiralCel
OJ-H column, eluting with $CO_2$:MeOH-80:20, to give four
diastereomers in approximately a 2:1:2:5 ratio:

Diastereomer 1 (1$^{st}$ peak to elute): (6S)—N-[(5S,6S,9S)-
5-Azido-6-(2,3-difluorophenyl)-6,7,8,9-tetrahydro-5H-cy-
clohepta[b]pyridin-9-yl]-2'-oxo-1',2',5,7-tetrahydrospiro
[cyclopenta[b]pyridine-6,3'-pyrrolo[2,3-b]pyridine]-3-car-
boxamide. MS: m/z=579.3 (M+1).

Diastereomer 2 (2$^{nd}$ peak to elute): (6S)—N-[(5R,6S,9R)-
5-Azido-6-(2,3-difluorophenyl)-6,7,8,9-tetrahydro-5H-cy-
clohepta[b]pyridin-9-yl]-2'-oxo-1',2',5,7-tetrahydrospiro
[cyclopenta[b]pyridine-6,3'-pyrrolo[2,3-b]pyridine]-3-
carboxamide. MS: m/z=579.3 (M+1).

Diastereomer 3 (3$^{rd}$ peak to elute): (6S)—N-[(5R,6S,9S)-
5-Azido-6-(2,3-difluorophenyl)-6,7,8,9-tetrahydro-5H-cy-
clohepta[b]pyridin-9-yl]-2'-oxo-1',2',5,7-tetrahydrospiro
[cyclopenta[b]pyridine-6,3'-pyrrolo[2,3-b]pyridine]-3-car-
boxamide. MS: m/z=579.3 (M+1).

Diastereomer 4 (4$^{th}$ peak to elute): (6S)—N-[(5S,6S,9R)-
5-Azido-6-(2,3-difluorophenyl)-6,7,8,9-tetrahydro-5H-cy-
clohepta[b]pyridin-9-yl]-2'-oxo-1',2',5,7-tetrahydrospiro
[cyclopenta[b]pyridine-6,3'-pyrrolo[2,3-b]pyridine]-3-
carboxamide, the title compound. MS: m/z=579.3 (M+1). $^1$H
NMR (600 MHz, DMSO-$d_6$) δ 11.13 (s, 1H); 9.09 (d, 1H,
J=7.1 Hz); 8.96 (s, 1H); 8.55 (d, 1H, J=4.8 Hz); 8.18 (s, 1H);
8.10 (dd, 1H, J=5.3, 1.5 Hz); 7.96 (d, 1H, J=7.8 Hz); 7.52 (m,
2H); 7.44 (dd, 1H, J=7.8, 4.8 Hz); 7.37 (m, 1H); 7.31-7.26 (m,
1H); 6.96 (dd, 1H, J=7.3, 5.3 Hz); 5.86 (d, 1H, J=10.4 Hz);
5.60 (t, 1H, J=8.7 Hz); 3.45-3.33 (m, 4H); 3.04 (td, 1H,
J=10.6, 3.5 Hz); 2.40 (m, 1H); 2.24 (m, 1H); 1.94 (m, 1H);
1.63 (m, 1H).

Step B: (6S)—N-[(5S,6S,9R)-5-Amino-6-(2,3-dif-
luorophenyl)-6,7,8,9-tetrahydro-5H-cyclohepta[b]
pyridin-9-yl]-2'-oxo-1',2',5,7-tetrahydrospiro[cyclo-
penta[b]pyridine-6,3'-pyrrolo[2,3-b]pyridine]-3-
carboxamide (6S)—N-[(5S,6S,9R)-5-Azido-6-(2,3-difluorophenyl)-6,
7,8,9-tetrahydro-5H-cyclohepta[b]pyridin-9-yl]-2'-oxo-1',2',
5,7-tetrahydrospiro[cyclopenta[b]pyridine-6,3'-pyrrolo[2,3-
b]pyridine]-3-carboxamide (13 mg, 0.022 mmol) was
azeotroped with dry toluene and dried under high vacuum.
The azide was dissolved in THF (1 mL), trimethylphosphine
(1 M in toluene, 0.25 mL, 0.25 mmol) was added, and the
resulting solution was stirred at ambient temperature for 1.5
h. The reaction solution was concentrated to dryness in vacuo,
resuspended in THF (2 mL) and water (0.5 mL) and heated at
85° C. in a sealed vial for 4 h. The mixture was allowed to
cool, most of the THF was removed by evaporation and the
residual solution was purified by reversed-phase HPLC on a
C-18 column, eluting with a gradient of $H_2O:CH_3CN:TFA$-
95:5:0.1 to 0:100:0.1. Product-containing fractions were
combined and neutralized with saturated aqueous sodium
bicarbonate and the acetonitrile was removed by evaporation
under reduced pressure. The resulting mixture was extracted
with ethyl acetate (2×50 mL) and the combined organic layers
were dried over sodium sulfate, filtered, and concentrated
under reduced pressure to give the title compound. MS:
m/z=553.3 (M+1). 1H NMR (400 MHz, $CD_3OD$) δ 8.95 (d,
1H, J=2.0 Hz); 8.48 (dd, 1H, J=4.9, 1.6 Hz); 8.24 (d, 1H,
J=2.0 Hz); 8.08 (dd, 1H, J=5.3, 1.6 Hz); 8.00 (d, 1H, J=7.9
Hz); 7.42-7.35 (m, 2H); 7.28 (s, 1H); 7.25-7.15 (m, 2H); 6.96
(dd, 1H, J=7.4, 5.3 Hz); 5.58 (dd, 1H, J=10.1, 3.3 Hz); 4.74 (d,
1H, J=9.4 Hz); 3.65-3.55 (m, 2H); 3.40-3.30 (m, 2H); 3.06 (br
s, 1H); 2.41-2.24 (m, 2H); 2.04-1.94 (m, 1H); 1.71-1.53 (m
1H).

EXAMPLE 2

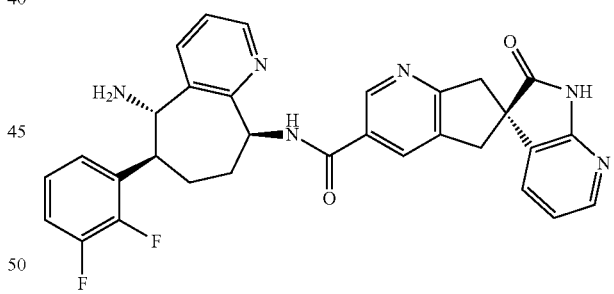

(6S)—N-[(5S,6S,9S)-5-Amino-6-(2,3-difluorophe-
nyl)-6,7,8,9-tetrahydro-5H-cyclohepta[b]pyridin-9-
yl]-2'-oxo-1',2',5,7-tetrahydrospiro[cyclopenta[b]
pyridine-6,3'-pyrrolo[2,3-b]pyridine]-3-carboxamide Essentially following the procedures described in Example
1, but using (6S)—N-[(5S,6S,9S)-5-azido-6-(2,3-difluo-
rophenyl)-6,7,8,9-tetrahydro-5H-cyclohepta[b]pyridin-9-
yl]-2'-oxo-1',2',5,7-tetrahydrospiro[cyclopenta[b]pyridine-
6,3'-pyrrolo[2,3-b]pyridine]-3-carboxamide (described in
Example 1) in place of (6S)—N-[(5S,6S,9R)-5-azido-6-(2,3-
difluorophenyl)-6,7,8,9-tetrahydro-5H-cyclohepta[b]pyri-
din-9-yl]-2'-oxo-1',2',5,7-tetrahydrospiro[cyclopenta[b]py-
ridine-6,3'-pyrrolo[2,3-b]pyridine]-3-carboxamide, the title compound was obtained. MS: m/z=553.3 (M+1). ¹H NMR (400 MHz, CD₃OD) δ 8.96 (d, 1H, J=2.0 Hz); 8.50 (dd, 1H, J=4.9, 1.7 Hz); 8.23 (s, 1H); 8.08 (dd, 1H, J=5.3, 1.6 Hz); 7.73 (dd, 1H, J=7.6, 1.7 Hz); 7.40-7.32 (m, 2H); 7.16-7.06 (m, 3H); 6.96 (dd, 1H, J=7.4, 5.3 Hz); 5.81 (dd, 1H, J=10.6, 5.8 Hz); 4.38 (d, 1H, J=7.2 Hz); 3.65-3.55 (m, 2H); 3.44 (t, 1H, J=8.0 Hz); 3.34-3.24 (m, 2H); 2.52-2.38 (m, 1H); 2.01-1.74 (m, 3H).

EXAMPLE 3

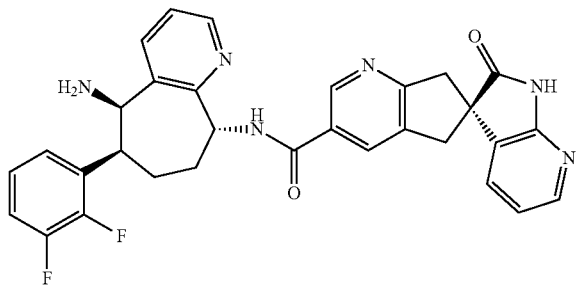 [SMILES: N[C@H]1c2cccnc2[C@H](NC(=O)c2cnc3c(c2)C[C@@]2(C3)C(=O)Nc3ncccc32)CC[C@H]1c1cccc(F)c1F]

(6S)—N-[(5R,6S,9R)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide Essentially following the procedures described in Example 1, but using (6S)—N-[(5R,6S,9R)-5-azido-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide (described in Example 1) in place of (6S)—N-[(5S,6S,9R)-5-azido-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide, the title compound was obtained. MS: m/z=553.3 (M+1). ¹H NMR (400 MHz, CD₃OD) δ 8.95 (d, 1H, J=2.0 Hz); 8.50 (dd, 1H, J=4.9, 1.7 Hz); 8.24 (s, 1H); 8.09 (dd, 1H, J=5.3, 1.6 Hz); 7.71 (d, 1H, J=7.6 Hz); 7.39 (dd, 1H, J=7.4, 1.6 Hz); 7.31 (m, 2H); 7.19 (m, 2H); 6.96 (dd, 1H, J=7.4, 5.3 Hz); 5.81 (dd, 1H, J=10.9, 1.2 Hz); 4.31 (s, 1H); 3.60 (dd, 2H, J=17.1, 6.0 Hz); 3.49-3.41 (m, 1H); 3.35 (dd, 2H, J=17.1, 3.2 Hz); 2.48 (m, 1H); 2.05-1.93 (m, 2H); 1.58 (m, 1H).

EXAMPLE 4

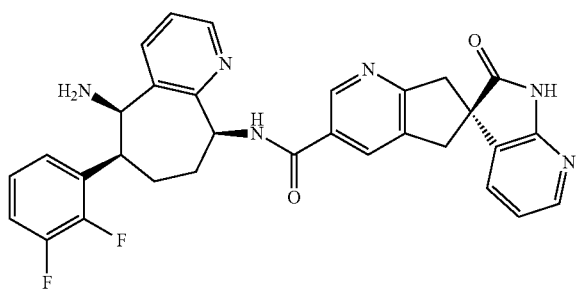 [SMILES: N[C@H]1c2cccnc2[C@@H](NC(=O)c2cnc3c(c2)C[C@@]2(C3)C(=O)Nc3ncccc32)CC[C@H]1c1cccc(F)c1F]

(6S)—N-[(5R,6S,9S)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide Essentially following the procedures described in Example 1, but using (6S)—N-[(5R,6S,9S)-5-azido-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide (described in Example 1) in place of (6S)—N-[(5S,6S,9R)-5-azido-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide, the title compound was obtained. MS: m/z=553.3 (M+1). 1H NMR (400 MHz, CD₃OD) δ 8.89 (s, 1H); 8.41 (s, 1H); 8.19 (s, 1H); 8.07 (dd, J=5.3, 1.6 Hz, 1H); 7.76 (m, 1H); 7.37-7.32 (m, 2H); 7.17 (m, 3H); 6.94 (dd, J=7.4, 5.3 Hz, 1H); 5.76 (m, 1H); 4.30 (br s, 1H); 3.63-3.45 (m, 3H); 3.34-3.25 (m, 2H); 2.37 (br s, 1H); 2.10-1.94 (m, 2H); 1.58 (m, 1H).

EXAMPLE 5

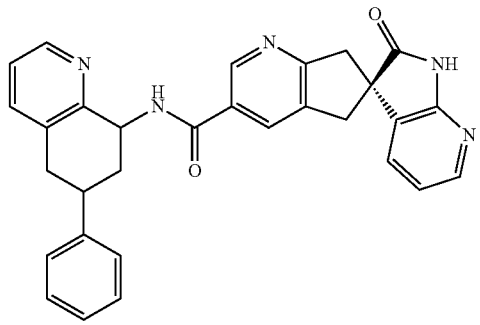 [SMILES: O=C(NC1CC(c2ccccc2)Cc2cccnc21)c1cnc2c(c1)C[C@@]1(C2)C(=O)Nc2ncccc21]

(6S)-2'-Oxo-N-(6-phenyl-5,6,7,8-tetrahydroquinolin-8-yl)-1',2',5,7-tetrahydrospiro[cyclopenta[b]pyridine-6,3'-pyrrolo[2,3-b]pyridine]-3-carboxamide, isomers A & B To a stirred solution of (6S)-2'-oxo-1',2',5,7-tetrahydrospiro [cyclopenta[b]pyridine-6,3'-pyrrolo[2,3-b]pyridine]-3-carboxylic acid (described in Intermediate 4) (83 mg, 0.29 mmol) in DMF (2 mL) were added EDC (82 mg, 0.33 mmol), HOBT (44 mg, 0.33 mmol), and N,N-diisopropylethylamine (0.066 mL, 0.41 mmol). The mixture was stirred at ambient temperature for 10 min, then (6S,8S & 6R,8R)-6-phenyl-5,6,7,8-tetrahydroquinolin-8-amine (described in Intermediate 12) (60 mg, 0.27 mmol) was added, and the resulting mixture was stirred at ambient temperature for 16 h. The reaction mixture was partially purified by reversed-phase HPLC on a C-18 column, eluting with a gradient of H₂O:CH₃CN:TFA-90:10:0.068 to 60:40:0.045, to give the title compound as a mixture of two isomers, (6S)-2'-oxo-N-[(6S,8S)-6-phenyl-5,6,7,8-tetrahydroquinolin-8-yl]-1'%2%5,7-tetrahydrospiro [cyclopenta[b]pyridine-6,3'-pyrrolo[2,3-b]pyridine]-3-carboxamide and (6S)-2'-oxo-N-[(6R,8R)-6-phenyl-5,6,7,8-tetrahydroquinolin-8-yl]-1',2',5,7-tetrahydrospiro [cyclopenta[b]pyridine-6,3'-pyrrolo[2,3-b]pyridine]-3-carboxamide. Separation of these diastereomers was achieved by SFC on a ChiralCel OJ column, eluting with CO₂:EtOH:NH₄OH-60:40:0.002, to afford the title compounds:

(6S)-2'-Oxo-N-(6-phenyl-5,6,7,8-tetrahydroquinolin-8-yl)-1',2',5,7-tetrahydrospiro[cyclopenta[b]pyridine-6,3'-pyrrolo[2,3-b]pyridine]-3-carboxamide, isomer A, which eluted first. MS: m/z=488.3 (M+1). ¹H NMR (400 MHz, DMSO-d₆) δ 8.94 (d, 1H, J=8.4 Hz), 8.87 (s, 1H), 8.42 (d, 1H J=3.6 Hz), 8.10 (s, 1H), 8.02 (d, 1H, J=4.8 Hz), 7.57 (d, 1H, J=7.6 Hz), 7.42-7.33 (m, 5H), 7.26-7.21 (m, 2H), 6.81 (m, 1H), 5.41 (m, 1H), 3.50-3.15 (m, 5H), 3.10-2.90 (m, 2H), 2.40 (m, 1H), 2.17 (m, 1H).

(6S)-2'-Oxo-N-(6-phenyl-5,6,7,8-tetrahydroquinolin-8-yl)-1',2',5,7-tetrahydrospiro [cyclopenta[b]pyridine-6,3'-pyrrolo[2,3-b]pyridine]-3-carboxamide, isomer B, which eluted second. MS: m/z=488.3 (M+1). ¹H NMR (400 MHz, CD₃OD) δ 8.91 (d, 1H, J=1.6 Hz), 8.41 (d, 1H, J=3.6 Hz), 8.18 (t, 1H J=0.8 Hz), 8.09 (dd, 1H, J=5.6, 1.6 Hz), 7.65 (d, 1H J=3.8 Hz), 7.40-7.20 (m, 7H), 6.95 (dd, 1H, J=7.6, 5.6 Hz), 5.51 (dd, 1H, J=11.2, 6.0 Hz), 3.61-3.54 (m, 2H), 3.40-3.20 (m, 3H), 3.12 (d, 2H, J=8.4 Hz), 2.57 (m, 1H), 2.23 (m, 1H).

EXAMPLE 6

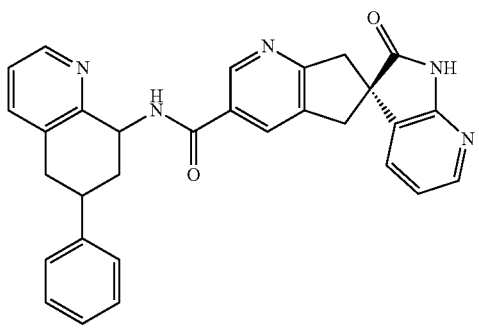 [SMILES: O=C(NC1CC(c2ccccc2)Cc2cccnc21)c1cnc2c(c1)C[C@@]1(C2)C(=O)Nc2ncccc21]

(6S)-2'-Oxo-N-(6-phenyl-5,6,7,8-tetrahydroquinolin-8-yl)-1',2',5,7-tetrahydrospiro[cyclopenta[b]pyridine-6,3'-pyrrolo[2,3-b]pyridine]-3-carboxamide, isomers C & D Essentially following the procedures described for Example 5, but using (6R,8S & 6S,8R)-6-phenyl-5,6,7,8-tetrahydroquinolin-8-amine (described in Intermediate 13) in place of (6S,8S & 6R,8R)-6-phenyl-5,6,7,8-tetrahydroquinolin-8-amine, the title compound was obtained as a mixture of two isomers, (6S)-2'-oxo-N-[(6R,8S)-6-phenyl-5,6,7,8-tetrahydroquinolin-8-yl]-1',2',5,7-tetrahydrospiro[cyclopenta[b]pyridine-6,3'-pyrrolo[2,3-b]pyridine]-3-carboxamide and (6S)-2'-oxo-N-[(6S,8R)-6-phenyl-5,6,7,8-tetrahydroquinolin-8-yl]-1',2',5,7-tetrahydrospiro[cyclopenta[b]pyridine-6,3'-pyrrolo[2,3-b]pyridine]-3-carboxamide. Separation of these diastereomers was achieved by SFC on a Chiralpak AS column, eluting with CO₂:EtOH:NH₄OH 60:40:0.002, to afford the title compounds:

(6S)-2'-Oxo-N-(6-phenyl-5,6,7,8-tetrahydroquinolin-8-yl)-1',2',5,7-tetrahydrospiro [cyclopenta[b]pyridine-6,3'-pyrrolo[2,3-b]pyridine]-3-carboxamide, isomer C, which eluted first. MS: m/z=488.2 (M+1). ¹H NMR (400 MHz, CD₃OD) δ 8.84 (s, 1H), 8.43 (d, 1H, J=4.4 Hz), 8.12 (s, 1H), 8.08 (d, 1H J=5.2 Hz), 7.70 (d, 1H, J=7.6 Hz), 7.34-7.27 (m, 6H), 7.21 (m, 1H), 6.95 (dd, 1H J=7.2, 5.6 Hz), 5.40 (m, 1H), 3.59-3.54 (m, 2H), 3.35-3.20 (m, 3H), 3.15 (dd, 1H J=16.8, 4.4 Hz), 3.02 (dd, 1H J=16.8, 11.2 Hz), 2.42-2.38 (m, 2H).

(6S)-2'-Oxo-N-(6-phenyl-5,6,7,8-tetrahydroquinolin-8-yl)-1',2',5,7-tetrahydrospiro[cyclopenta[b]pyridine-6,3'-pyrrolo[2,3-b]pyridine]-3-carboxamide, isomer D, which eluted second. MS: m/z=488.2 (M+1). ¹H NMR (400 MHz, DMSO-d₆) δ 9.10 (d, 1H, J=7.6 Hz), 8.84 (s, 1H), 8.45 (d, 1H, J=4.0 Hz), 8.10 (s, 1H), 8.07 (dd, 1H, J=5.2, 1.6 Hz), 7.67 (d, 1H J=7.6 Hz), 7.45 (dd, 1H J=7.2, 1.2 Hz), 7.40-7.25 (m, 6H), 7.22 (m, 1H), 6.91 (dd, 1H, J=7.6, 5.6 Hz), 5.30 (m, 1H), 3.50-3.30 (m, 5H), 3.10 (dd, 1H, J=16.8, 4.4 Hz), 2.95 (dd, 1H, J=16.8, 11.2 Hz), 2.30 (m, 1H), 2.15 (d, 1H J=12.0 Hz).

EXAMPLEs 7A & 7B

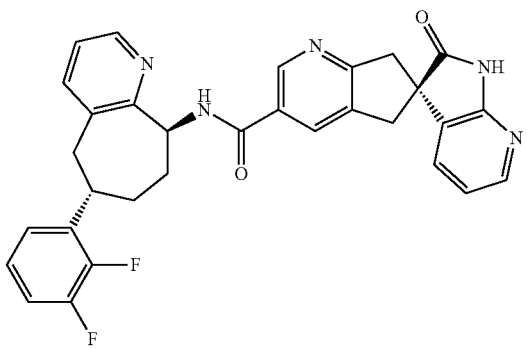

7A

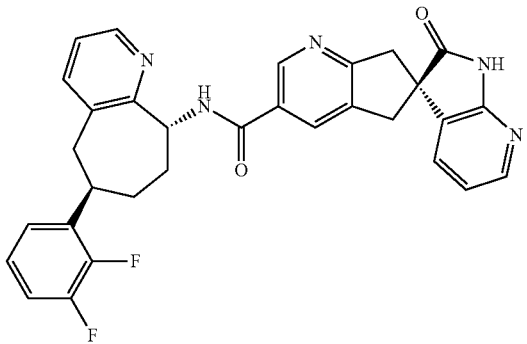

7B (S)—N-((6S,9S)-6-(2,3-Difluorophenyl)-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 7A) and (S)—N-((6R,9R)-6-(2,3-difluorophenyl)-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 7B)

A mixture of the cis and trans isomers (6S,9S and 6R,9R)-6-(2,3-difluorophenyl)-6,7,8,9-tetrahydro-5H-cyclohepta[b]pyridin-9-amine and (6R,9S and 6S,9R)-6-(2,3-difluorophenyl)-6,7,8,9-tetrahydro-5H-cyclohepta[b]pyridin-9-amine (described in Intermediate 14) (0.09 g, 0.32 mmol), (S)-2'-oxo-1',2',5,7-tetrahydrospiro[cyclopenta[b]pyridine-6,3'-pyrrolo[2,3-b]pyridine]-3-carboxylic acid (described in Intermediate 4) (0.111 g, 0.394 mmol), HATU (0.187 g, 0.493 mmol) and N,N-diisopropylethylamine (0.11 g, 0.82 mmol) in DMF (2 mL) was stirred at 23° C. for 16 h. The reaction mixture was partitioned between water and ethyl acetate (3×).

The combined organic layers were washed with brine, dried over anhydrous sodium sulfate, and concentrated. The residue was purified by flash chromatography on silica gel, eluting with 90% ethyl acetate in petroleum ether to give a mixture of two cis and two trans isomers in a 1:1:1:1 ratio. The trans isomers were separated by chiral SFC (Lux C3 column), eluting with 70% CO$_2$ in methanol to give the title compounds.

Isomer A (1$^{st}$ to elute), (S)—N-((6S,9S)-6-(2,3-difluorophenyl)-6,7,8,9-tetrahydro-5H-cyclohepta[b]pyridin-9-yl)-2'-oxo-1',2',5,7-tetrahydrospiro[cyclopenta[b]pyrrolo[2,3-b]pyridine-6,3'-pyrrolo[2,3-b]pyridine]-3-carboxamide (Example 7A): MS: m/z=538.2 (M+1);

$^1$HNMR (400 MHz, CDCl$_3$) δ 8.99 (s, 1H), 8.46 (d, 1H, J=4.6 Hz), 8.27 (s, 1H), 8.11 (d, 1H, J=5.4 Hz), 7.66 (d, 1H, J=7.4 Hz), 7.40 (d, 1H, J=7.4 Hz), 7.32-7.10 (m, 4H), 7.05-6.93 (m, 1H), 5.53-5.43 (m, 2H), 3.68-3.33 (m, 7H), 3.05-2.87 (m, 2H), 2.47-2.38 (m, 2H), 2.04-2.14 (m, 1H), 1.82-1.74 (m, 1H).

Isomer B (2$^{nd}$ to elute), (S)—N-((6R,9R)-6-(2,3-difluorophenyl)-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 7B): MS: m/z=538.2 (M+1);

$^1$HNMR (400 MHz, CDCl$_3$) δ 8.99 (s, 1H), 8.46 (d, 1H, J=4.6 Hz), 8.27 (s, 1H), 8.11 (d, 1H, J=5.4 Hz), 7.66 (d, 1H, J=7.4 Hz), 7.40 (d, 1H, J=7.4 Hz), 7.32-7.25 (m, 2H), 7.19-7.14 (m, 2H), 7.05-6.93 (m, 1H), 5.53-5.43 (m, 2H), 5.42-5.33 (m, 1H), 3.83 (d, 1H, J=17 Hz), 3.74 (d, 1H, J=17 Hz), 3.47-3.20 (m, 3H), 3.05-2.95 (m, 1H), 2.87 (d, 1H, J=14 Hz), 2.70-2.22 (m, 4H), 1.71-1.59 (m, 1H).

EXAMPLES 8C & 8D

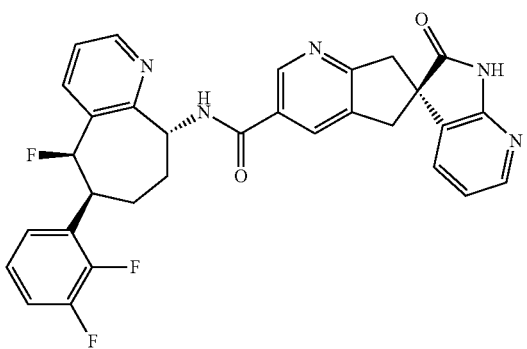

8C

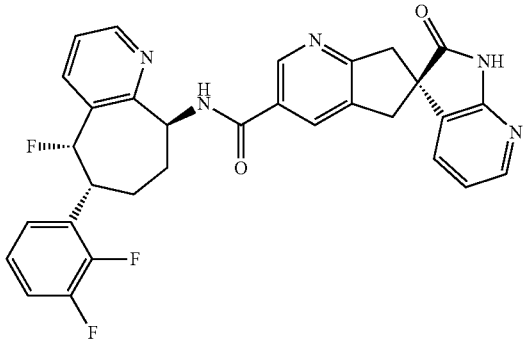

8D (S)—N-((5R,6S,9R)-6-(2,3-Difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 8C) and (S)—N-((5S,6R,9S)-6-(2,3-difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 8D)

A mixture of the isomers (5R,6S,9S and 5S,6R,9R)-6-(2,3-difluorophenyl)-5-fluoro-6,7,8,9-tetrahydro-5H-cyclohepta[b]pyridin-9-amine and (5R,6S,9R and 5S,6R,9S)-6-(2,3-difluorophenyl)-5-fluoro-6,7,8,9-tetrahydro-5H-cyclohepta[b]pyridin-9-amine (described in Intermediate 15) (0.19 g, 0.65 mmol), (S)-2'-oxo-1',2',5,7-tetrahydrospiro[cyclopenta[b] pyridine-6,3'-pyrrolo[2,3-b]pyridine]-3-carboxylic acid (described in Intermediate 4) (0.219 g, 0.780 mmol), HATU (0.37 g, 0.96 mmol) and N,N-diisopropylethylamine (0.21 g, 1.6 mmol) in DMF (5 mL) was stirred at 23° C. for 16 h. The reaction mixture was partitioned between water and ethyl acetate (3×). The combined organic layers were washed with brine, dried over anhydrous sodium sulfate, and concentrated. The residue was purified by flash chromatography on silica gel, eluting with 100% ethyl acetate to give a mixture of four isomeric products which were separated by chiral SFC (Lux C3 column), eluting with 70% CO$_2$ in methanol to give the title compounds:

Isomer A (1$^{st}$ to elute): MS: m/z=556.2 (M+1); $^1$H NMR (400 MHz, CD$_3$OD) δ 8.94 (s, 1H), 8.58 (d, 1H, J=3.8 Hz), 8.21 (s, 1H), 8.11 (d, 1H, J=5.2 Hz), 7.72 (d, 1H, J=5.2 Hz), 7.43-7.36 (m, 2H), 7.20-7.12 (m, 1H), 7.02-6.93 (m, 2H), 6.89-6.72 (bs, 1H), 6.14 (d, 1H, J=46 Hz), 5.53 (bs, 1H), 4.12-3.89 (m, 1H), 3.67-3.54 (m, 2H), 3.42-3.33 (m, 2H), 2.41-2.27 (m, 4H).

Isomer B (2$^{nd}$ to elute): MS: m/z=556.2 (M+1); $^1$H NMR (400 MHz, CD$_3$OD) δ 8.94 (s, 1H), 8.57 (d, 1H, J=4.8 Hz), 8.21 (s, 1H), 8.11 (dd, 1H, J=1.4, 5.3 Hz), 7.72 (d, 1H, J=7.2 Hz), 7.43-7.35 (m, 2H), 7.20-7.11 (m, 1H), 7.01-6.94 (m, 2H), 6.90-6.73 (bs, 1H), 6.14 (d, 1H, J=46 Hz), 5.61-5.49 (bs, 1H), 4.12-3.89 (m, 1H), 3.67-3.54 (m, 2H), 3.42-3.33 (m, 2H), 2.37-2.21 (m, 4H).

Isomer C (3$^{rd}$ to elute), (S)—N-((5R,6S,9R)-6-(2,3-difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 8C): MS: m/z=556.2 (M+1); $^1$H NMR (400 MHz, CD$_3$OD) δ 8.98 (s, 1H), 8.60 (d, 1H, J=4.9 Hz), 8.27 (s, 1H), 8.11 (dd, 1H, J=1.3, 5.4 Hz), 7.80 (d, 1H, J=7.4 Hz), 7.50-7.36 (m, 3H), 7.27-7.18 (m, 2H), 6.99 (dd, 1H, J=5.4, 7.4 Hz), 5.80-5.65 (m, 2H), 3.71-3.59 (m, 2H), 3.42-3.33 (m, 4H), 2.95-2.78 (m, 1H), 2.53-2.38 (m, 1H), 2.11-2.04 (m, 1H), 2.04-1.86 (m, 1H).

Isomer D (4$^{th}$ to elute), (S)—N-((5S,6R,9S)-6-(2,3-difluorophenyl)-5-fluoro-6,7,8,9-tetrahydro-5H-cyclohepta[b]pyridin-9-yl)-2'-oxo-1',2',5,7-tetrahydrospiro[cyclopenta[b]pyridine-6,3'-pyrrolo[2,3-b]pyridine]-3-carboxamide (Example 8D): MS: m/z=556.2 (M+1); $^1$H NMR (400 MHz, CD$_3$OD) δ 8.99 (s, 1H), 8.60 (d, 1H, J=4.9 Hz), 8.27 (s, 1H), 8.11 (dd, 1H, J=1.3, 5.4 Hz), 7.80 (d, 1H, J=7.4 Hz), 7.51-7.33 (m, 3H), 7.26-7.18 (m, 2H), 6.98 (dd, 1H, J=5.4, 7.4 Hz), 5.82-5.65 (m, 2H), 3.68-3.59 (m, 2H), 3.56-3.33 (m, 4H), 2.91-2.83 (m, 1H), 2.53-2.42 (m, 1H), 2.11-1.91 (m, 2H).

EXAMPLE 9

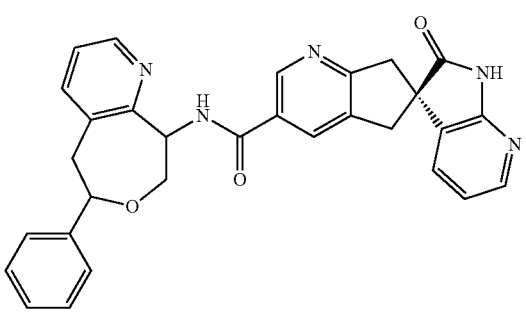 [SMILES: O=C(NC1COC(c2ccccc2)Cc2cccnc21)c1cnc2c(c1)C[C@@]1(C2)C(=O)Nc2ncccc21]

(3'S)-2'-Oxo-N-(6-phenyl-5,6,8,9-tetrahydrooxepino[4,5-b]pyridin-9-yl)-1',2',5,7-tetrahydrospiro[cyclopenta[b]pyridine-6,3'-pyrrolo[2,3-b]pyridine]-3-carboxamide A mixture of isomer set A (described in Intermediate 16) (30 mg, 0.12 mmol), (S)-2'-oxo-1',2',5,7-tetrahydrospiro[cyclopenta[b]pyridine-6,3'-pyrrolo[2,3-b]pyridine]-3-carboxylic acid (described in Intermediate 4) (42 mg, 0.15 mmol), HATU (71 mg, 0.19 mmol) and N,N-diisopropylethylamine (0.070 mL, 0.31 mmol) in DMF (2 mL) was stirred at 23° C. for 18 h. The reaction mixture was partitioned between water and ethyl acetate (2×). The combined organic layers were washed with brine, dried over anhydrous sodium sulfate, and concentrated.

The residue was purified by flash chromatography on silica gel, eluting with 4% methanol in dichloromethane to give a mixture of two isomers which were separated by chiral SFC (ChiralCel OD-H column), eluting with 40% $CO_2$ in methanol to give the title compound.

Isomer A (1$^{st}$ to elute): MS: m/z=504.2 (M+1); $^1$H NMR (400 MHz, $CD_3OD$): δ 8.89 (s, 1H), 8.43 (d, 1H, J=4.3 Hz), 8.17 (s, 1H), 8.10 (d, 1H, J=5.3 Hz), 7.63 (d, 1H, J=7.8 Hz), 7.27-7.42 (m, 7H), 6.97 (dd, 1H, J=5.4, 7.1 Hz), 5.50 (dd, 1H, J=2.9, 5.1 Hz), 4.82 (dd, 1H, J=2.4, 8.2 Hz), 4.41 (dd, 1H, J=5.4, 12.7 Hz), 4.14 (dd, 1H, J=2.8, 12.8 Hz), 3.56-3.71 (m, 3H), 3.37-3.36 (m, 2H), 3.24 (dd, 1H, J=2.4, 15.7 Hz).

Isomer B (2$^{nd}$ to elute): MS: m/z=504.2 (M+1); $^1$H NMR (400 MHz, $CD_3OD$): δ 8.89 (s, 1H), 8.43 (d, 1H, J=4.5 Hz), 8.18 (s, 1H), 8.10 (d, 1H, J=5.0 Hz), 7.63 (d, 1H, J=7.5 Hz), 7.25-7.43 (m, 7H), 6.94-7.00 (m, 1H), 5.46-5.52 (m, 1H), 4.82 (d, 1H, J=6.3 Hz), 4.40 (dd, 1H, J=5.4, 12.7 Hz), 4.14 (dd, 1H, J=2.6, 12.7 Hz), 3.56-3.70 (m, 3H), 3.35-3.40 (m, 2H), 3.22-3.28 (m, 1H).

Similarly, a mixture of isomer set B (described in Intermediate 16) (35 mg, 0.14 mmol), (S)-2'-oxo-1',2',5,7-tetrahydrospiro[cyclopenta[b]pyridine-6,3'-pyrrolo[2,3-b]pyridine]-3-carboxylic acid (described in Intermediate 4) (49 mg, 0.17 mmol), HATU (80 mg, 0.22 mmol) and N,N-diisopropylethylamine (0.090 mL, 0.36 mmol) in DMF (2 mL) was stirred at 23° C. for 18 h. The reaction mixture was partitioned between water and ethyl acetate (2×). The combined organic layers were washed with brine, dried over anhydrous sodium sulfate, and concentrated. The residue was purified by flash chromatography on silica gel, eluting with 4% methanol in dichloromethane to give a mixture of two isomers which were separated by chiral SFC (ChiralCel OD-H column), eluting with 40% $CO_2$ in methanol to give the title compound.

Isomer C (1$^{st}$ to elute): MS: m/z=504.2 (M+1); $^1$H NMR (400 MHz, $CD_3OD$): δ 9.00 (d, 1H, J=1.5 Hz), 8.48 (dd, 1H, J=1.1, 4.9 Hz), 8.25-8.30 (m, 1H), 8.11 (dd, 1H, J=1.4, 5.4 Hz), 7.68-7.73 (m, 1H), 7.48 (d, 2H, J=7.5 Hz), 7.36-7.42 (m, 3H), 7.28-7.33 (m, 2H), 6.98 (dd, 1H, J=5.5, 7.3 Hz), 5.67 (dd, 1H, J=2.3, 9.3 Hz), 4.53 (d, 1H, J=9.8 Hz), 4.42 (dd, 1H, J=2.5, 11.8 Hz), 3.47-3.74 (m, 4H), 3.40 (s, 1H), 3.36 (s, 1H), 3.08 (d, 1H, J=15.3 Hz).

Isomer D (2$^{nd}$ to elute): MS: m/z=504.2 (M+1); $^1$H NMR (400 MHz, $CD_3OD$): δ 8.99 (d, 1H, J=2.0 Hz), 8.48 (dd, 1H, J=1.2, 4.9 Hz), 8.28 (d, 1H, J=2.0 Hz), 8.11 (dd, 1H, J=1.5, 5.3 Hz), 7.70 (dd, 1H, J=1.2, 7.5 Hz), 7.46-7.51 (m, 2H), 7.36-7.43 (m, 3H), 7.28-7.34 (m, 2H), 6.99 (dd, 1H, J=5.4, 7.4 Hz), 5.67 (dd, 1H, J=2.4, 9.2 Hz), 4.54 (d, 1H, J=9.5 Hz), 4.42 (dd, 1H, J=2.5, 11.8 Hz), 3.47-3.73 (m, 4H), 3.41 (d, 1H, J=2.8 Hz), 3.35-3.37 (m, 1H), 3.08 (d, 1H, J=15.1 Hz).

PHARMACEUTICAL COMPOSITION

As a specific embodiment of this invention, 100 mg of (6S)—N-[(5S,6S,9R)-5-Amino-6-(2,3-difluorophenyl)-6,7,8,9-tetrahydro-5H-cyclohepta[b]pyridin-9-yl]-2'-oxo-1',2',5,7-tetrahydrospiro [cyclopenta[b]pyridine-6,3'-pyrrolo[2,3-b]pyridine]-3-carboxamide is formulated with sufficient finely divided lactose to provide a total amount of 580 to 590 mg to fill a size 0, hard-gelatin capsule.

What is claimed is:
1. A compound which is:
   (6S)—N-[(5S,6S,9R)-5-Amino-6-(2,3-difluorophenyl)-6,7,8,9-tetrahydro-5H-cyclohepta[b]pyridin-9-yl]-2'-oxo-1',2',5,7-tetrahydrospiro[cyclopenta[b]pyridine-6,3'-pyrrolo[2,3-b]pyridine]-3-carboxamide;
   (6S)—N-[(5S,6S,9S)-5-Amino-6-(2,3-difluorophenyl)-6,7,8,9-tetrahydro-5H-cyclohepta[b]pyridin-9-yl]-2'-oxo-1',2',5,7-tetrahydrospiro [cyclopenta[b]pyridine-6,3'-pyrrolo [2,3 -b]pyridine]-3 -carboxamide;
   (6S)—N-[(5R,6S,9R)-5-Amino-6-(2,3-difluorophenyl)-6,7,8,9-tetrahydro-5H-cyclohepta [b]pyridin-9-yl]-2'-oxo-1',2',5,7-tetrahydrospiro [cyclopenta[b]pyridine-6,3'-pyrrolo [2,3 -b]pyridine]-3-carboxamide; or
   (6S)—N-[(5R,6S,9S)—-5-Amino-6-(2,3-difluorophenyl)-6,7,8,9-tetrahydro-5H-cyclohepta[b]pyridin-9-yl]-2'-oxo-1',2',5,7-tetrahydro spiro [cyclopenta[b]pyridine-6,3'-pyrrolo [2,3 -b]pyridine]-3-carboxamide;
   or a pharmaceutically acceptable salt of any thereof.
2. A compound of the Formula:

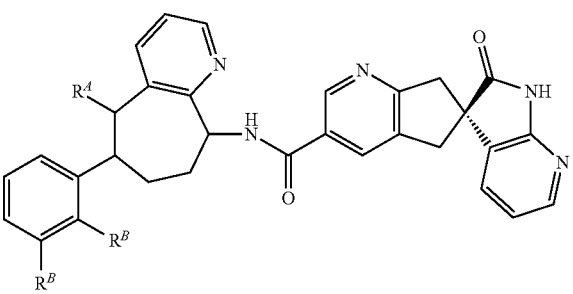

wherein, $R^A$ is —$NH_2$, —F, or —H, and $R^B$ are both -F or both —H.

3. A pharmaceutical composition comprising a compound of claim 2, or a pharmaceutically acceptable salt thereof and a pharmaceutically acceptable carrier.

4. A method of treating Migraine by providing an effective amount of a pharmaceutical formulation of claim 3 to a patient in need thereof.

* * * * *